(12) United States Patent
Lee et al.

(10) Patent No.: US 12,010,913 B2
(45) Date of Patent: Jun. 11, 2024

(54) COMPOUND FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Hanill Lee, Suwon-si (KR); Wook Kim, Suwon-si (KR); Hyung Sun Kim, Suwon-si (KR); Yongtak Yang, Suwon-si (KR); Jiah Yoon, Suwon-si (KR); Mijin Lee, Suwon-si (KR); Suyong Lim, Suwon-si (KR); Sung-Hyun Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 717 days.

(21) Appl. No.: 17/036,317

(22) Filed: Sep. 29, 2020

(65) Prior Publication Data

US 2021/0104684 A1    Apr. 8, 2021

(30) Foreign Application Priority Data

Oct. 2, 2019    (KR) .................. 10-2019-0122526

(51) Int. Cl.
*H10K 85/60*    (2023.01)
*C07D 403/04*    (2006.01)
(Continued)

(52) U.S. Cl.
CPC ....... *H10K 85/6572* (2023.02); *C07D 403/04* (2013.01); *C07D 405/14* (2013.01);
(Continued)

(58) Field of Classification Search
CPC ............ H01K 85/6572; H01K 85/622; H01K 85/654; H01K 50/11; C07D 403/04;
(Continued)

(56) References Cited

U.S. PATENT DOCUMENTS 5,061,569 A    10/1991    Vanslyke et al.
9,673,401 B2    6/2017    Boudreault et al.
(Continued)

FOREIGN PATENT DOCUMENTS

CN    104080882 A    10/2014
JP    H5-9471 A    1/1993
(Continued)

OTHER PUBLICATIONS

Chinese Office Action dated Feb. 28, 2023.

*Primary Examiner* — Ruiyun Zhang
(74) *Attorney, Agent, or Firm* — Lee IP Law, P.C.

(57) ABSTRACT

A compound for an organic optoelectronic device, an organic optoelectronic device, and a display device, the compound being represented by Chemical Formula 1:

[Chemical Formula 1]

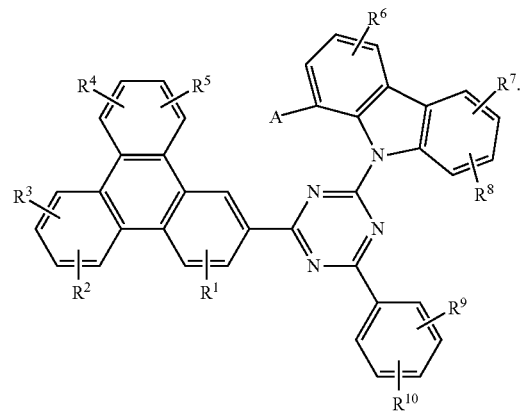

11 Claims, 1 Drawing Sheet

(51) Int. Cl.
*C07D 405/14* (2006.01)
*C07D 409/14* (2006.01)
*C09K 11/06* (2006.01)
*H10K 50/11* (2023.01)
*H10K 101/10* (2023.01)

(52) U.S. Cl.
CPC ............ *C07D 409/14* (2013.01); *C09K 11/06* (2013.01); *H10K 85/622* (2023.02); *H10K 85/626* (2023.02); *H10K 85/654* (2023.02); *H10K 85/6574* (2023.02); *H10K 85/6576* (2023.02); *C09K 2211/1018* (2013.01); *H10K 50/11* (2023.02); *H10K 2101/10* (2023.02)

(58) Field of Classification Search
CPC .... C07D 405/14; C07D 409/14; C09K 11/06; C09K 2211/1018
USPC ......................................................... 428/690
See application file for complete search history.

(56) References Cited

U.S. PATENT DOCUMENTS

| | | |
|---|---|---|
| 2012/0211736 A1 | 8/2012 | Kim et al. |
| 2012/0235136 A1 | 9/2012 | Ogawa et al. |
| 2015/0001471 A1 * | 1/2015 | Boudreault .......... C07D 403/04 544/212 |
| 2015/0349268 A1 | 12/2015 | Zeng et al. |

FOREIGN PATENT DOCUMENTS

| | | | |
|---|---|---|---|
| JP | H7-126615 A | | 5/1995 |
| JP | H 10-95972 A | | 4/1998 |
| JP | 2006-143845 A | | 6/2006 |
| JP | 5584702 B2 | | 9/2014 |
| KR | 10-0948700 B1 | | 3/2010 |
| KR | 10-1183722 B1 | | 9/2012 |
| KR | 10-2012-0116282 A | | 10/2012 |
| KR | 20120116282 A | * | 10/2012 |
| KR | 10-2013-0062583 A | | 6/2013 |
| KR | 10-2014-0113483 A | | 9/2014 |
| KR | 10-2014-0135524 A | | 11/2014 |
| KR | 10-1618683 B1 | | 5/2016 |
| KR | 10-2017-0069342 A | | 6/2017 |
| KR | 10-2017-0070359 A | | 6/2017 |
| KR | 10-2018-0027457 A | | 3/2018 |
| KR | 10-2018-0063708 A | | 6/2018 |
| KR | 10-2019-0004517 A | | 1/2019 |
| KR | 10-2019-0090204 A | | 8/2019 |
| WO | WO 1995/009147 A1 | | 4/1995 |
| WO | WO 2017/069258 A1 | | 4/2017 |

* cited by examiner

COMPOUND FOR ORGANIC OPTOELECTRONIC DEVICE, ORGANIC OPTOELECTRONIC DEVICE AND DISPLAY DEVICE

CROSS-REFERENCE TO RELATED APPLICATION

Korean Patent Application No. 10-2019-0122526, filed on Oct. 2, 2019, in the Korean Intellectual Property Office, and entitled: "Compound for Organic Optoelectronic Device and Display Device," is incorporated by reference herein in its entirety.

BACKGROUND OF THE INVENTION

1. Field

Embodiments relate to a compound for an organic optoelectronic device, an organic optoelectronic device, and a display device.

2. Description of the Related Art

An organic optoelectronic device (e.g., organic optoelectronic diode) is a device that converts electrical energy into photoenergy, and vice versa.

An organic optoelectronic device may be classified as follows in accordance with its driving principles. One is a photoelectric device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectronic device may include an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and performance of an organic light emitting diode may be affected by organic materials disposed between electrodes.

SUMMARY

The embodiments may be realized by providing a compound for an organic optoelectronic device, the compound being represented by Chemical Formula 1:

[Chemical Formula 1]

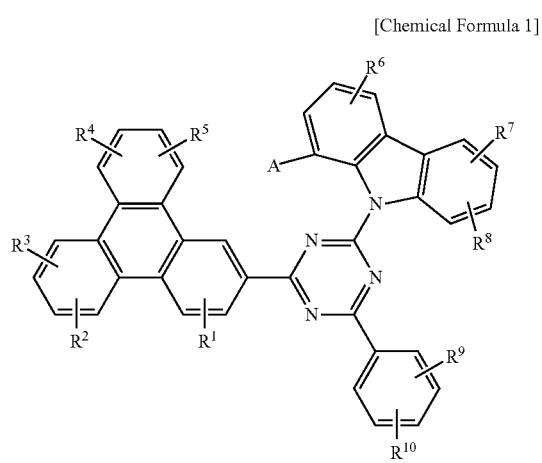

wherein, in Chemical Formula 1, A is a substituted or unsubstituted C10 to C20 aryl group or a substituted or unsubstituted C10 to C20 heterocyclic group, $R^1$ to $R^8$ are independently hydrogen, deuterium, a substituted or unsubstituted C1 to C10 alkyl group, or a substituted or unsubstituted C6 to C20 aryl group, and $R^9$ and $R^{10}$ are independently hydrogen, deuterium, or an unsubstituted phenyl group.

The compound represented by Chemical Formula 1 may be represented by one of Chemical Formulae 1-1 to 1-4:

[Chemical Formula 1-1]

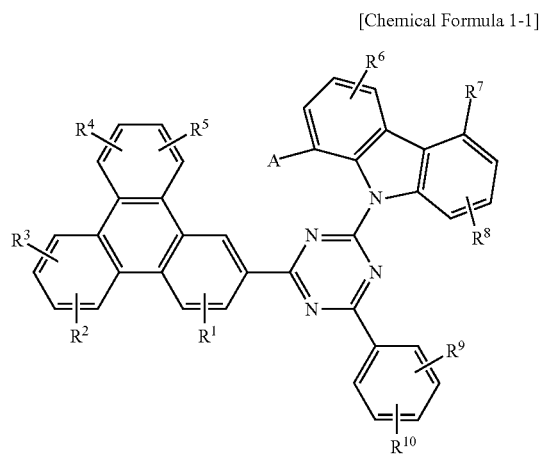

[Chemical Formula 1-2]

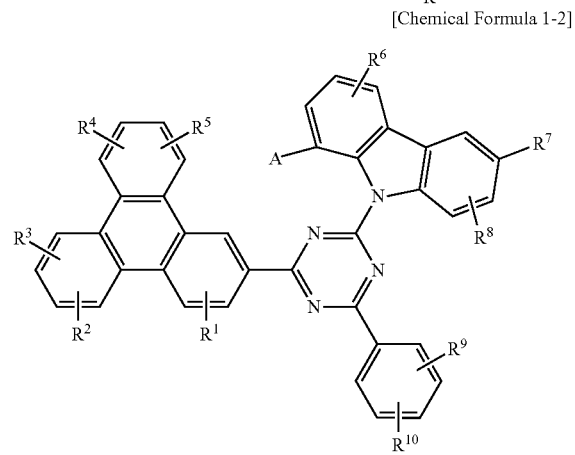

[Chemical Formula 1-3]

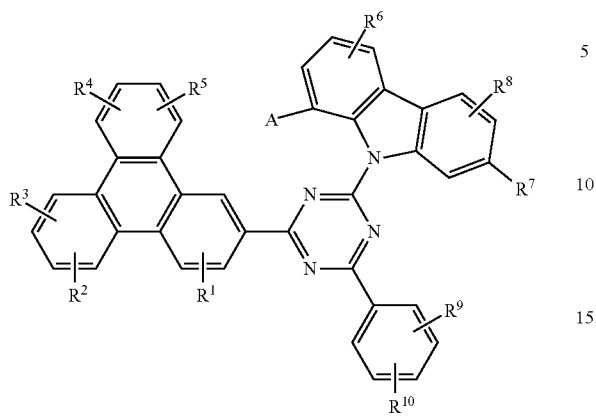

[Chemical Formula 1-4]

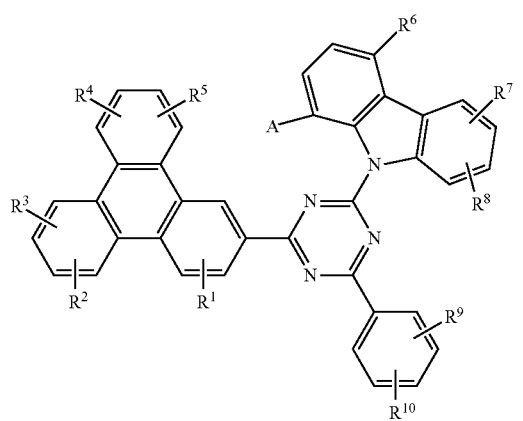

in Chemical Formulae 1-1 to 1-4, A and $R^1$ to $R^{10}$ may be defined the same as those of Chemical Formula 1.

A may be a substituted or unsubstituted biphenyl group, a substituted or unsubstituted terphenyl group, a substituted or unsubstituted fluorenyl group, a substituted or unsubstituted dibenzofuranyl group, or a substituted or unsubstituted dibenzothiophenyl group.

A may be a substituent of Group I:

[Group I]

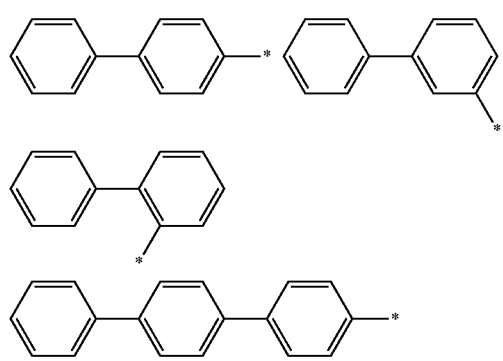

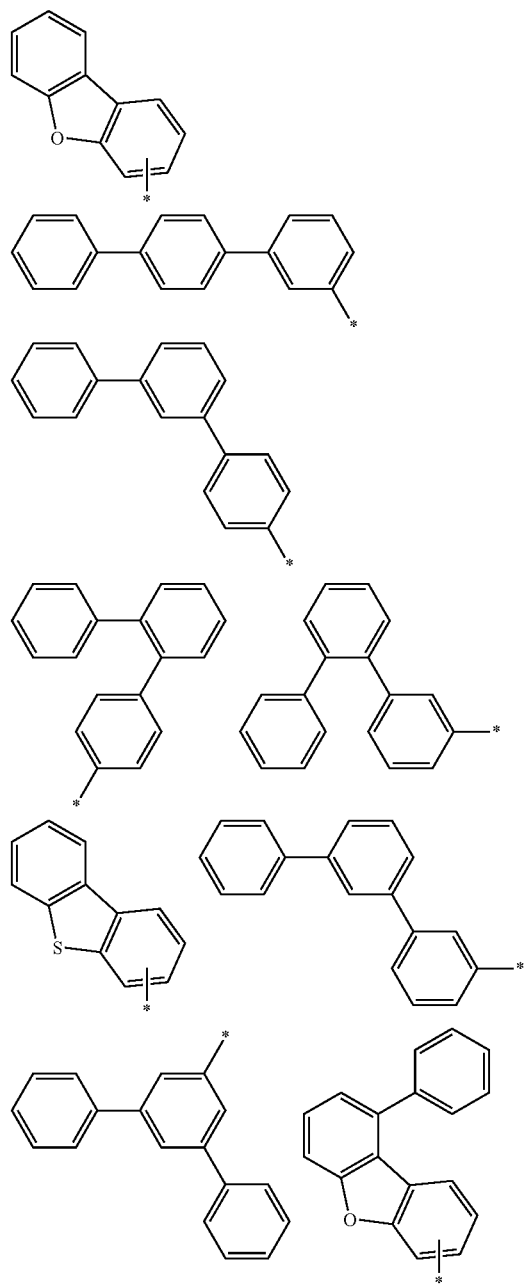

in Group I, $R^a$ and $R^b$ may be independently a substituted or unsubstituted C1 to C6 alkyl group or a substituted or unsubstituted C6 to C12 aryl group, and * is a linking point.

The compound represented by Chemical Formula 1 may be a compound of Group 1:
[Group 1]
[A-1]
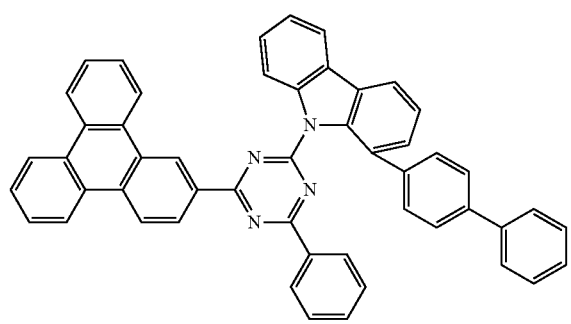
[A-2]
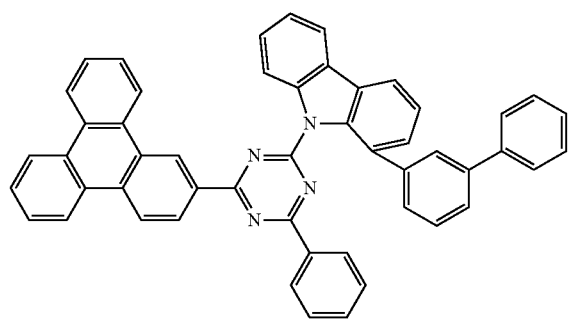
[A-3]
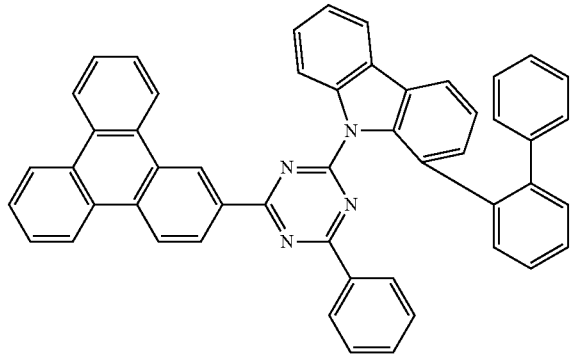
[A-4]
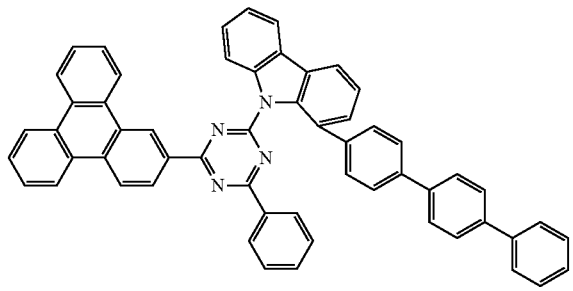
[A-5]
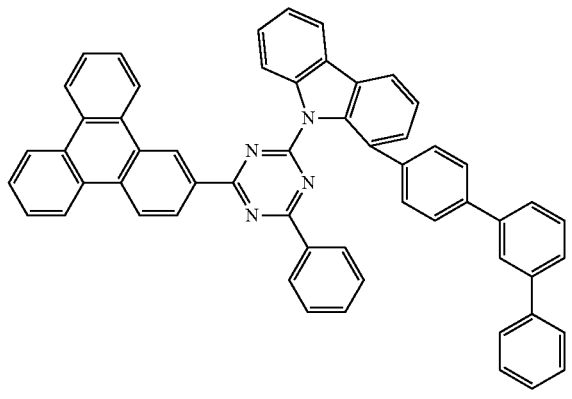
[A-6]
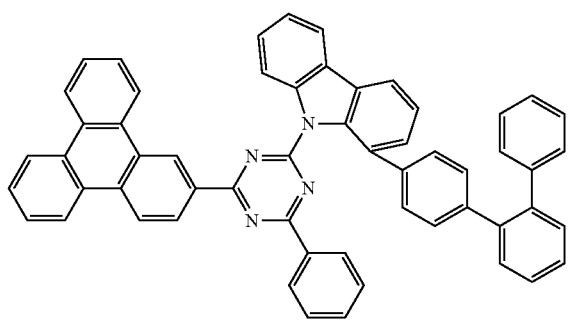
[A-7]
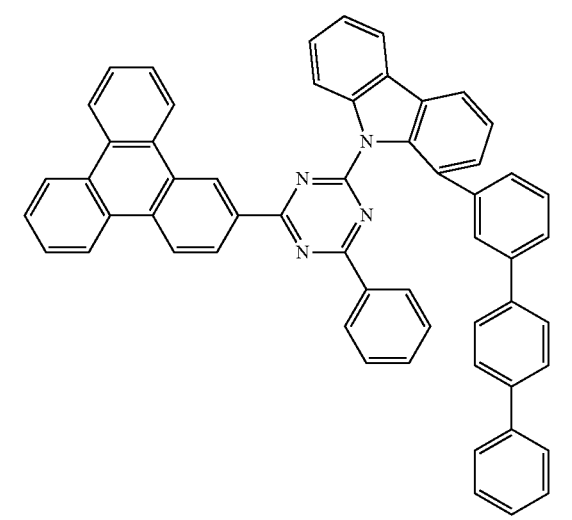
[A-8]
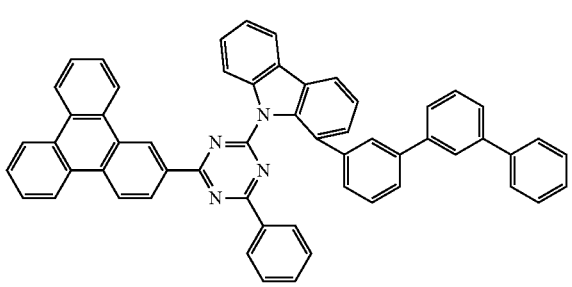

-continued
[A-9]
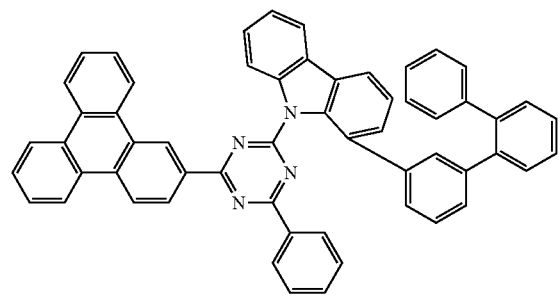
[A-10]
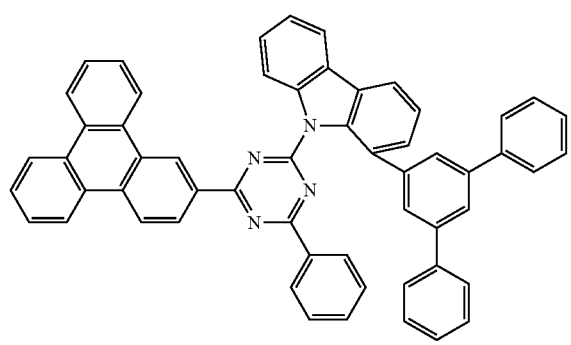
[A-11]
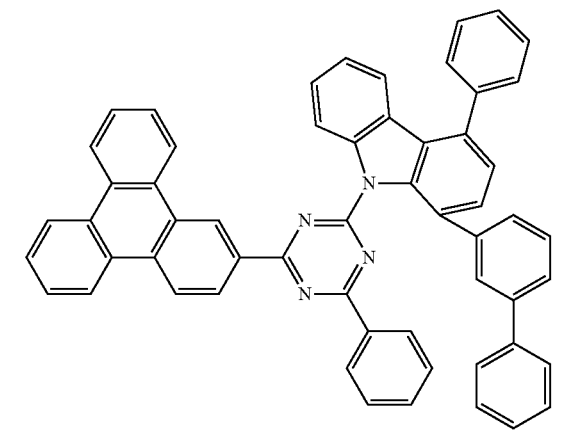
[A-12]
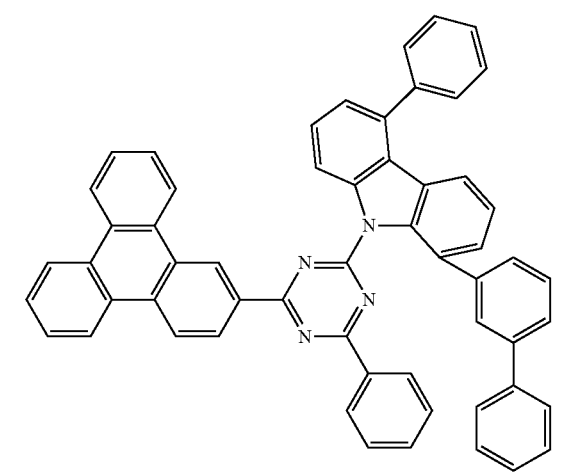
[A-13]
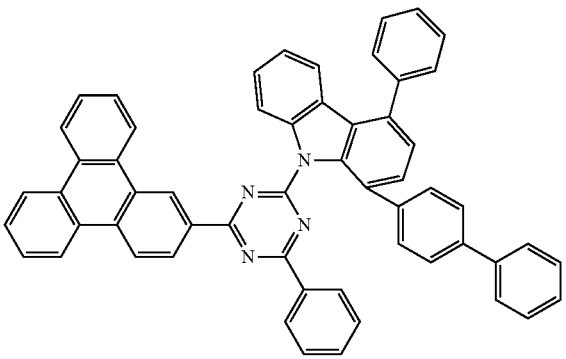
[A-14]
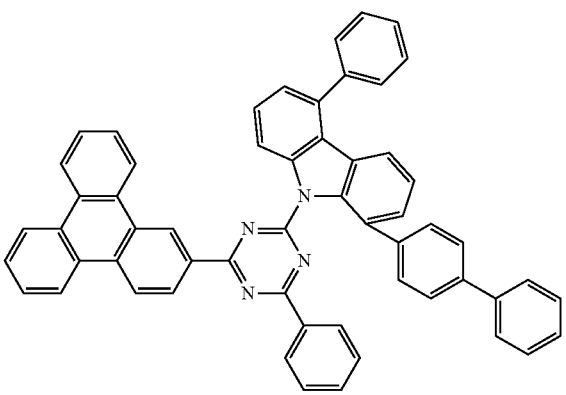
[A-15]
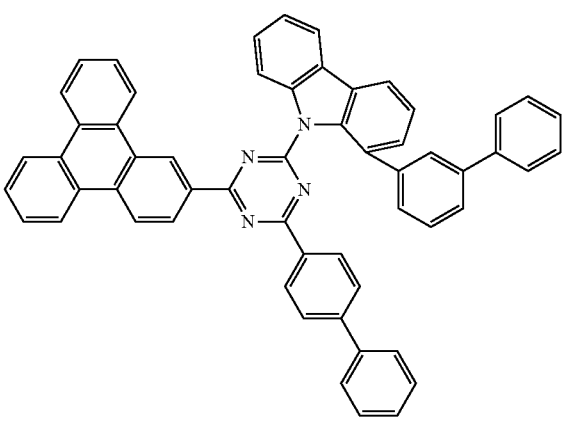
[A-16]
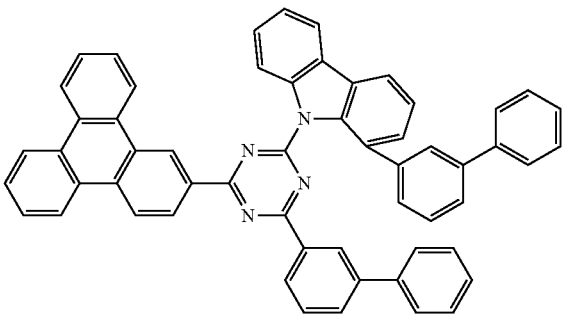

[A-17]
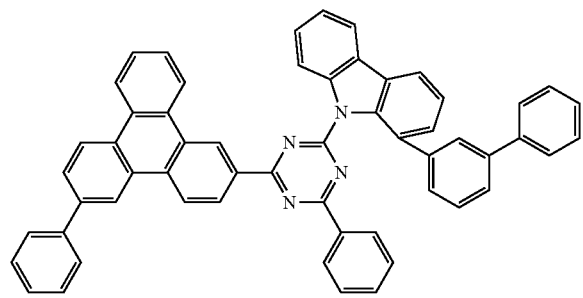
[A-18]
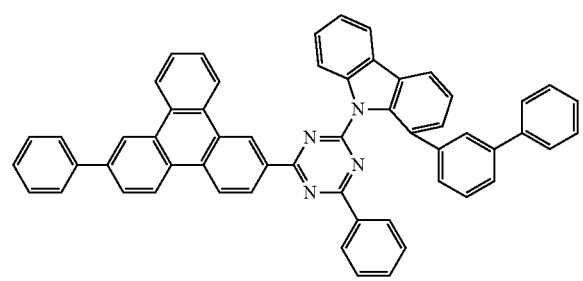
[A-19]
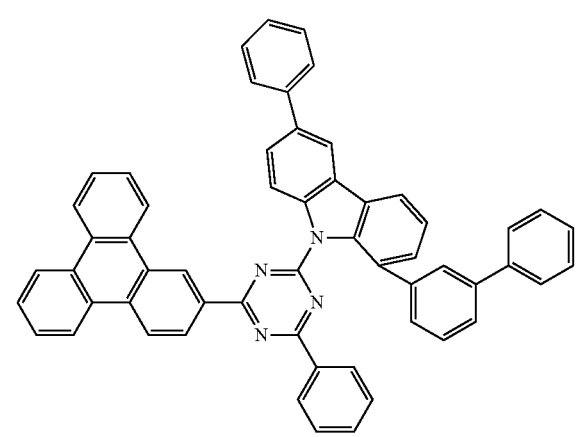
[A-20]
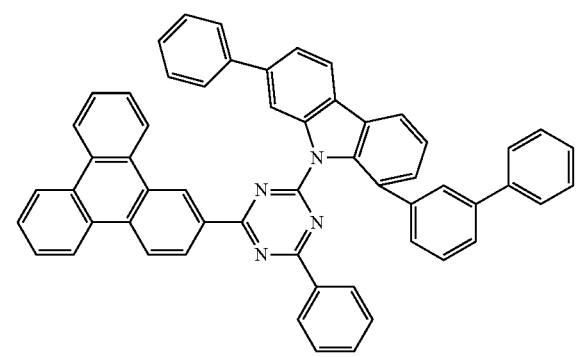
[A-21]
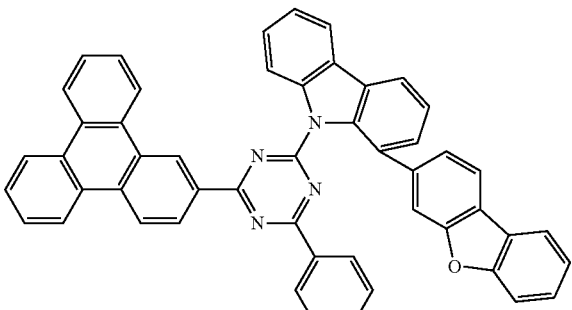
[A-22]
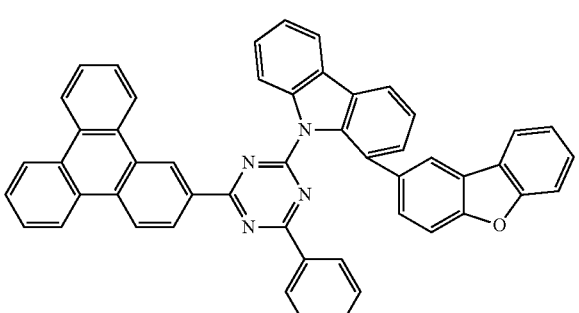
[A-23]
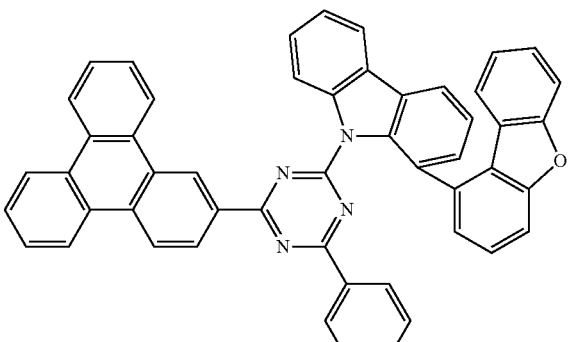
[A-24]
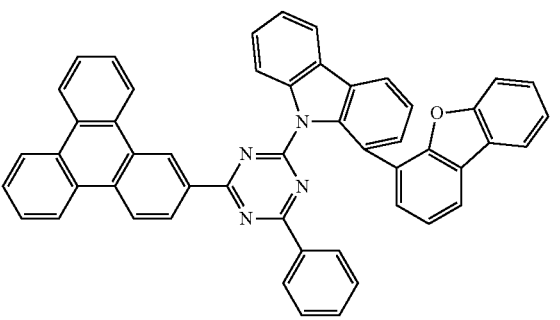

[A-25]
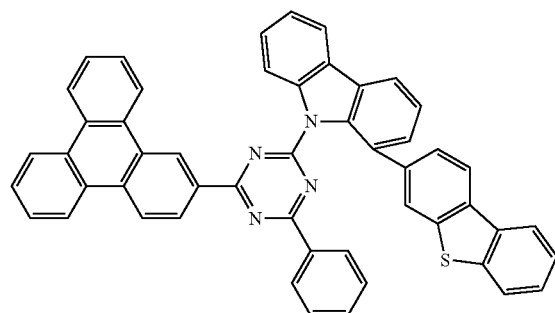
[A-29]
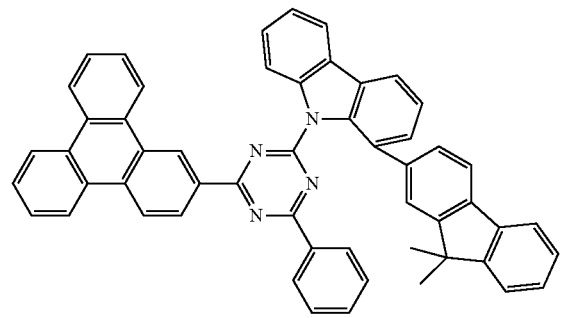
[A-26]
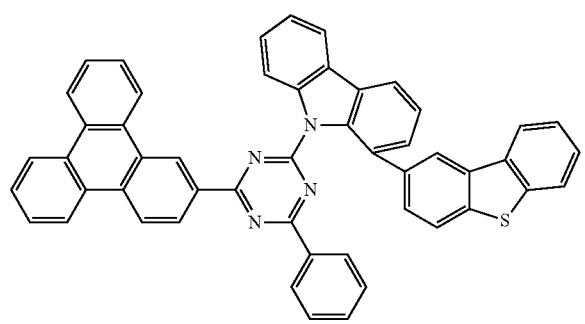
[A-30]
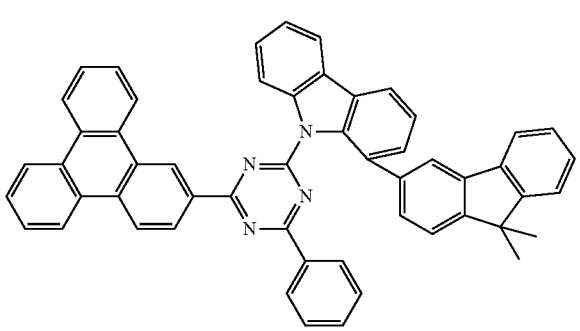
[A-27]
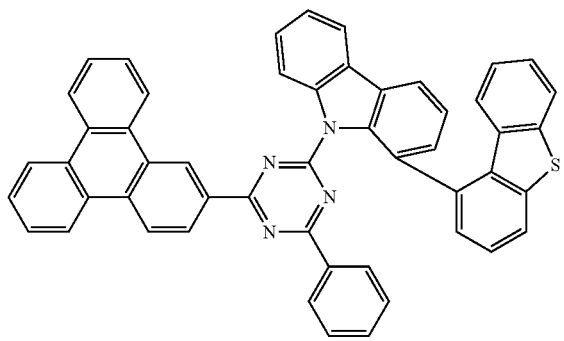
[A-31]
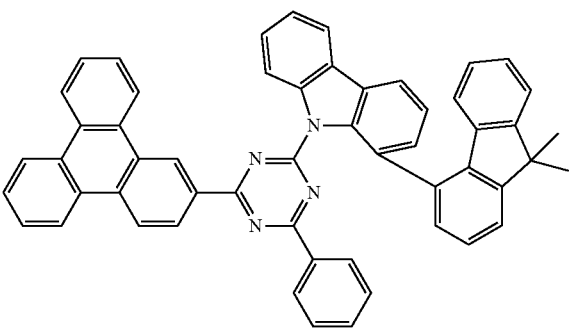
[A-28]
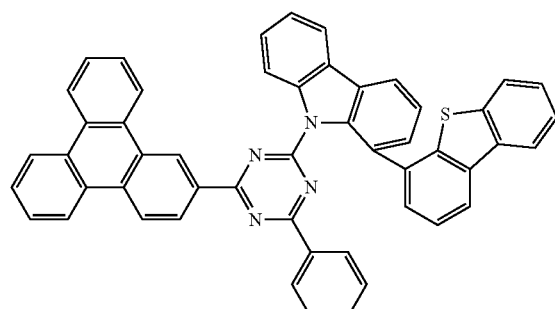
[A-32]
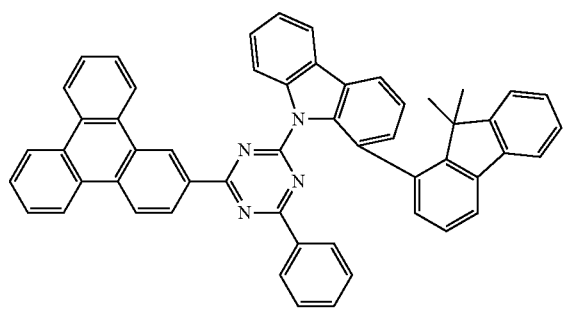

[A-33]
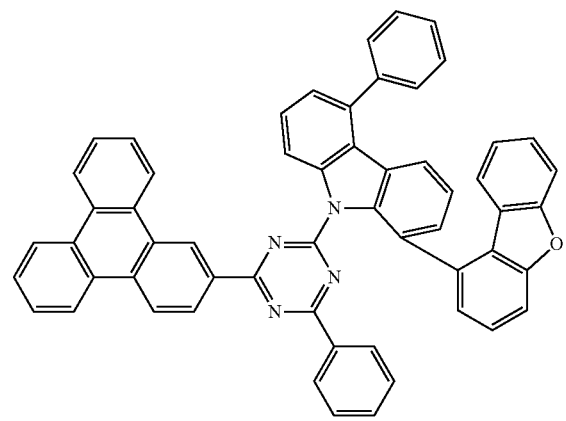
[A-34]
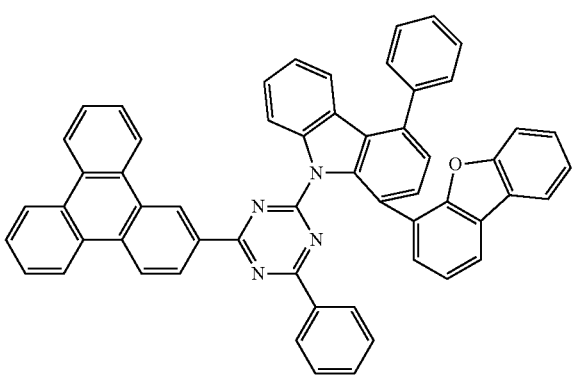
[A-35]
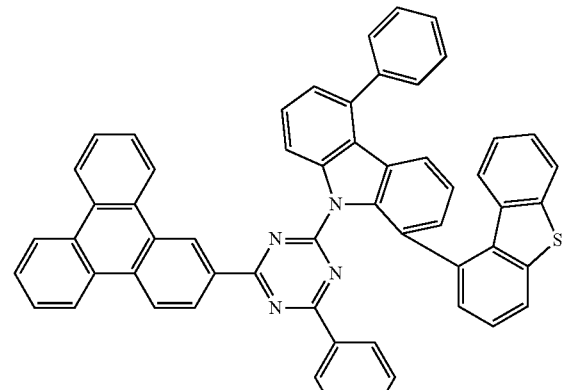
[A-36]
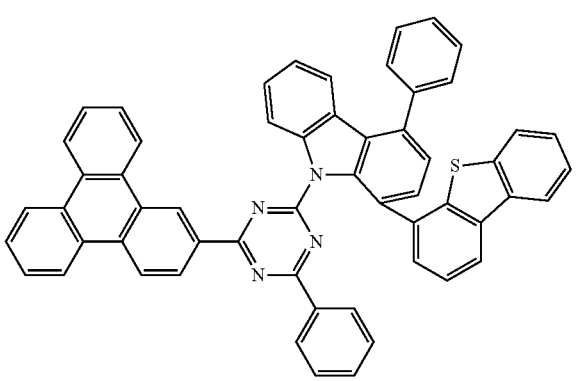
[A-37]
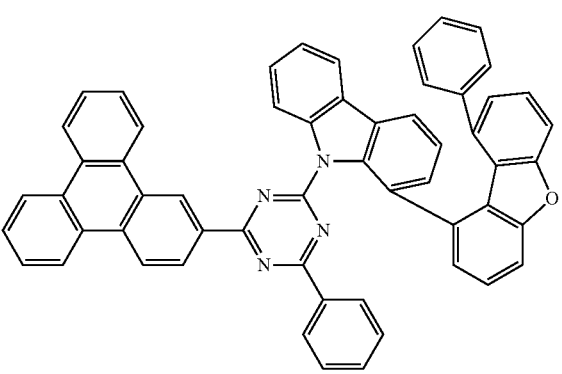
[A-38]
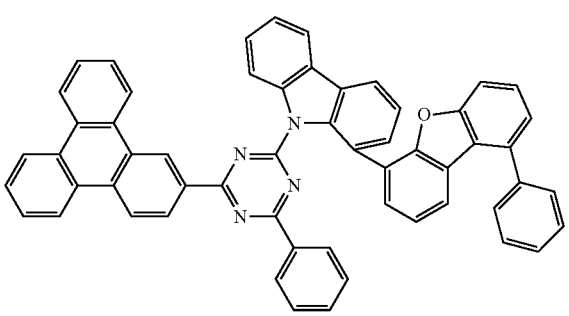
[A-39]
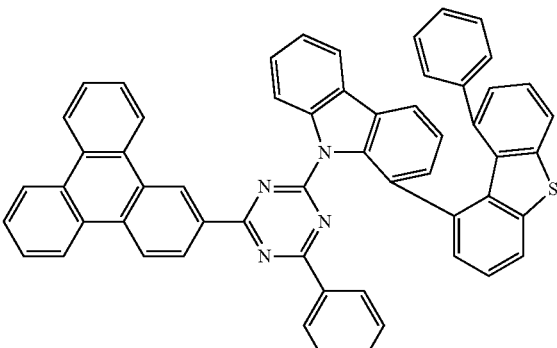
[A-40]
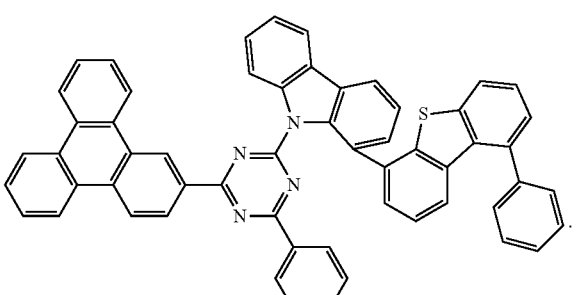
The embodiments may be realized by providing an organic optoelectronic device including an anode and a cathode facing each other, and at least one organic layer between the anode and the cathode, wherein the at least one organic layer includes the compound according to an embodiment.

The at least one organic layer may include a light emitting layer, and the light emitting layer may include the compound.

The embodiments may be realized by providing a display device comprising the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
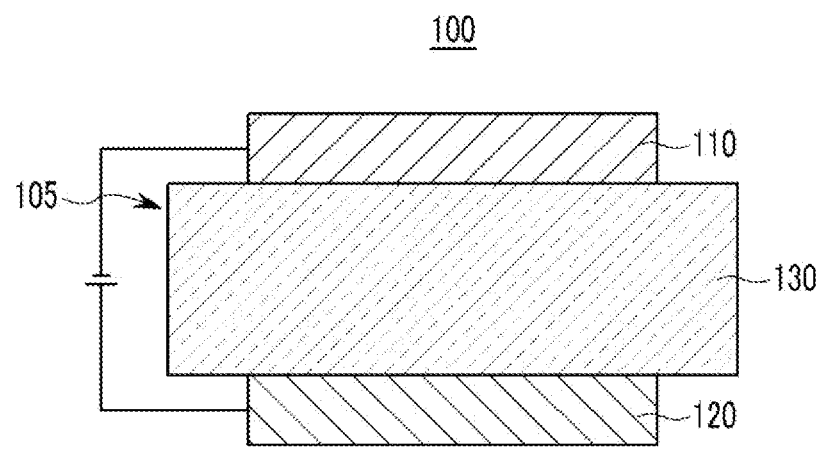
FIGS. 1 and 2 are cross-sectional views of an organic light emitting diode according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in specific examples of the present invention, "substituted" refers to replacement of at least one hydrogen of a substituent or a compound by deuterium, a C1 to C20 alkyl group, a C6 to C30 aryl group, or a cyano group. In addition, in specific examples of the present invention, "substituted" refers to replacement of at least one hydrogen of a substituent or a compound by deuterium, a C1 to C5 alkyl group, a C6 to C18 aryl group, or a cyano group. In addition, in specific examples of the present invention, "substituted" refers to replacement of at least one hydrogen of a substituent or a compound by deuterium, a cyano group, a methyl group, an ethyl group, a propanyl group, a butyl group, a phenyl group, a biphenyl group, a terphenyl group, or a naphthyl group.

As used herein, when a definition is not otherwise provided, "hetero" refers to one including one to three heteroatoms selected from N, O, S, P, and Si, and remaining carbons in one functional group.

As used herein, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring, for example a fluorenyl group, and the like.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof.

In the present specification, hole characteristics refer to an ability to donate an electron to form a hole when an electric field is applied and that a hole formed in the anode may be easily injected into the light emitting layer and transported in the light emitting layer due to conductive characteristics according to the highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to the lowest unoccupied molecular orbital (LUMO) level.

Hereinafter, a compound for an organic optoelectronic device according to an embodiment is described.

The compound for the organic optoelectronic device according to an embodiment may be represented by Chemical Formula 1.

The compound simultaneously includes a triphenylene substituent, which may easily accept holes, and a triazine core, which may easily accept electrons, thereby appropriately localizing the HOMO electron cloud and the LUMO electron cloud. By controlling a flow of the conjugated system, excellent bipolar characteristics may be exhibited, and accordingly, the life-span of the organic optoelectronic device including the compound may be improved.

In an implementation, by introducing N-carbazole into the triazine core to form a C—N bond, the π-bond may be broken, thereby preventing an expansion of the HOMO electron cloud. This may facilitate effective localization to further maximize the above-described long life-span effect.

In an implementation, by introducing an additional substituent at the position No. 1 of the N-carbazole, the triazine plane and the carbazole plane may be distorted to help prevent crystallization derived from the planar structure of the molecule, and thus, a long-life span, low-driving, high-efficiency device may be implemented.

This is presumed to be a result of stronger hole characteristics and more pronounced localization as the HOMO electron cloud expands to the position No. 1 of N-carbazole.

In an implementation, the compound represented by Chemical Formula 1 may be represented by, e.g., one of Chemical Formula 1-1 to Chemical Formula 1-4, depending on the position of a substituent other than the position No. 1 of the carbazole.

[Chemical Formula 1]

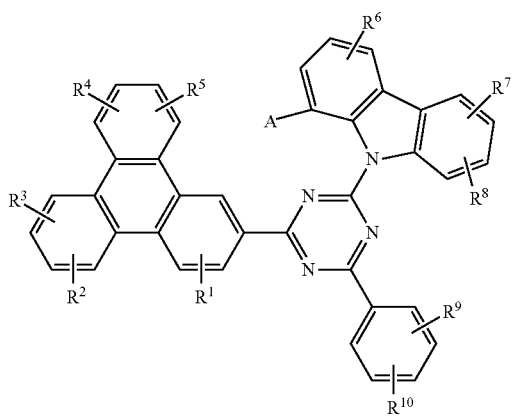

[Chemical Formula 1-1]

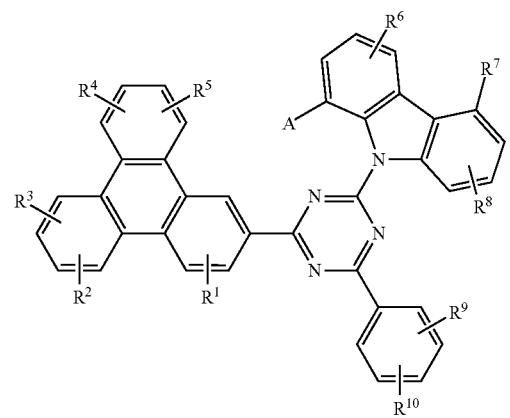

In Chemical Formula 1,

A may be or may include, e.g., a substituted or unsubstituted C10 to C20 aryl group or a substituted or unsubstituted C10 to C20 heterocyclic group, $R^1$ to $R^8$ may each independently be or include, e.g., hydrogen, deuterium, a substituted or unsubstituted C10 to C10 alkyl group, or a substituted or unsubstituted C6 to C20 aryl group, and $R^9$ and $R^{10}$ may each independently be or include, e.g., hydrogen, deuterium, or a phenyl group (e.g., a substituted or unsubstituted phenyl group).

The compound represented by Chemical Formula 1 may include a substituted or unsubstituted phenyl group, a substituted or unsubstituted triphenylene group, and an N-carbazole group including a substituent at the position No. 1, all of which substitute the triazine core.

[Chemical Formula 1-2]

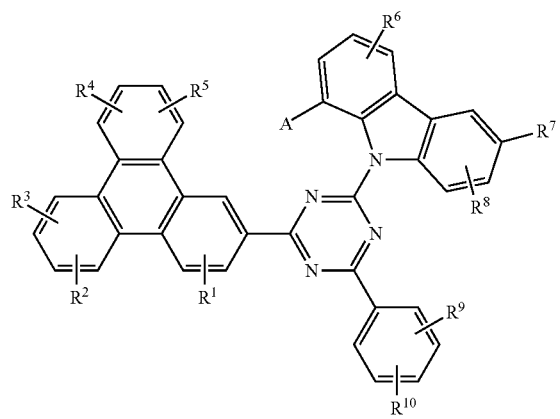

-continued

[Chemical Formula 1-3]

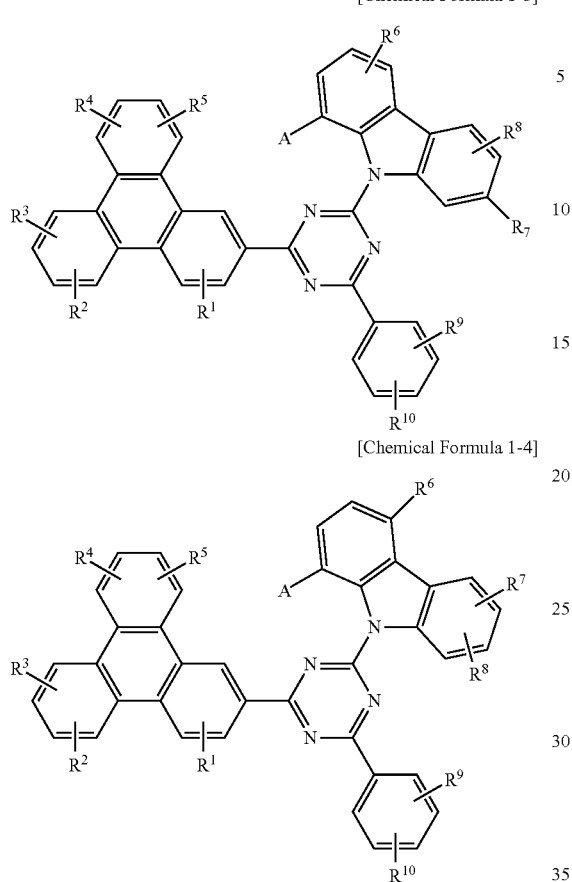

[Chemical Formula 1-4]

In Chemical Formulae 1-1 to 1-4, A and $R^1$ to $R^{10}$ may be defined the same as described above with respect to Chemical Formula 1.

In an implementation, $R^7$ of Chemical Formula 1-1 to Chemical Formula 1-3 may be, e.g., hydrogen or a phenyl group (e.g., a substituted or unsubstituted phenyl group).

In an implementation, $R^6$ of Chemical Formula 1-4 may be, e.g., hydrogen or a phenyl group (e.g., a substituted or unsubstituted phenyl group).

In an implementation, A may be or may include, e.g., a substituted or unsubstituted biphenyl group, a substituted or unsubstituted terphenyl group, a substituted or unsubstituted fluorenyl group, a substituted or unsubstituted dibenzofuranyl group, or a substituted or unsubstituted dibenzothiophenyl group.

In an implementation, A may be a substituent of Group I.

[Group I]

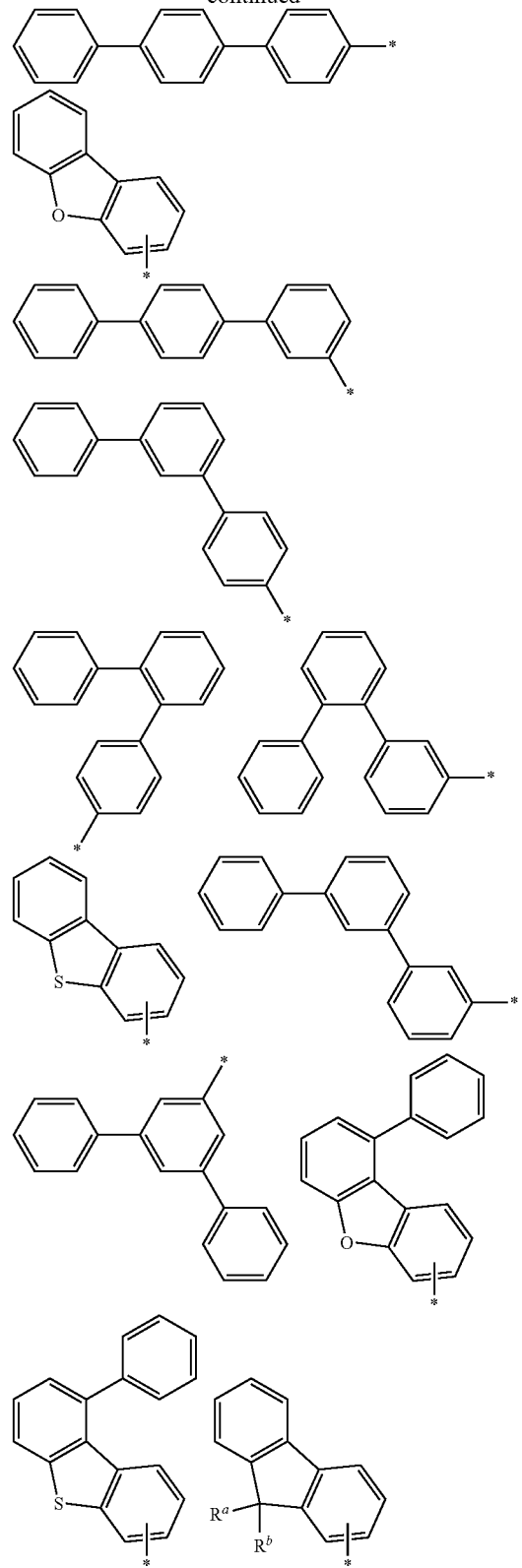

In Group I,
$R^a$ and $R^b$ may each independently be or include, e.g., a substituted or unsubstituted C1 to C6 alkyl group or a substituted or unsubstituted C6 to C12 aryl group, and * is a linking point.

In an implementation, A may be or may include, e.g., a substituted or unsubstituted biphenyl group, a substituted or unsubstituted fluorenyl group, a substituted or unsubstituted dibenzofuranyl group, or a substituted or unsubstituted dibenzothiophenyl group.

In an implementation, the compound represented by Chemical Formula 1 may be, e.g., a compound of Group 1.

[Group 1]

[A-1]

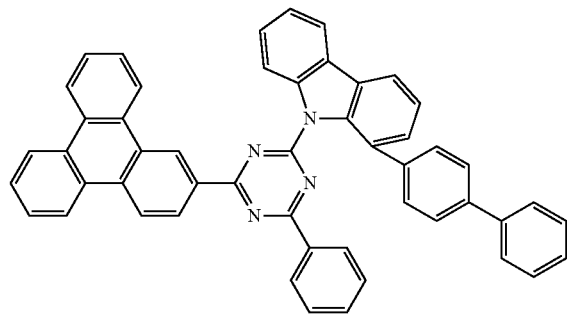

[A-2]

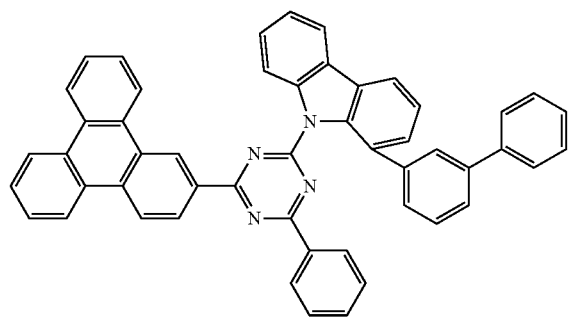

[A-3]

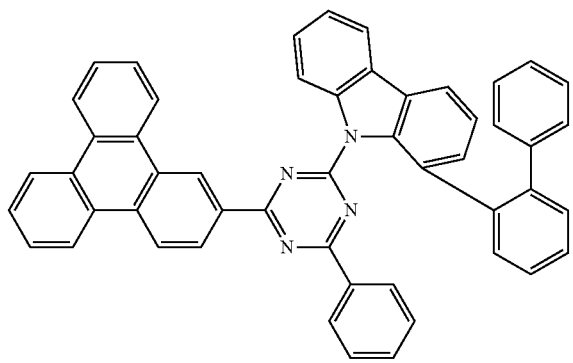

[A-4]

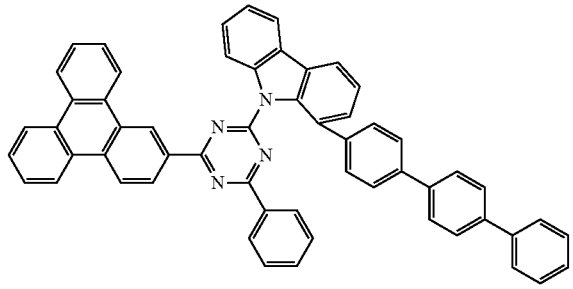

[A-5]

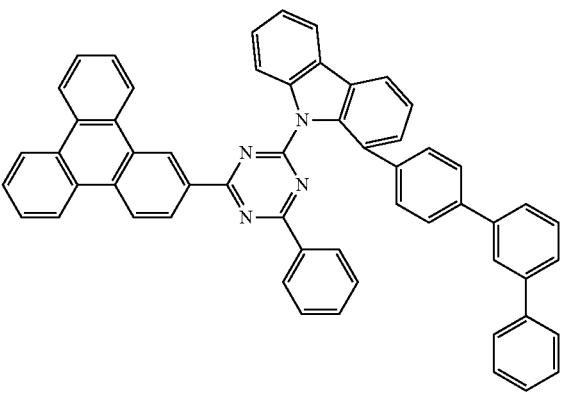

[A-6]

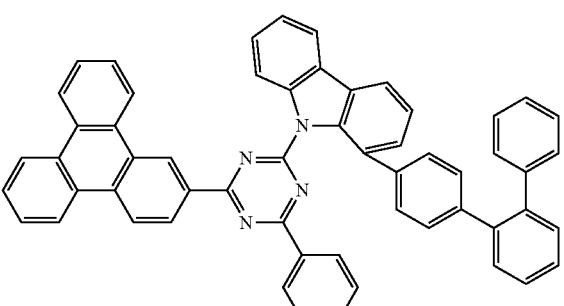

[A-7]

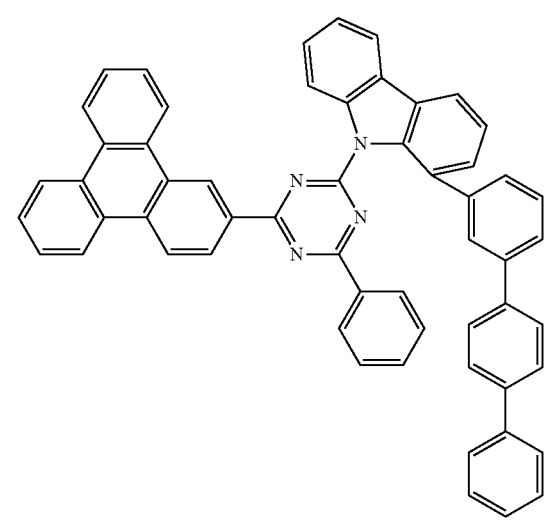

[A-8]

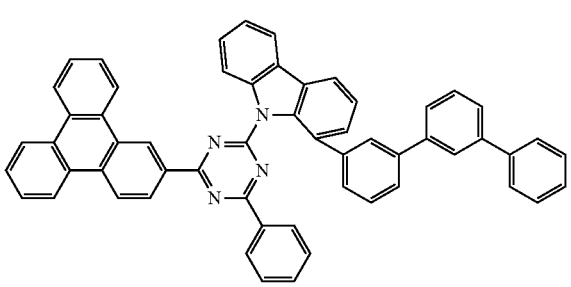

[A-9]
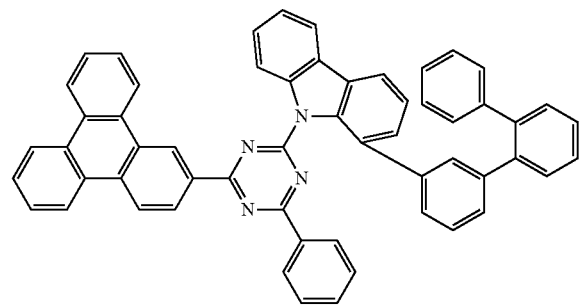
[A-10]
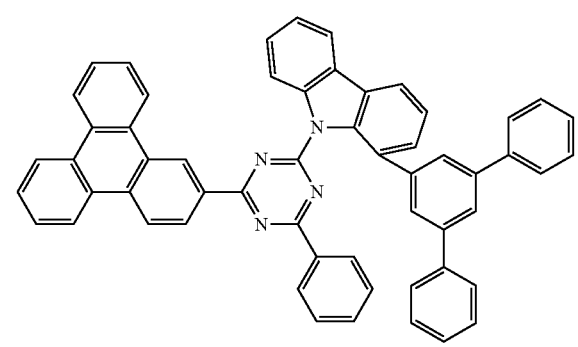
[A-11]
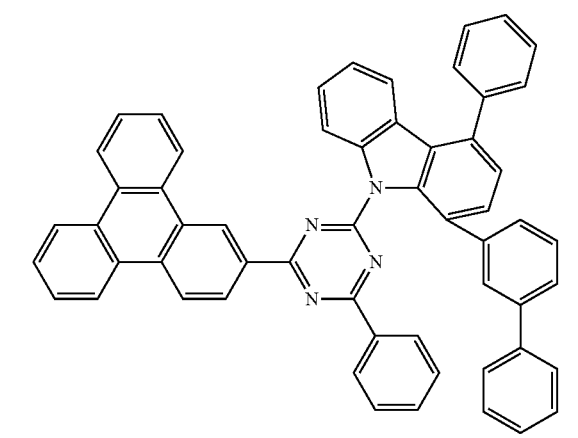
[A-12]
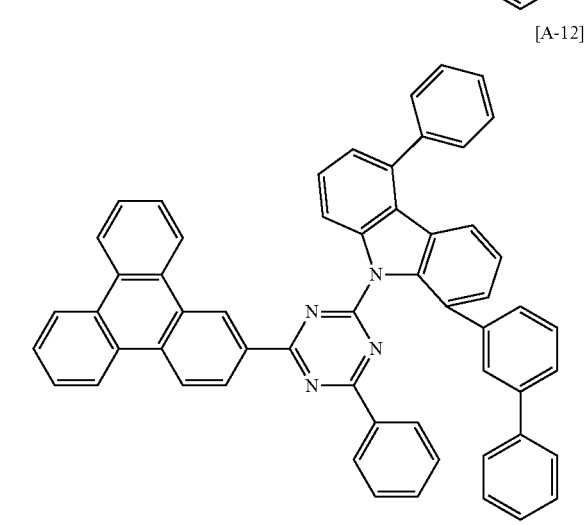
[A-13]
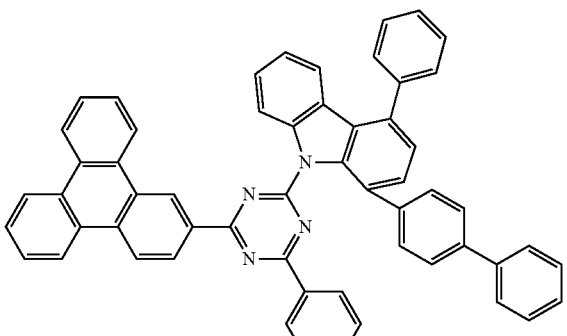
[A-14]
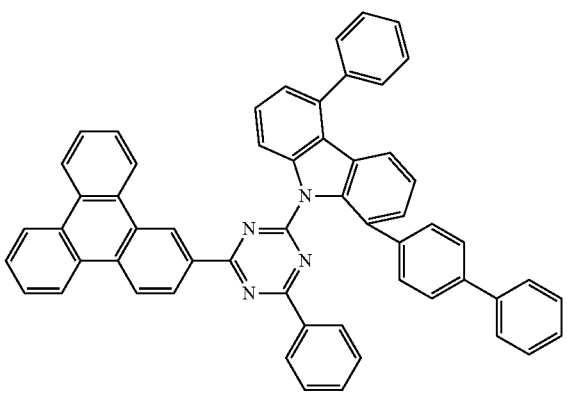
[A-15]
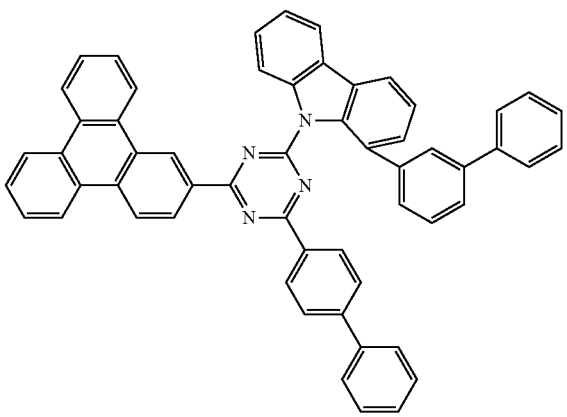
[A-16]
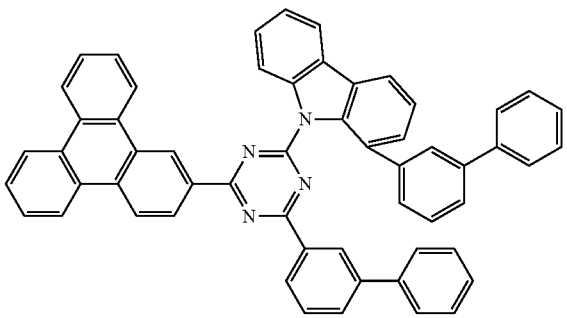

[A-17]
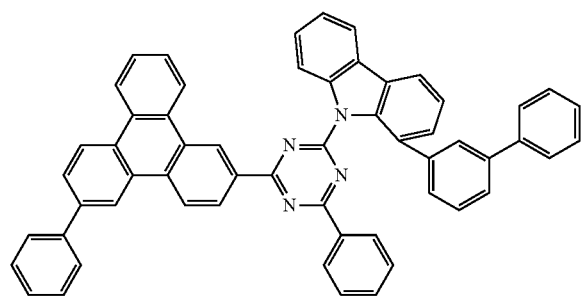
[A-21]
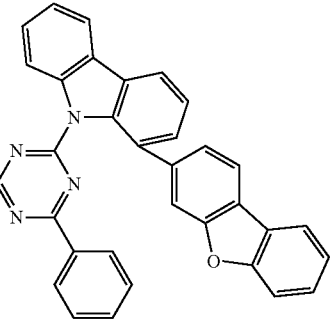
[A-18]
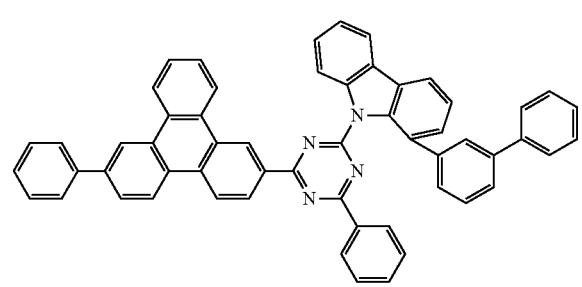
[A-22]
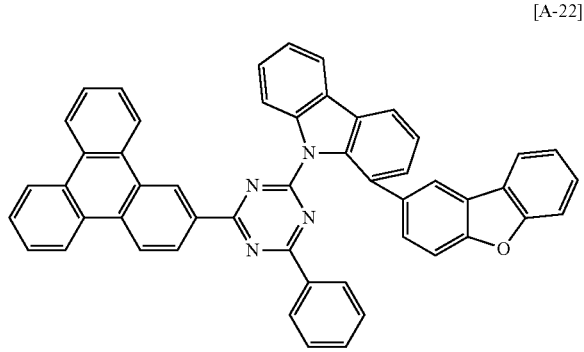
[A-19]
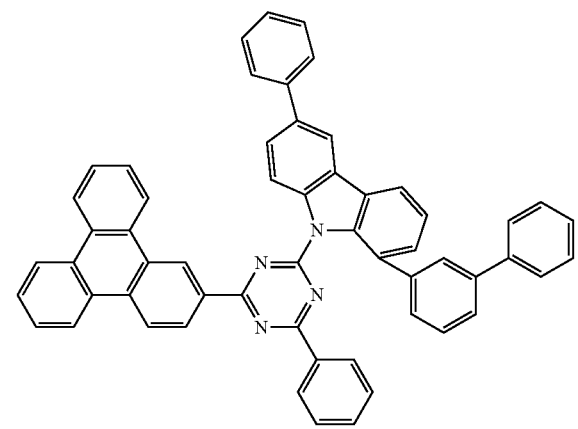
[A-23]
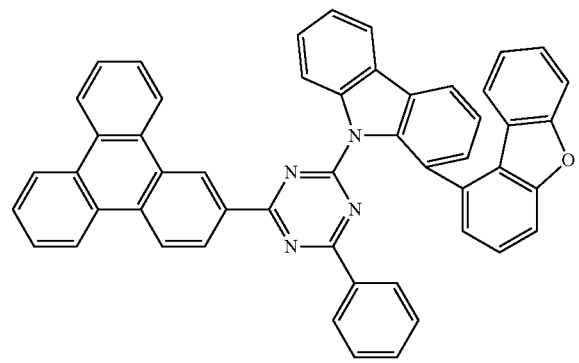
[A-20]
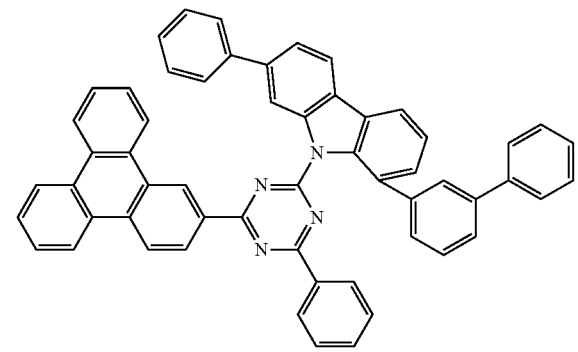
[A-24]
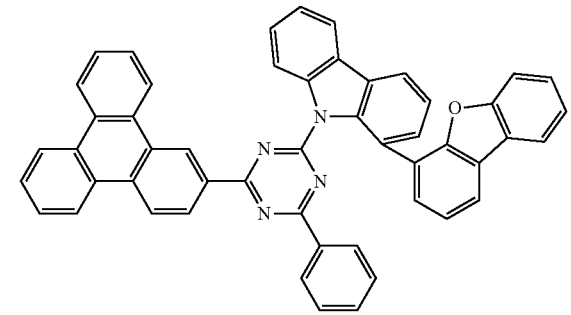

[A-25]
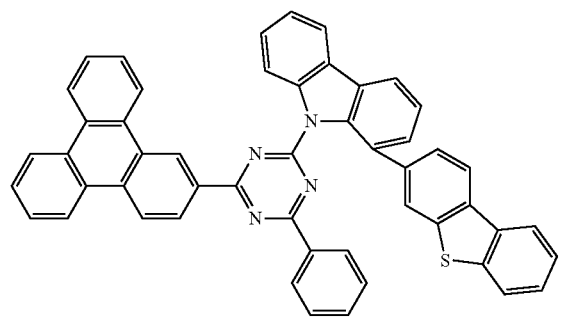
[A-29]
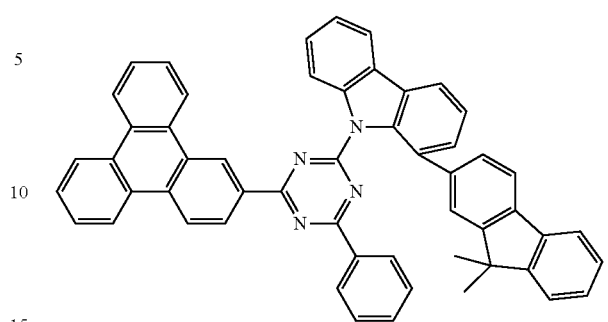
[A-26]
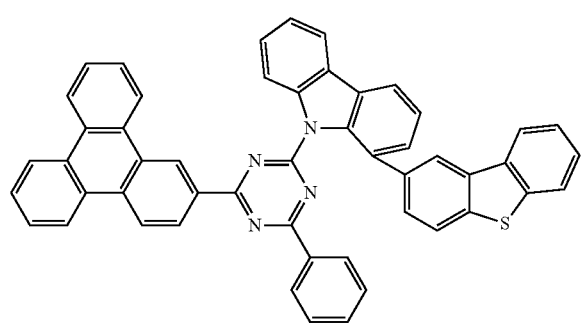
[A-30]
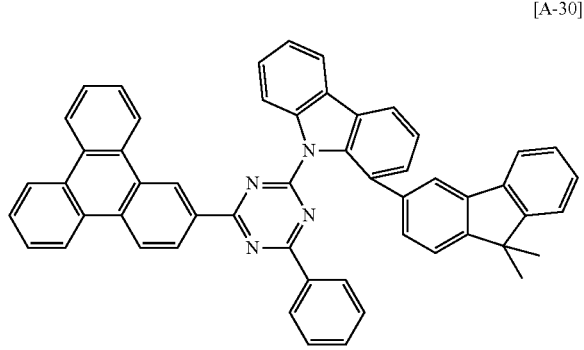
[A-27]
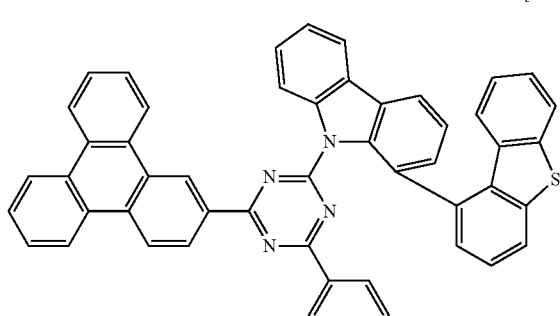
[A-31]
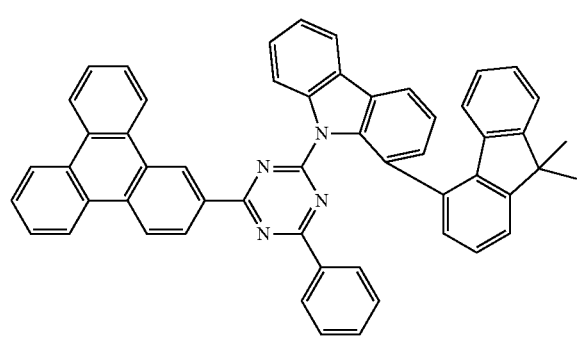
[A-28]
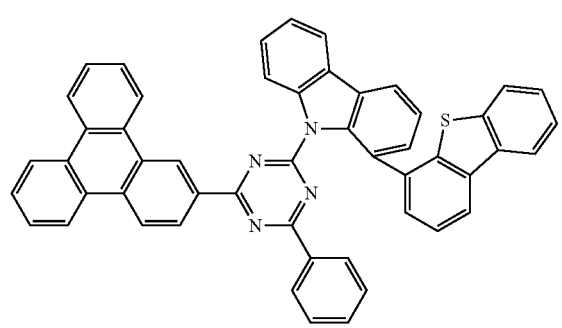
[A-32]
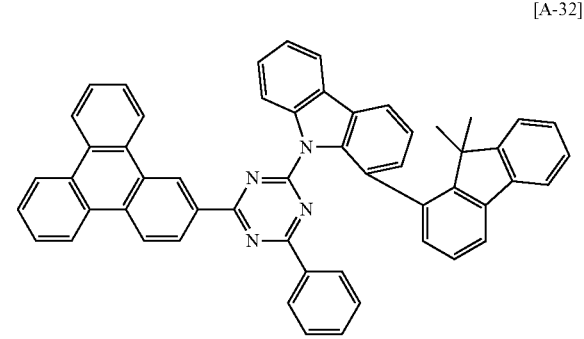

[A-33]
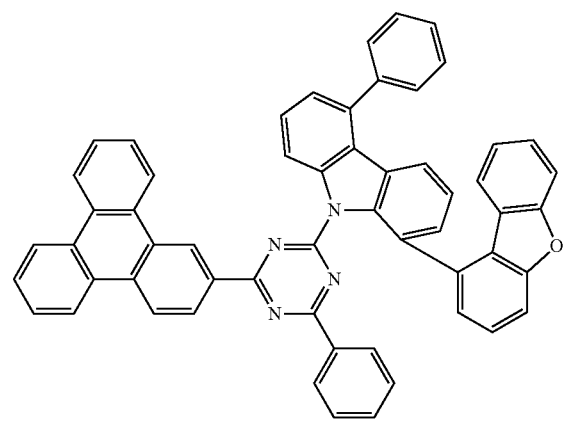

[A-34]
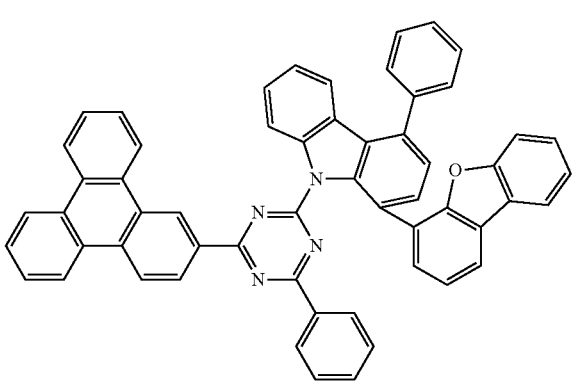

[A-35]
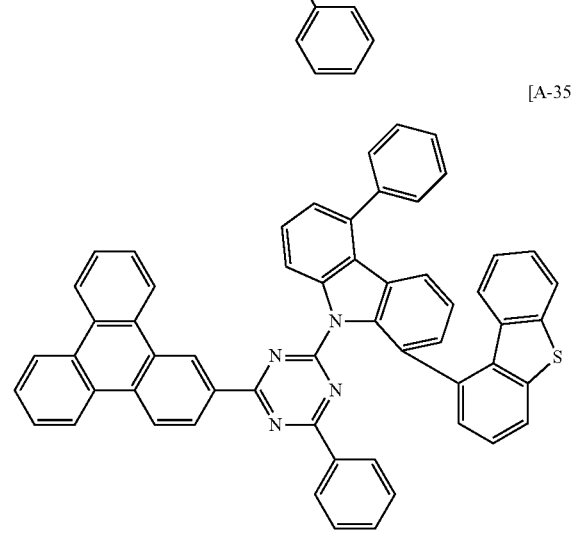

[A-36]
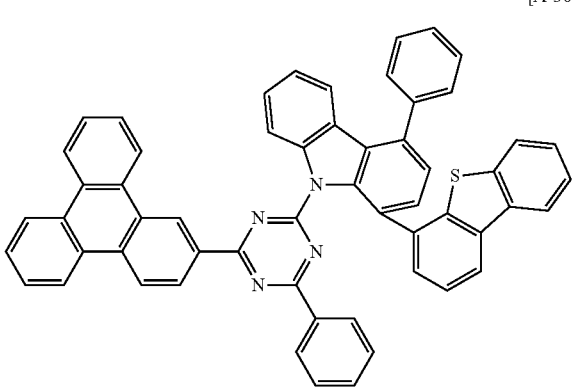

[A-37]
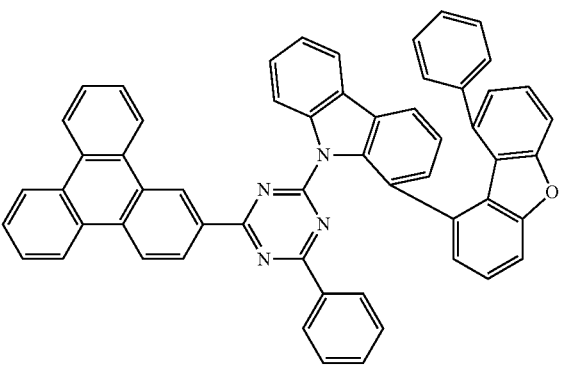

[A-38]
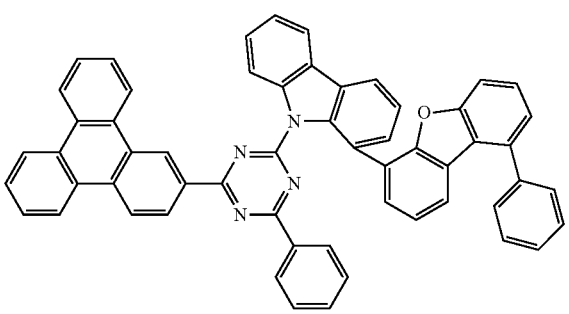

[A-39]
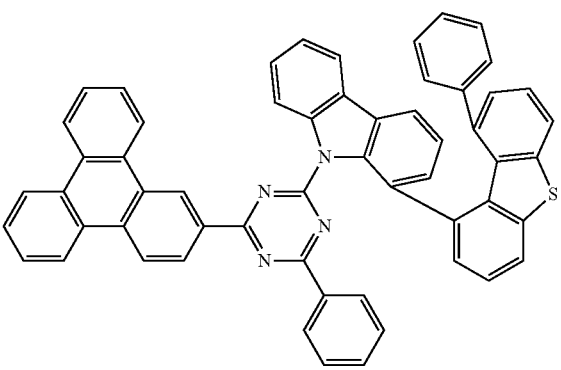

[A-40]
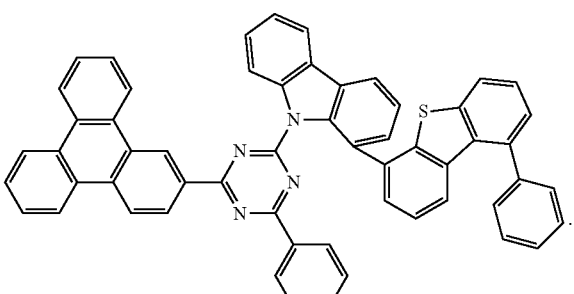

The aforementioned compound for the organic optoelectronic device may be applied in a form of a composition.

In an implementation, the compound for the organic optoelectronic device described above may be applied in a form of a composition (e.g., mixture) further including a suitable compound.

The suitable compound may be a compound having relatively strong hole characteristics compared with the aforementioned compound for the organic optoelectronic device, and may be, e.g., a compound including at least one of a carbazole moiety and an amine moiety.

The suitable compound may be, e.g., 9,9'-di(biphenyl-4-yl)-9H,9'H-3,3'-bicarbazole, or may be appropriately selected from suitable compounds and applied.

In an implementation, the composition may further include a dopant. The dopant may be, e.g., a phosphorescent dopant. The phosphorescent dopant may be, e.g., a red, green, or blue phosphorescent dopant. The phosphorescent dopant may be, e.g., a red or green phosphorescent dopant.

The dopant may be a material mixed in a small amount to facilitate light emission and generally a material such as a metal complex that emits light by multiple excitation into a triplet or more. The dopant may be, e.g. an inorganic, organic, or organic/inorganic compound, and one or more types thereof may be used.

Examples of the dopant may include a phosphorescent dopant and examples of the phosphorescent dopant may include an organometal compound including Ir, Pt, Os, Ti, Zr, Hf, Eu, Tb, Tm, Fe, Co, Ni, Ru, Rh, Pd, or a combination thereof. The phosphorescent dopant may be, e.g., a compound represented by Chemical Formula Z.

LMX                              [Chemical Formula Z]

In Chemical Formula Z, M may be a metal, L and X may each independently be ligands that form a complex compound with M.

The M may be, e.g., Ir, Pt, Os, Ti, Zr, Hf, Eu, Tb, Tm, Fe, Co, Ni, Ru, Rh, Pd, or a combination thereof, and L and X may be, e.g., bidentate ligands.

The compound for the organic optoelectronic device may be formed by a dry film forming method such as chemical vapor deposition.

Hereinafter, an organic optoelectronic device to which the aforementioned compound for the organic optoelectronic device is applied is described.

The organic optoelectronic device may be a suitable device to convert electrical energy into photoenergy and vice versa, e.g., an organic photoelectric device, an organic light emitting diode, an organic solar cell, and an organic photoconductor drum.

Herein, an organic light emitting diode as one example of an organic optoelectronic diode is described referring to drawings.

Figure 2:
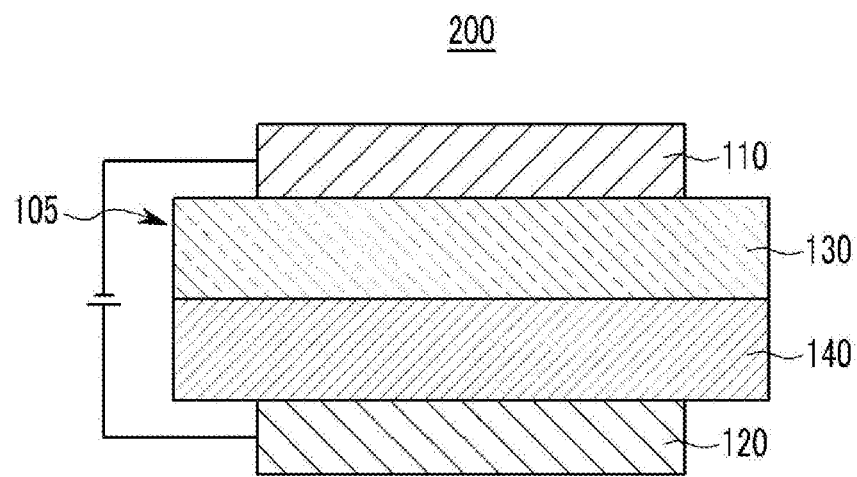

FIGS. 1 and 2 are cross-sectional views showing organic light emitting diodes according to embodiments.

Referring to FIG. 1, an organic light emitting diode 100 according to an embodiment may include an anode 120 and a cathode 110 facing each other and an organic layer 105 between the anode 120 and the cathode 110.

The anode 120 may be a conductor having a large work function to facilitate hole injection, and may include, e.g., a metal, a metal oxide, and/or a conductive polymer. The anode 120 may include, e.g., a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy) thiophene) (PEDOT), polypyrrole, and polyaniline.

The cathode 110 may be a conductor having a small work function to facilitate electron injection, and may include, e.g., a metal, a metal oxide and/or a conductive polymer. The cathode 110 may include, e.g., a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, $LiO_2$/Al, LiF/Ca, and $BaF_2$/Ca.

The organic layer 105 may include a light emitting layer 130 including the aforementioned compound or composition.

The light emitting layer 130 may include, e.g., the aforementioned compound or composition.

Referring to FIG. 2, an organic light emitting diode 200 may further include a hole auxiliary layer 140 in addition to the light emitting layer 130. The hole auxiliary layer 140 may further increase hole injection and/or hole mobility and may block electrons between the anode 120 and the light emitting layer 130. The hole auxiliary layer 140 may be, e.g., a hole transport layer, a hole injection layer, and/or an electron blocking layer and may include at least one layer.

The hole auxiliary layer 140 may include, e.g., a compound of Group A, below.

In an implementation, the hole auxiliary layer 140 may include a hole transport layer between the anode 120 and the light emitting layer 130, and a hole transport auxiliary layer between the light emitting layer 130 and the hole transport layer and at least one of the compounds of Group A may be included in the hole transport auxiliary layer.

[Group A]

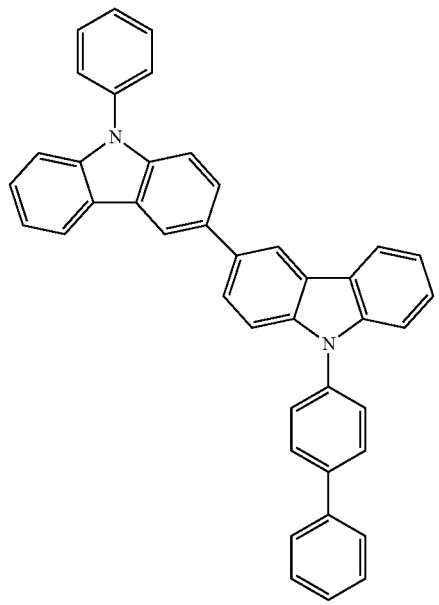

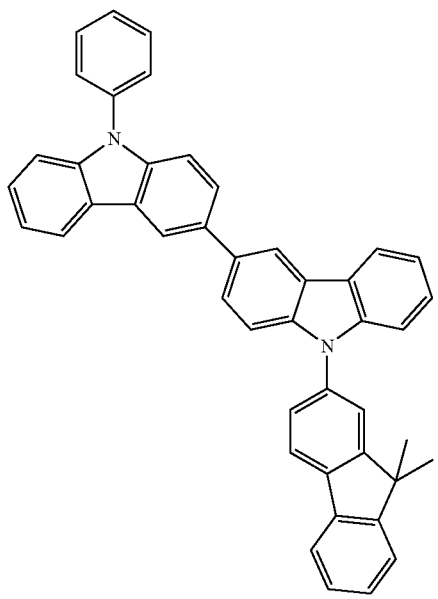
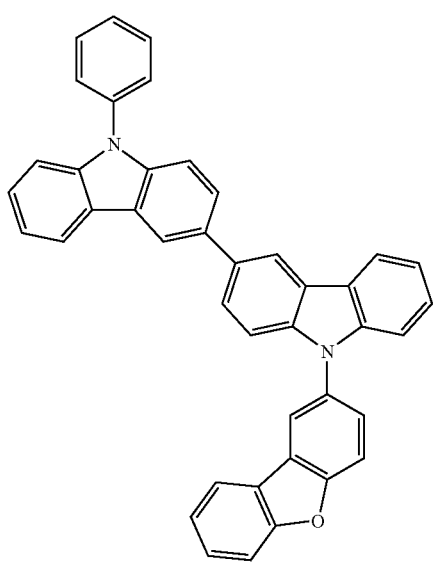
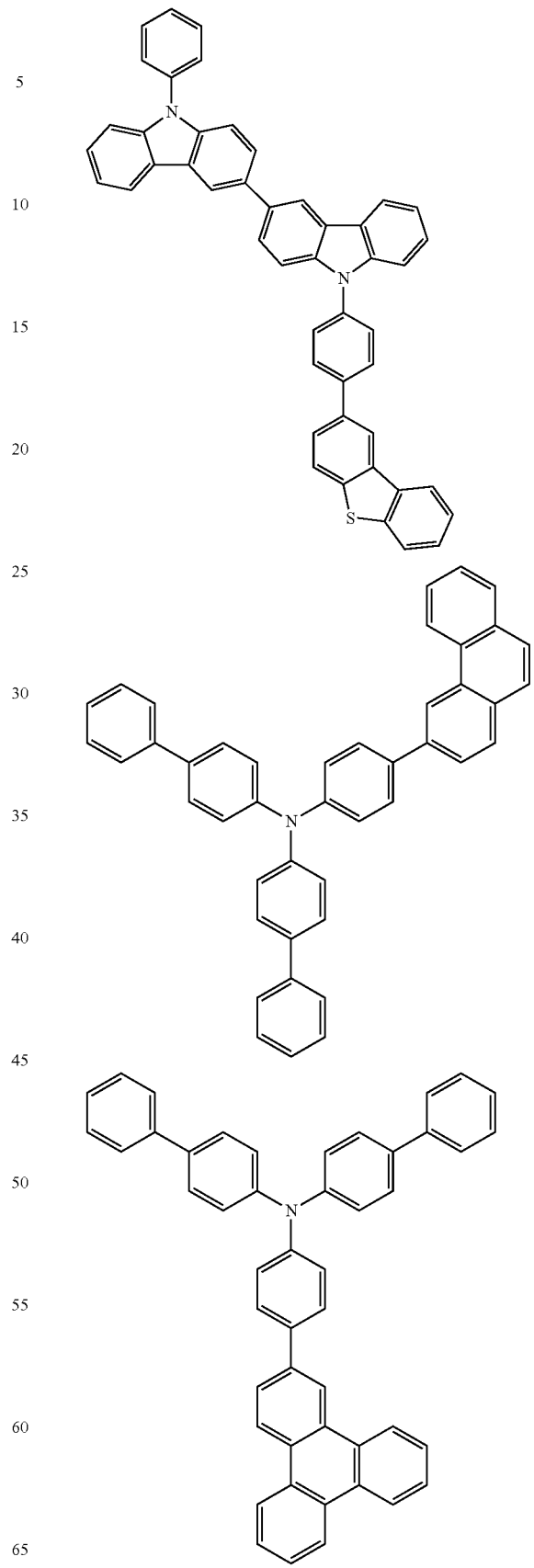

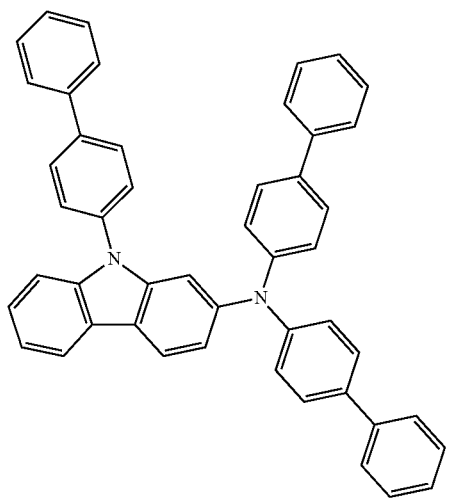
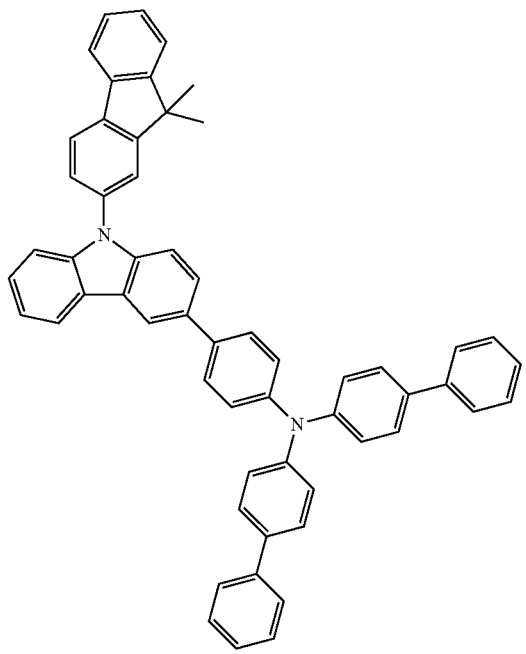
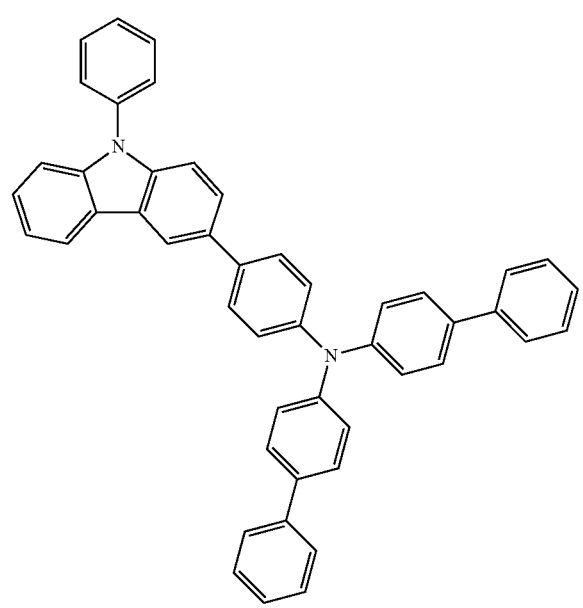
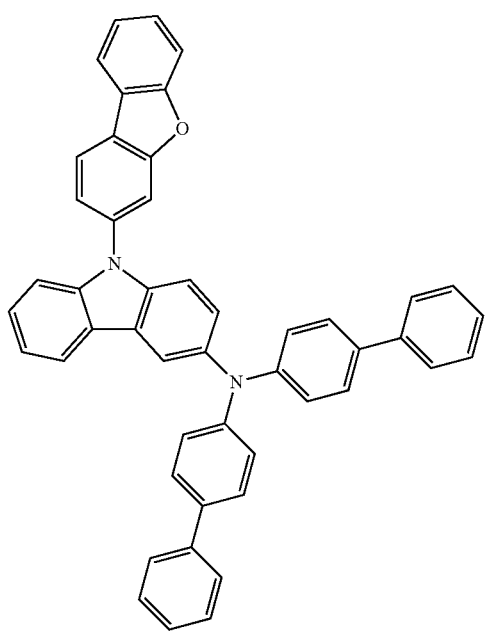

37
-continued
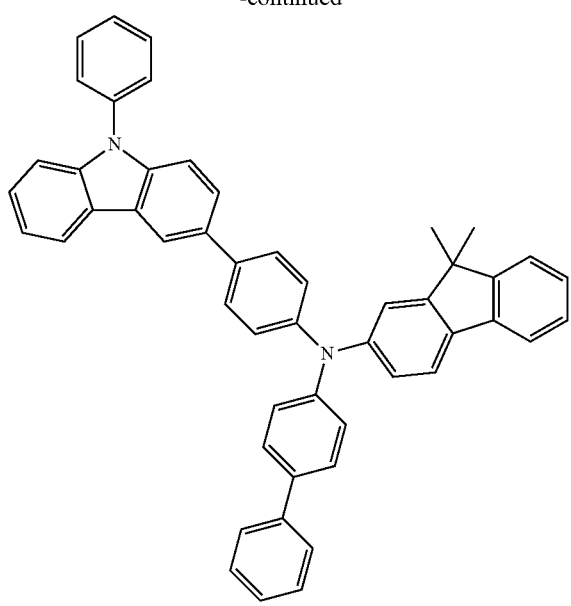
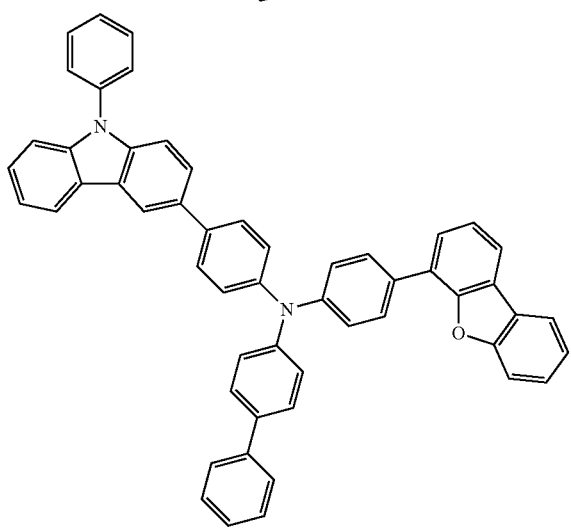
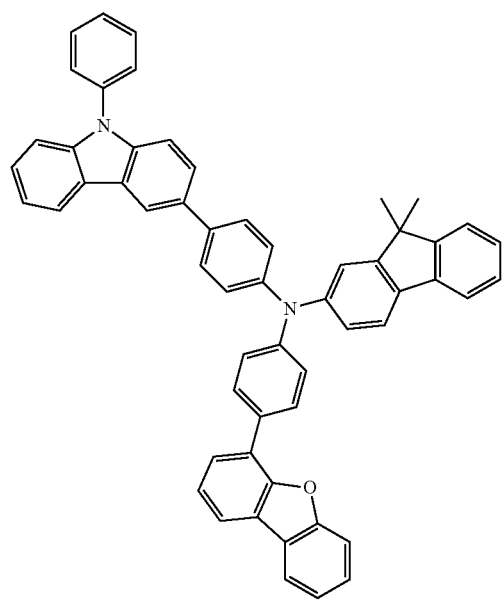
38
-continued
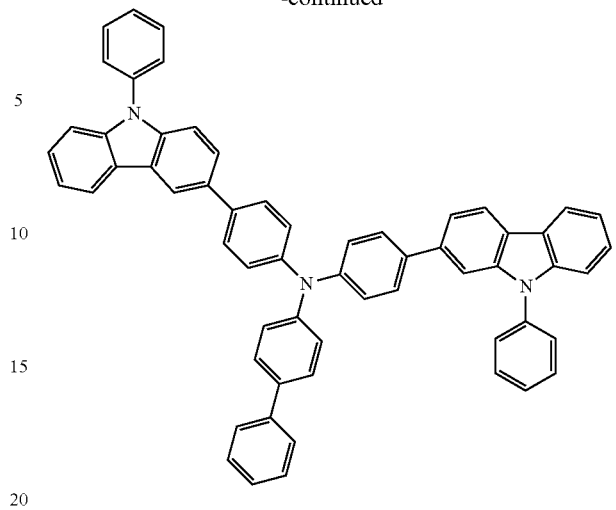
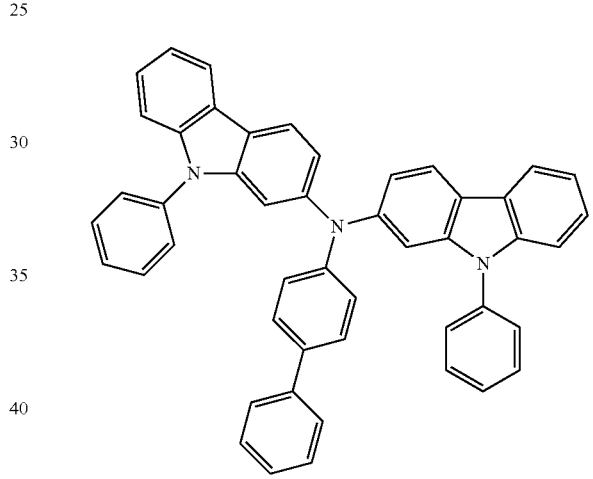
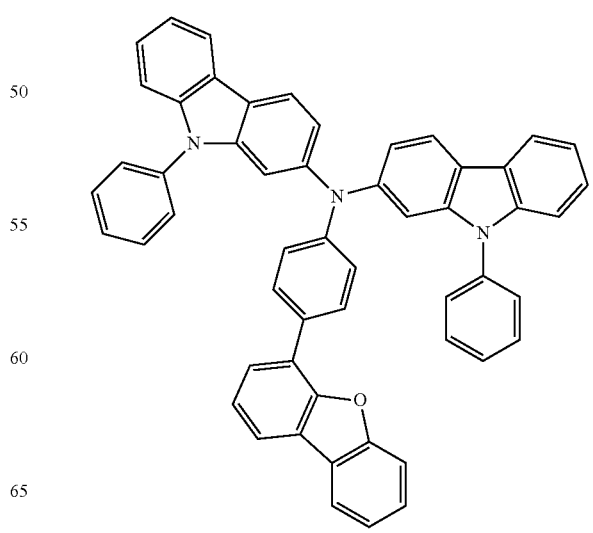

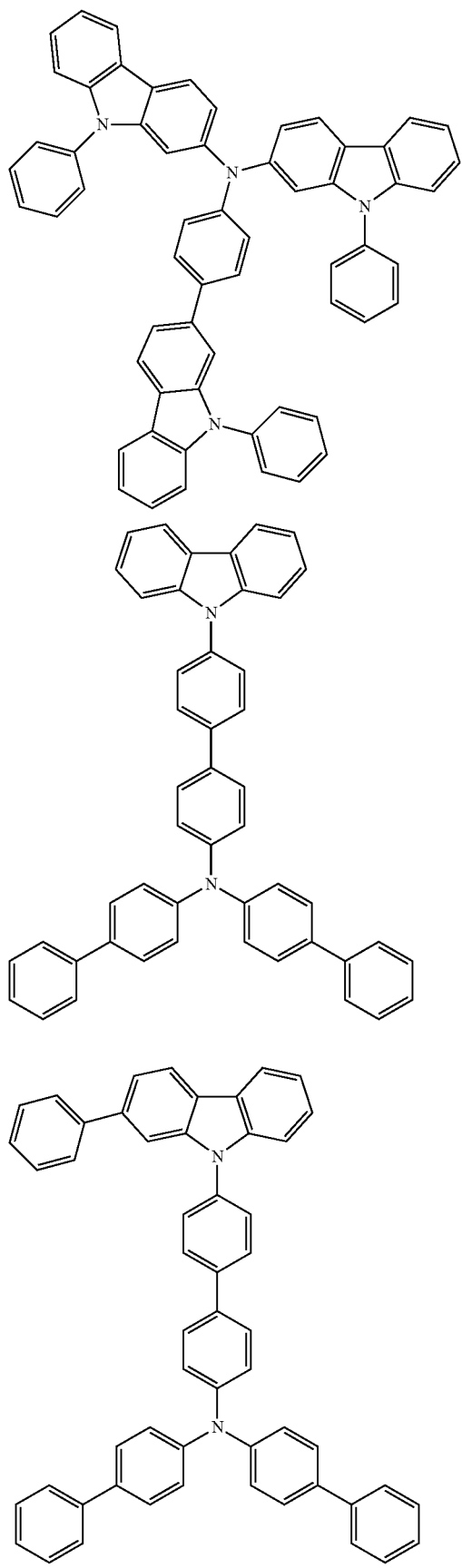
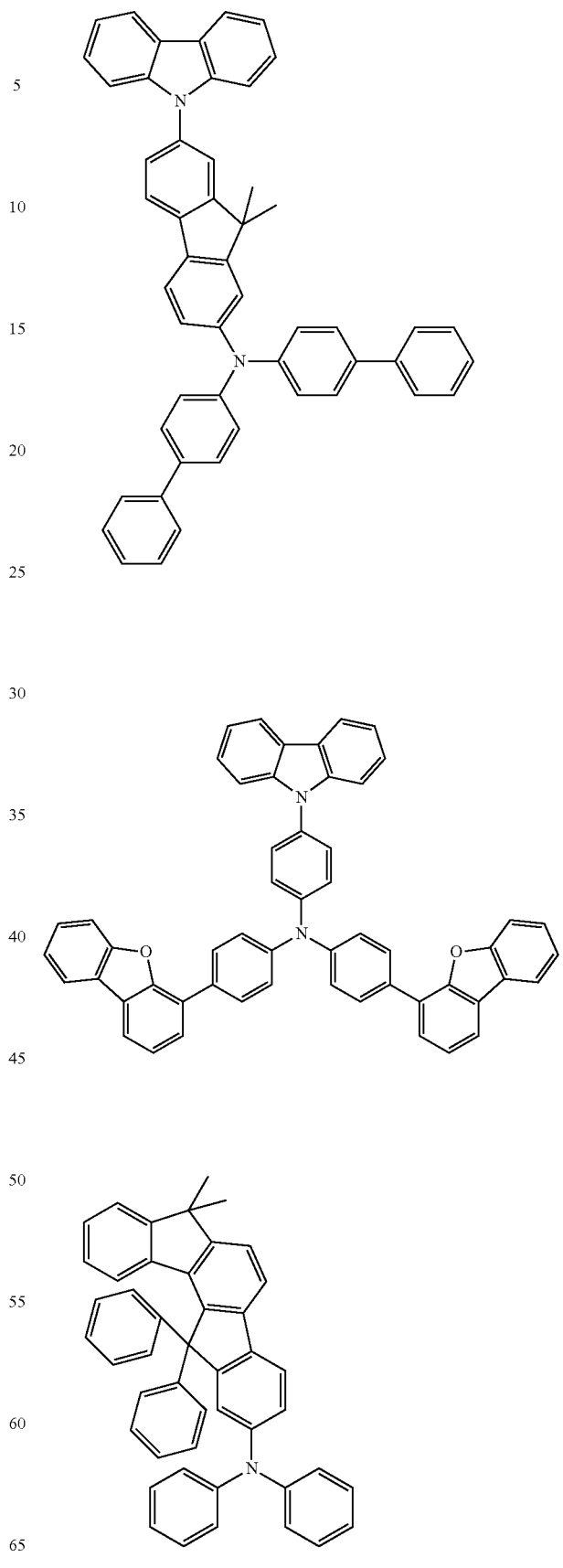

41
-continued
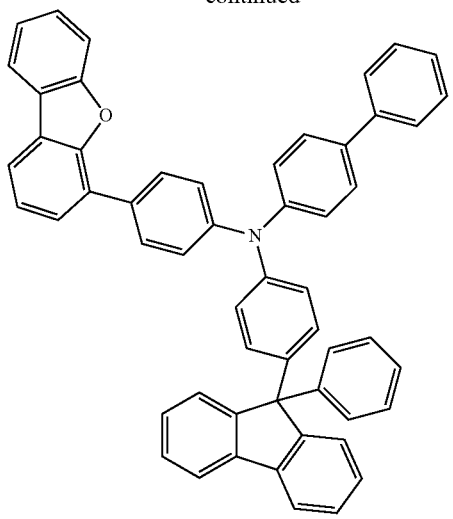
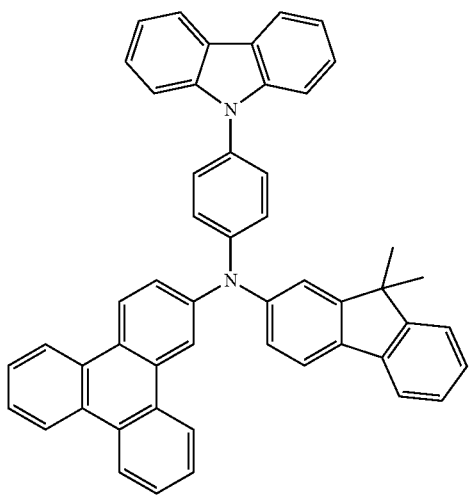
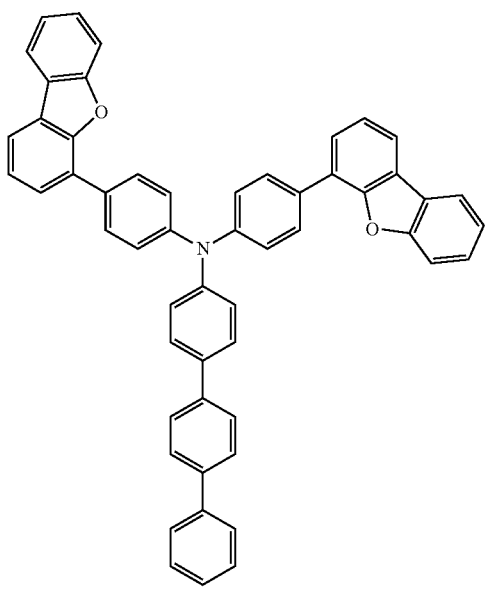
42
-continued
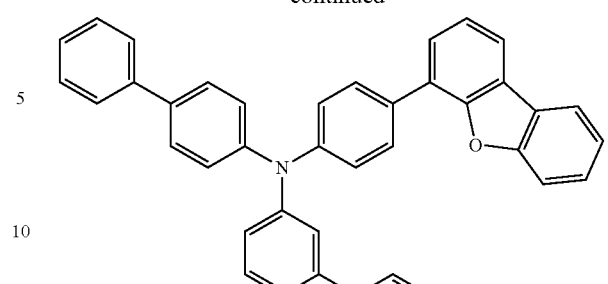
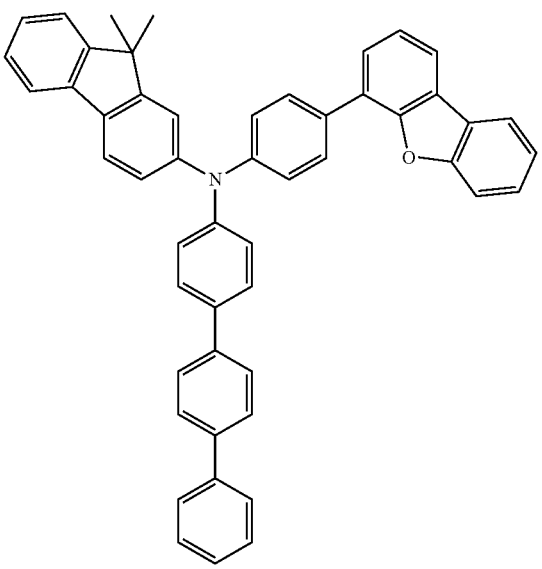
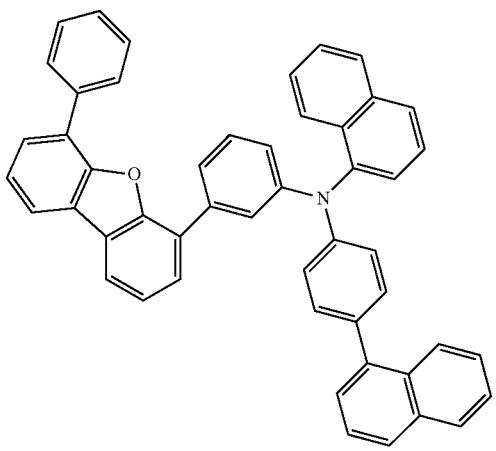

43
-continued
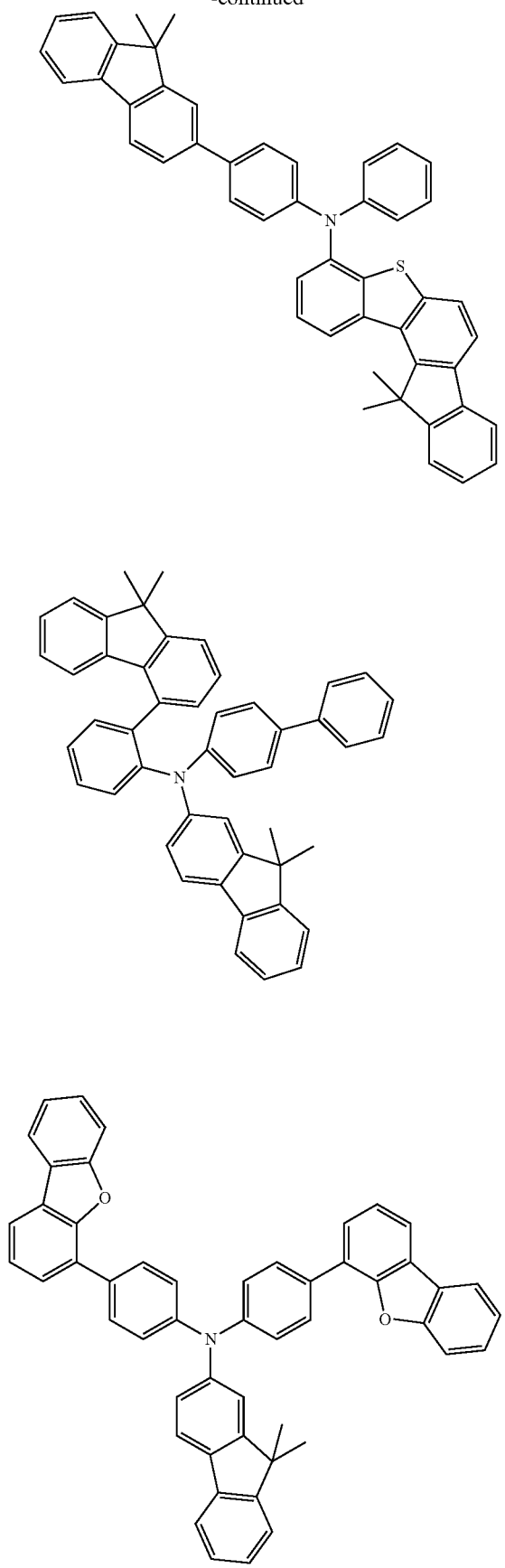
44
-continued
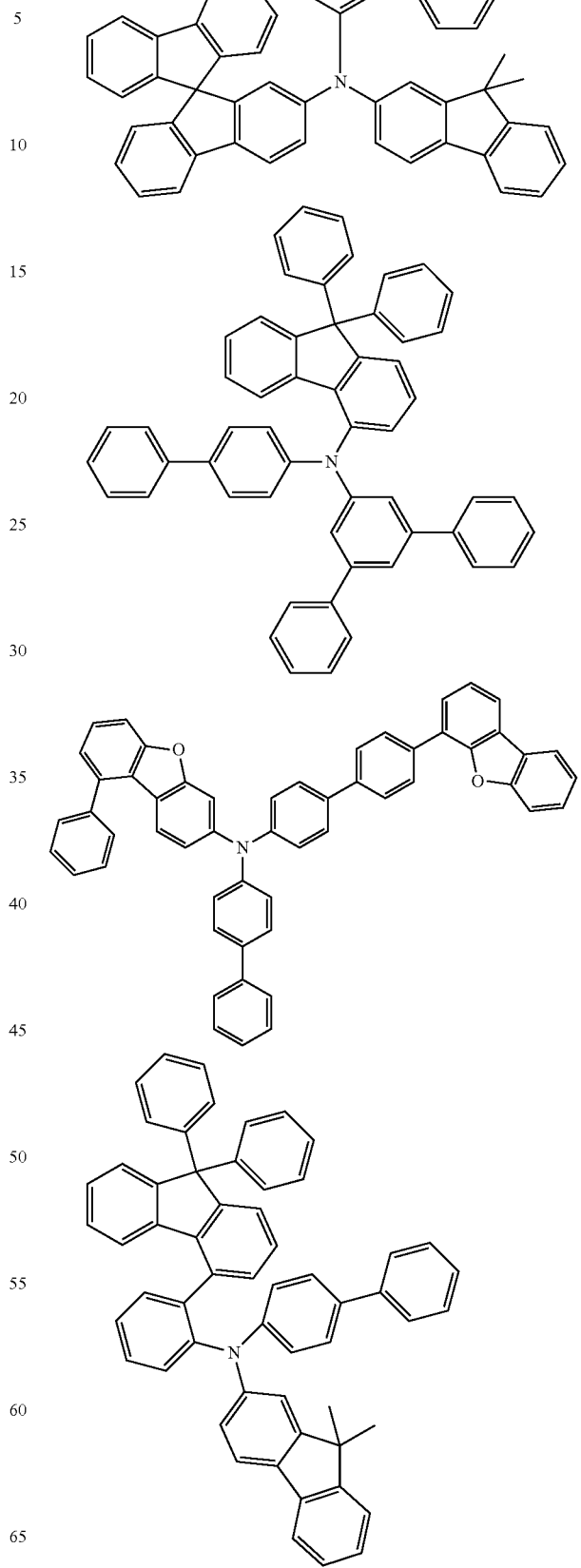

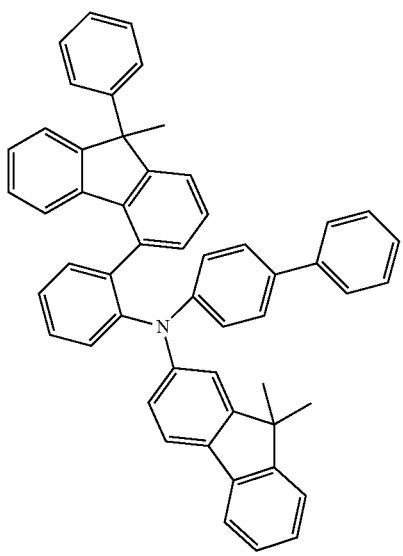
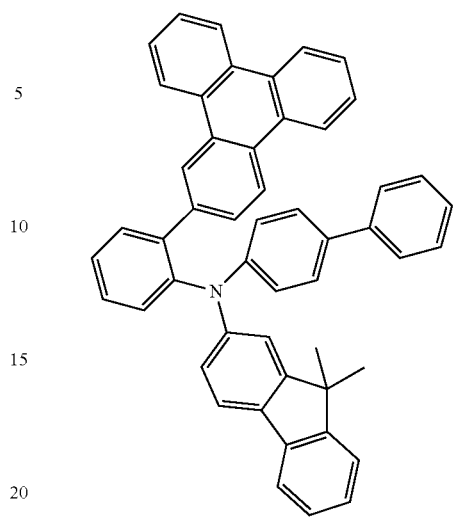
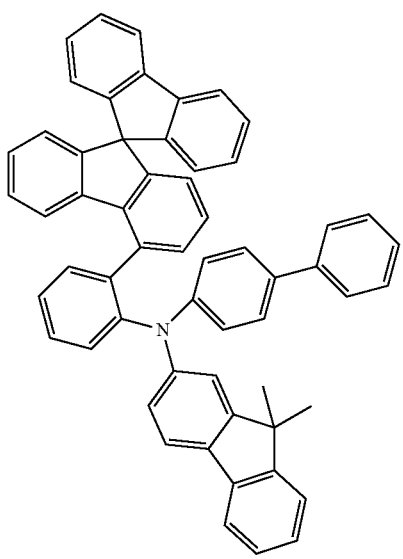
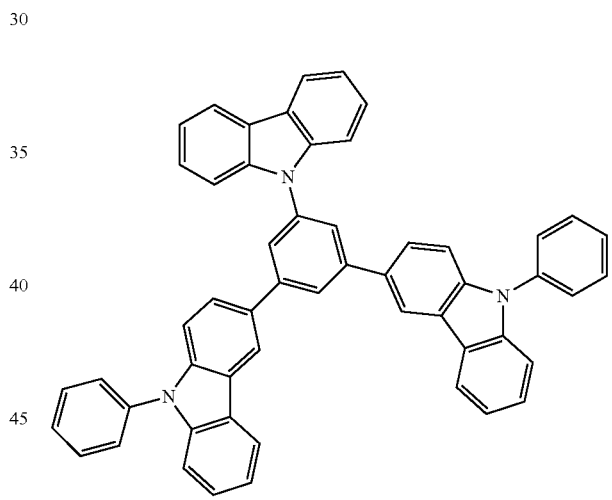
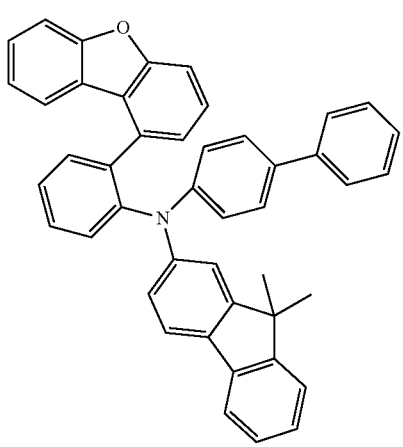
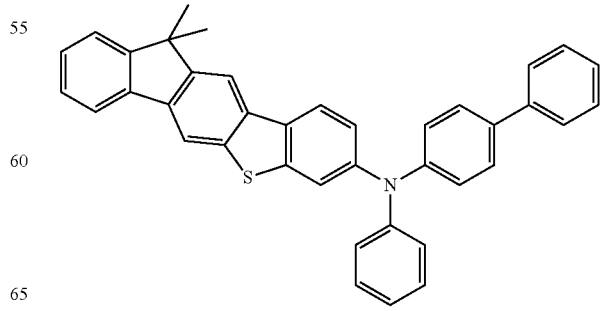

47
-continued
48
-continued
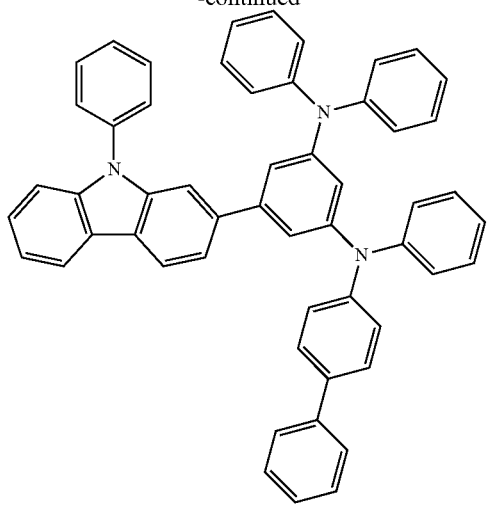
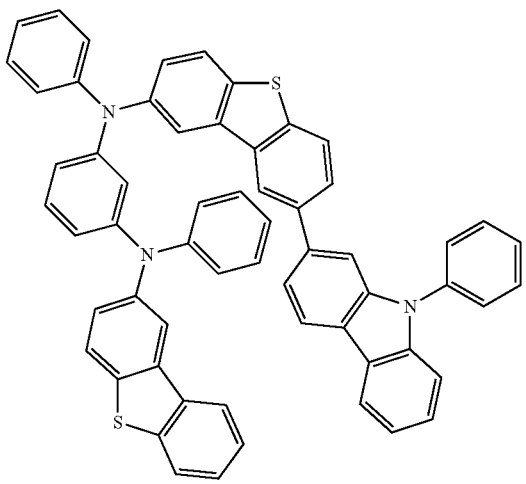
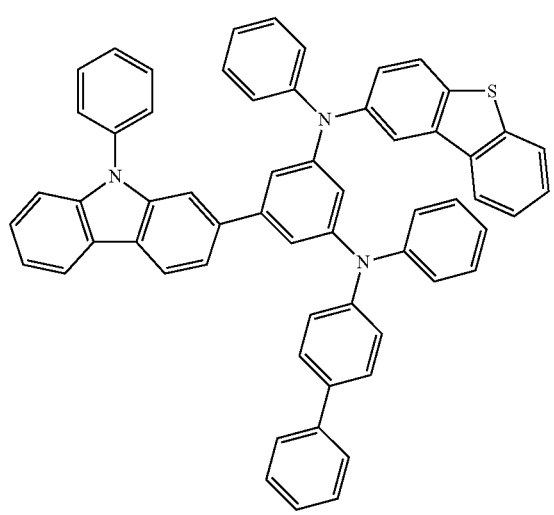
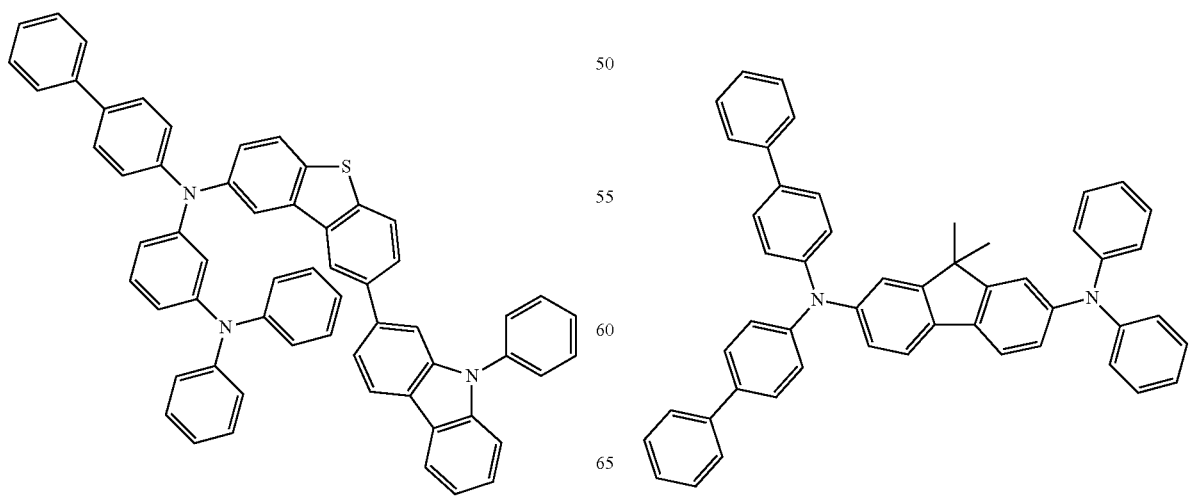

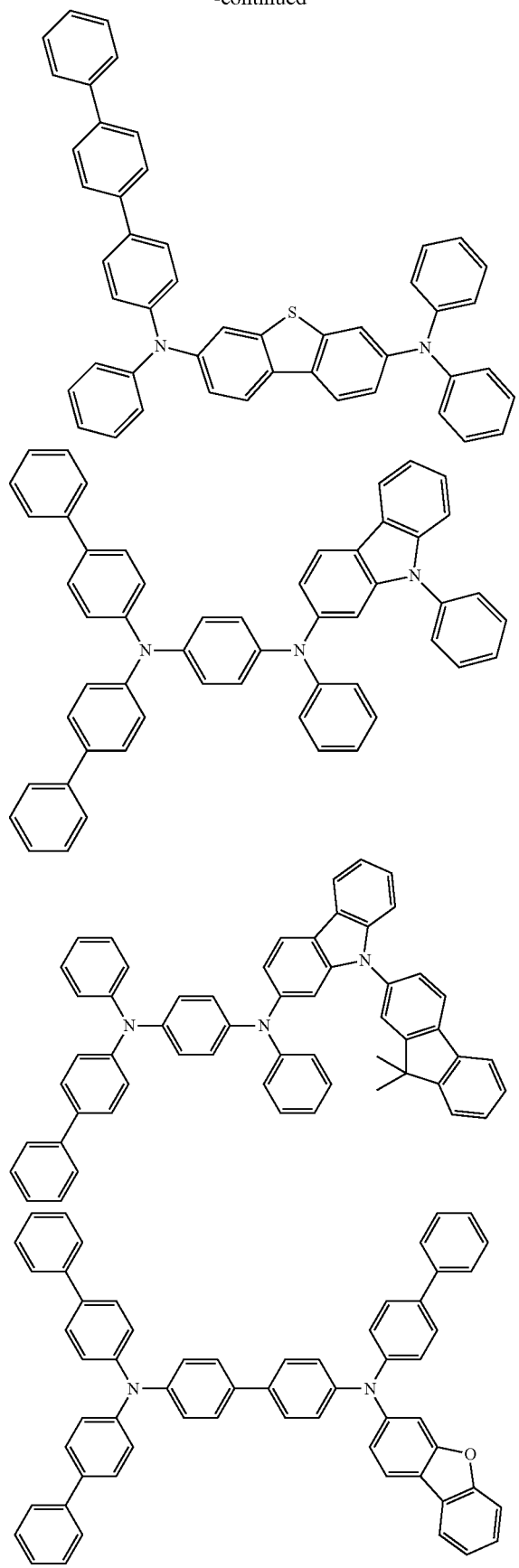
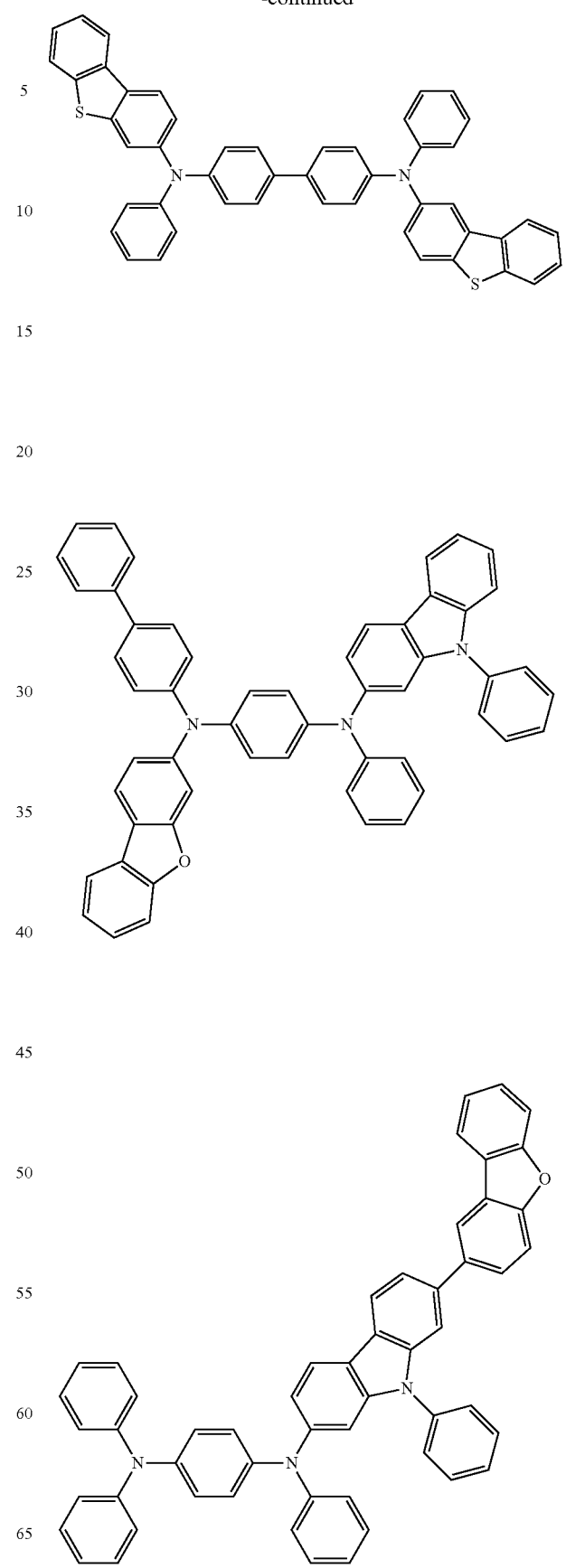

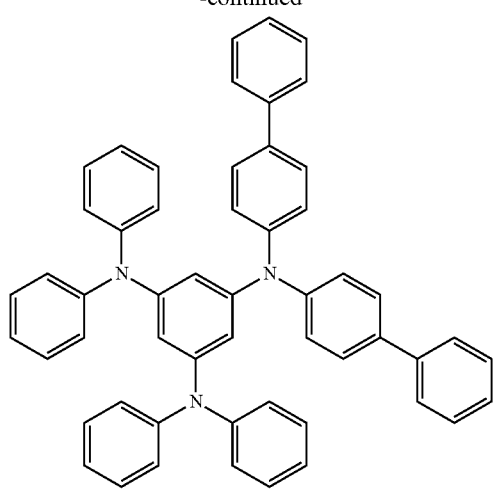
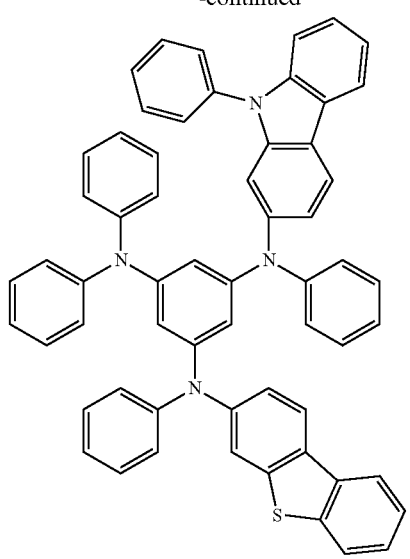
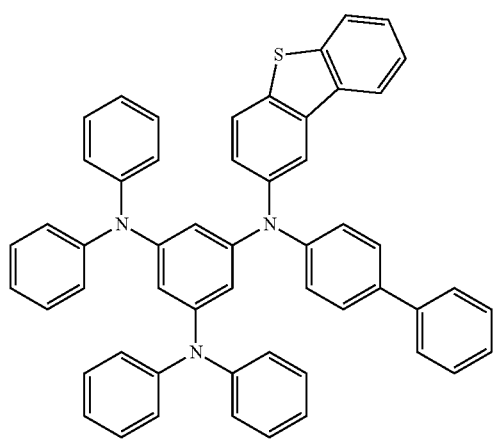
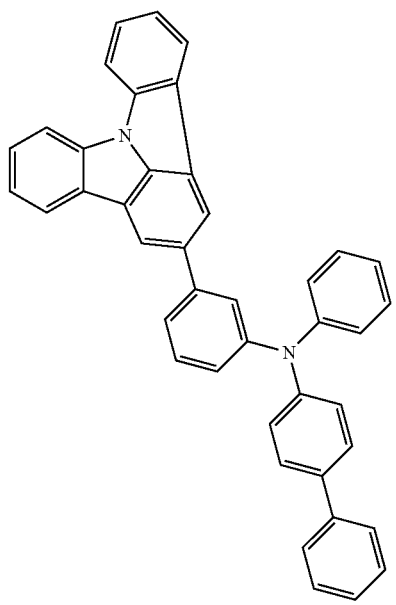
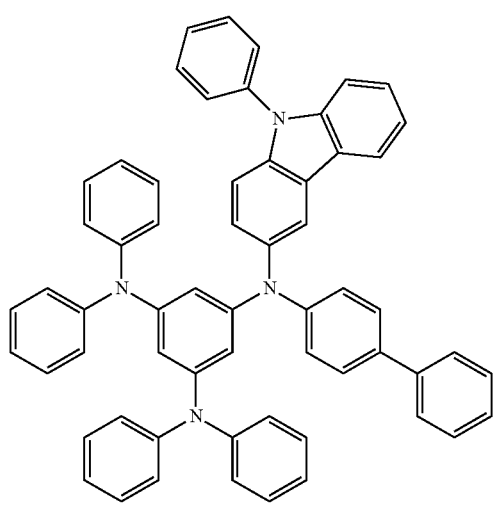
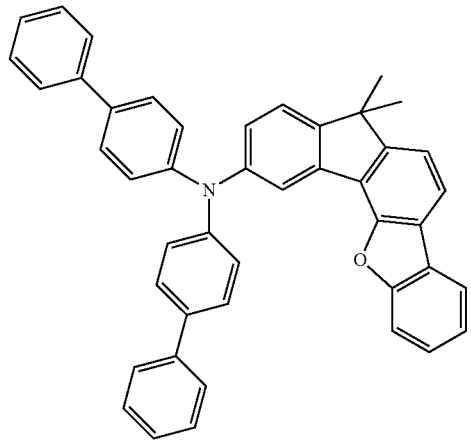

53
-continued
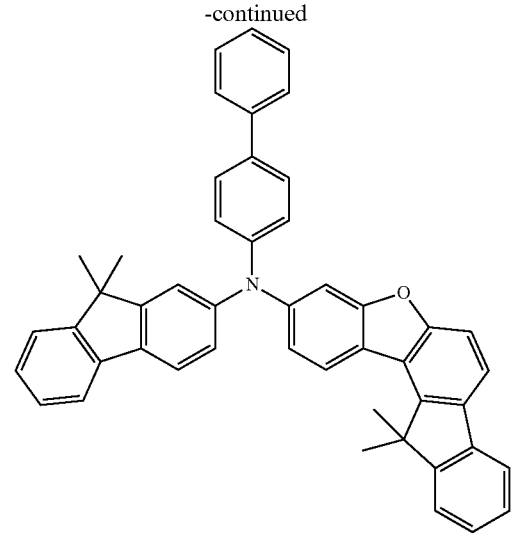
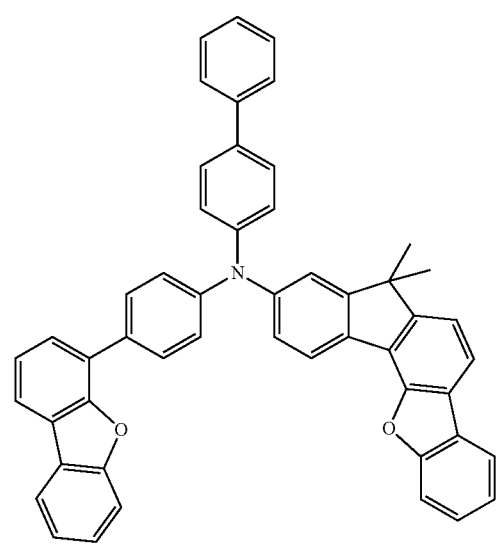
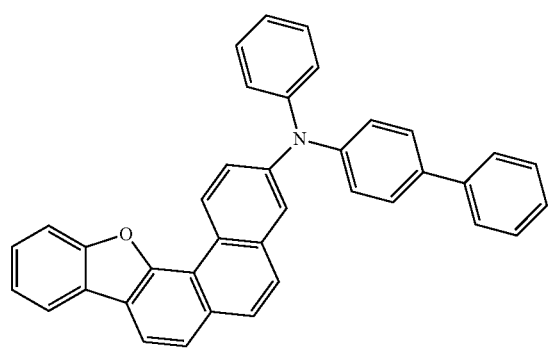
54
-continued
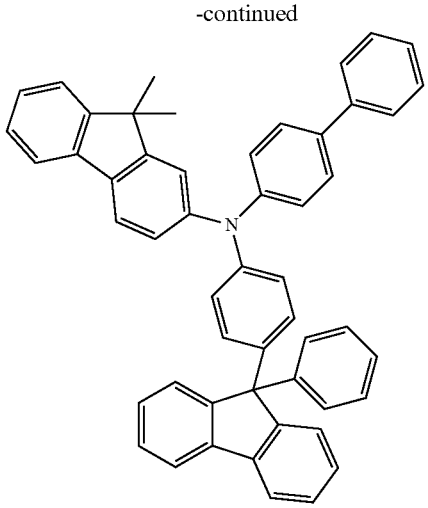
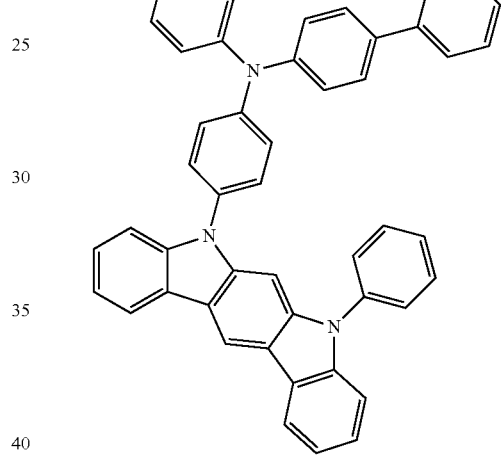
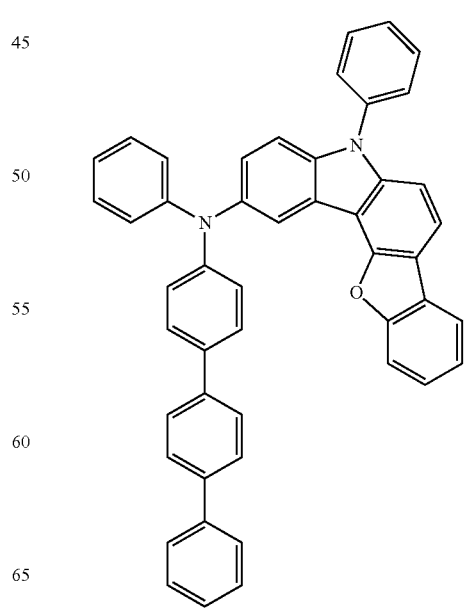

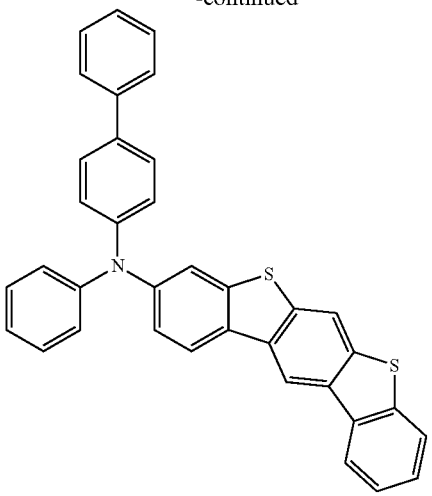

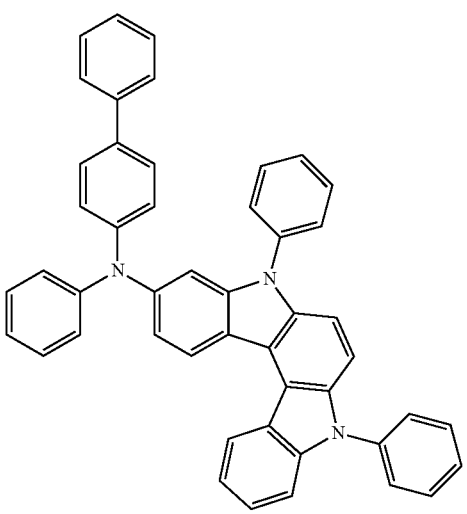

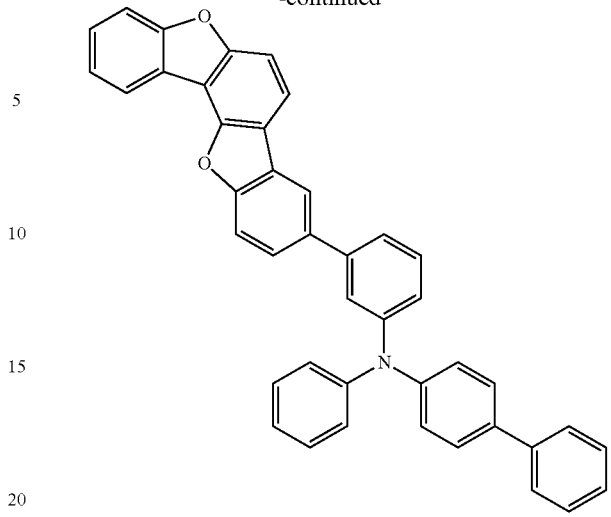

Other suitable compounds may be used for the hole transport auxiliary layer in addition to the aforementioned compound.

In an implementation, the organic light emitting diode may further include an electron transport layer, an electron injection layer, and a hole injection layer in the organic layer.

The organic light emitting diodes 100 and 200 may be produced by forming an anode or a cathode on a substrate, forming an organic layer by a dry film-forming method such as evaporation, sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, the starting materials and reactants used in examples and synthesis examples are purchased from Sigma-Aldrich, TCI, Tokyo chemical industry, or P&H tech or synthesized through a known method, unless otherwise specified. It was purchased or synthesized through a known method.

Preparation of Compound for Organic Optoelectronic Device

Synthesis Example 1: Synthesis of Intermediate I-1

[Reaction Scheme 1]

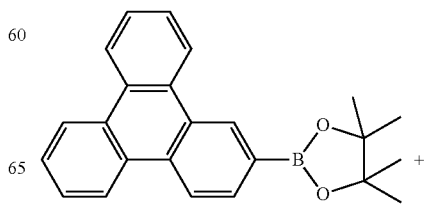

-continued

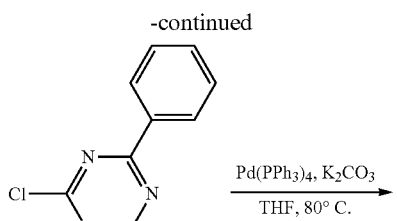

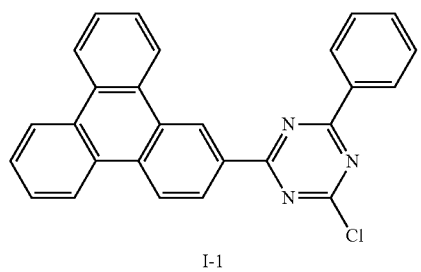

I-1

4,4,5,5-tetramethyl-2-(triphenylen-2-yl)-1,3,2-dioxaborolane (100 g, 282 mmol) purchased from P&H Tech Co., Ltd. (http://www.phtech.co.kr/) was dissolved in 0.1 L of tetrahydrofuran (THF) under a nitrogen atmosphere, and 2,4-dichloro-6-phenyl-1,3,5-triazine (95.7 g, 423 mmol) purchased from Tokyo Chemical Industry Co., Ltd. (http://www.tcichemicals.com/) and tetrakis(triphenylphosphine) palladium (2.72 g, 2.86 mmol) were added thereto and then, stirred. Subsequently, potassium carbonate saturated in water (97.4 g, 705 mmol) was added thereto and then, heated and refluxed at 80° C. for 8 hours. When a reaction was complete, water was added to the reaction solution, and the mixture was extracted with dichloromethane (DCM), treated with anhydrous magnesium sulfate to remove moisture, filtered, and concentrated under a reduced pressure. The obtained residue was separated and purified through flash column chromatography to obtain Intermediate I-1 (76.6 g, 65%).

HRMS (70 eV, EI+): m/z calcd for C27H16C1N3: 417.1033, found: 417.

Elemental Analysis: C, 78%; H, 4%

Synthesis Example 2: Synthesis of Intermediate 1-2

[Reaction Scheme 2]

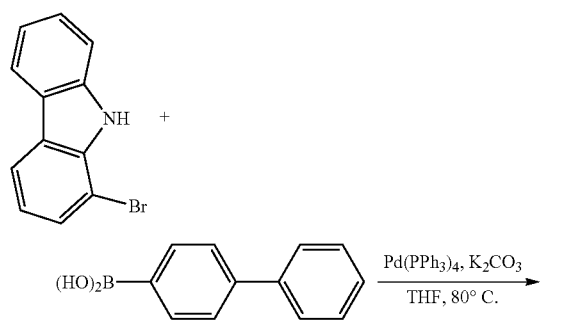

-continued

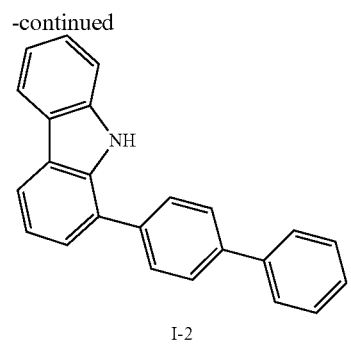

I-2

Intermediate 1-2 (32.3 g, 83%) was obtained according to the same method as Synthesis Example 1 except that 1-bromocarbazole (30 g, 122 mmol) purchased from Tokyo Chemical Industry Co., Ltd. and biphenyl-4-ylboronic acid (26.6 g, 134 mmol) were used.

HRMS (70 eV, EI+): m/z calcd for C24H17N: 319.1361, found: 319.

Elemental Analysis: C, 90%; H, 5%

Synthesis Example 3: Synthesis of Compound A-1

[Reaction Scheme 3]

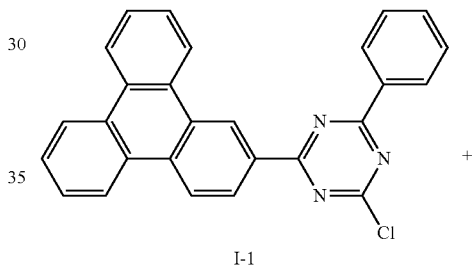

I-1

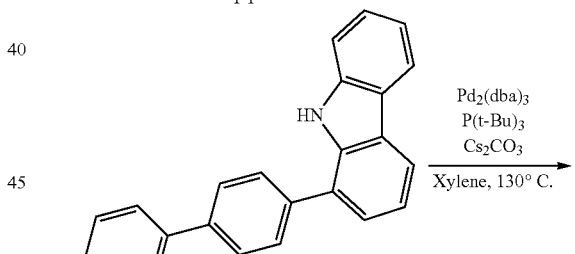

I-2

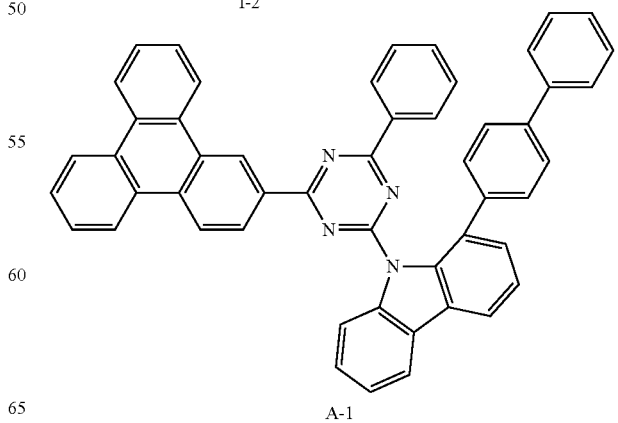

A-1

Intermediate I-1 (10 g, 23.9 mmol) was dissolved in 0.1 L of xylene under a nitrogen atmosphere, and Intermediate I-2 (7.6 g, 23.9 mmol), tris(dibenzylideneacetone) dipalladium (0) (0.66 g, 0.72 mmol), tris(tert-butyl)phosphine (0.58 g, 2.88 mmol), and cesium carbonate (2.76 g, 28.7 mmol) were sequentially added thereto and then, heated and refluxed at 130° C. for 16 hours.

When a reaction was complete, water was added to the reaction solution, and the mixture was extracted with dichloromethane (DCM), treated with anhydrous magnesium sulfate to remove moisture, filtered, and concentrated under a reduced pressure. The obtained residue was separated and purified through flash column chromatography to obtain Compound A-1 (9.38 g, 56%).

HRMS (70 eV, EI+): m/z calcd for C51H32N4: 700.2627, found: 700.

Elemental Analysis: C, 87%; H, 5%

Synthesis Example 4: Synthesis of Intermediate 1-3

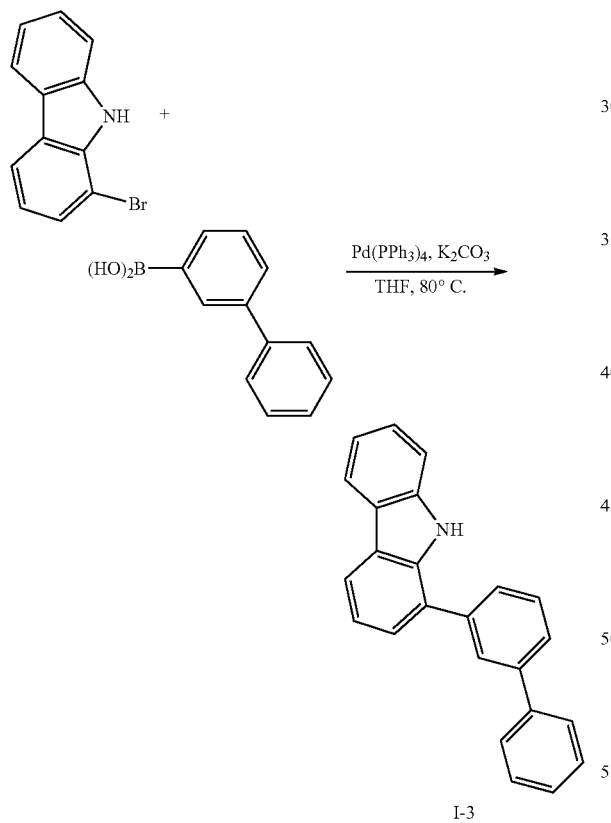

Intermediate 1-3 (31.2 g, 80%) was obtained according to the same method as Synthesis Example 1 except that 1-bromocarbazole (30 g, 122 mmol) purchased from Tokyo Chemical Industry Co., Ltd. and biphenyl-3-ylboronic acid (26.6 g, 134 mmol) were used.

HRMS (70 eV, EI+): m/z calcd for C24H17N: 319.1361, found: 319.

Elemental Analysis: C, 90%; H, 5%

Synthesis Example 5: Synthesis of Compound A-2

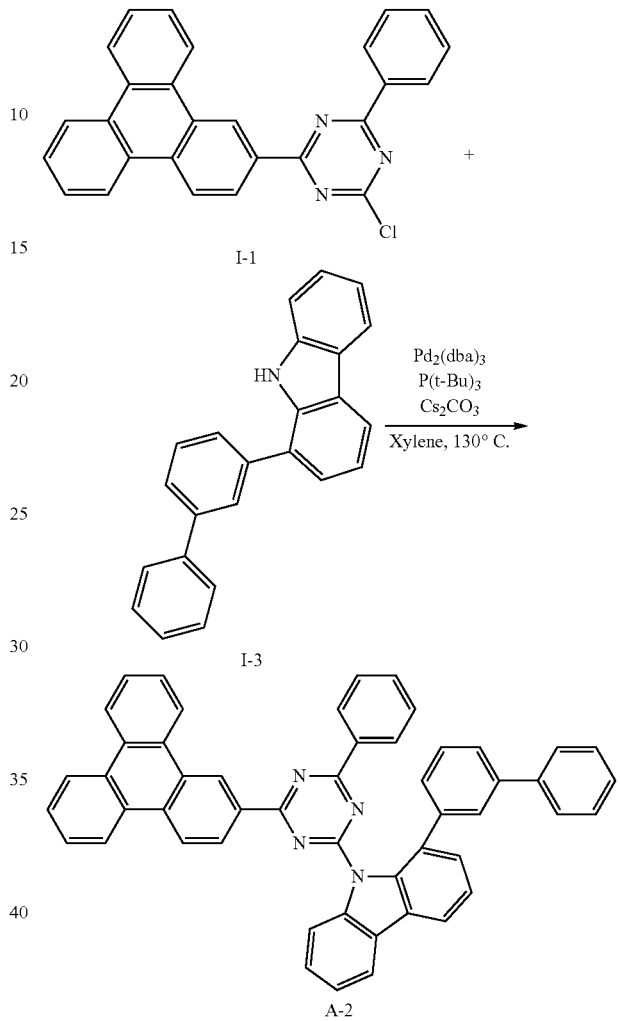

Compound A-2 (8.37 g, 50%) was obtained according to the same method as Synthesis Example 3 except that Intermediate I-1 (10 g, 23.9 mmol) and Intermediate I-3 (7.64 g, 23.9 mmol) were used.

HRMS (70 eV, EI+): m/z calcd for C51H32N4: 700.2627, found: 700.

Elemental Analysis: C, 87%; H, 5%

Synthesis Example 6: Synthesis of Intermediate 1-4

[Reaction Scheme 6]

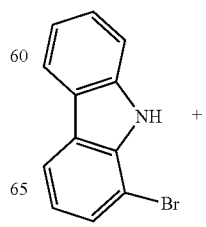

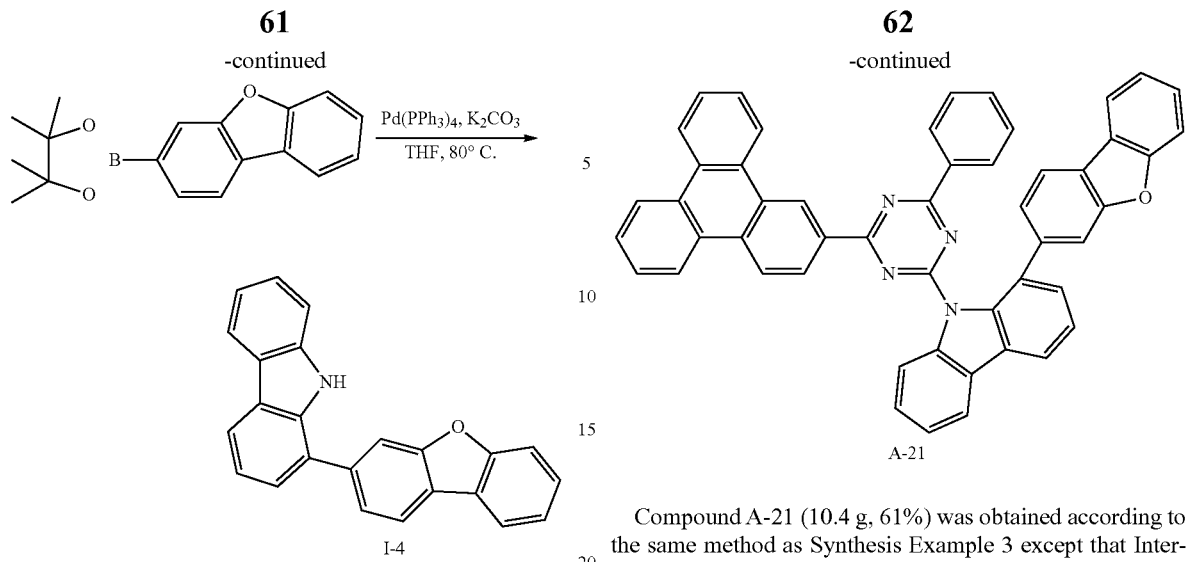

Intermediate I-4 (31.7 g, 78%) was obtained according to the same method as Synthesis Example 1 except that 1-bromocarbazole (30 g, 122 mmol) purchased from Tokyo Chemical Industry Co., Ltd. and 2-(dibenzofuran-3-yl)-4,4,5,5-tetramethyl-1,3,2-dioxaborolane (29.4 g, 134 mmol) purchased from P&H Tech Co., Ltd. were used.

HRMS (70 eV, EI+): m/z calcd for C24H15NO: 333.1154, found: 333.

Elemental Analysis: C, 86%; H, 5%

Synthesis Example 7: Synthesis of Compound A-21

[Reaction Scheme 7]

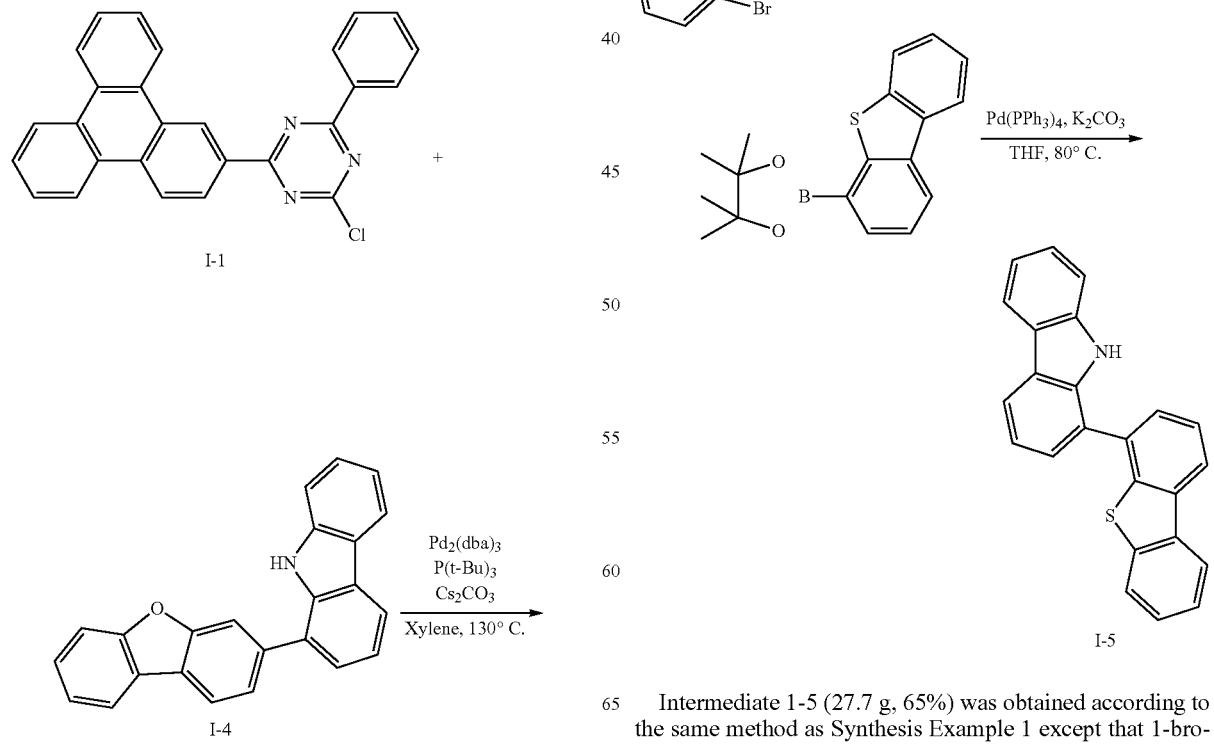

Compound A-21 (10.4 g, 61%) was obtained according to the same method as Synthesis Example 3 except that Intermediate I-1 (10 g, 23.9 mmol) and Intermediate I-4 (7.97 g, 23.9 mmol) were used.

HRMS (70 eV, EI+): m/z calcd for C51H30N4O: 714.2420, found: 714.

Elemental Analysis: C, 86%; H, 4%

Synthesis Example 8: Synthesis of Intermediate I-5

[Reaction Scheme 8]

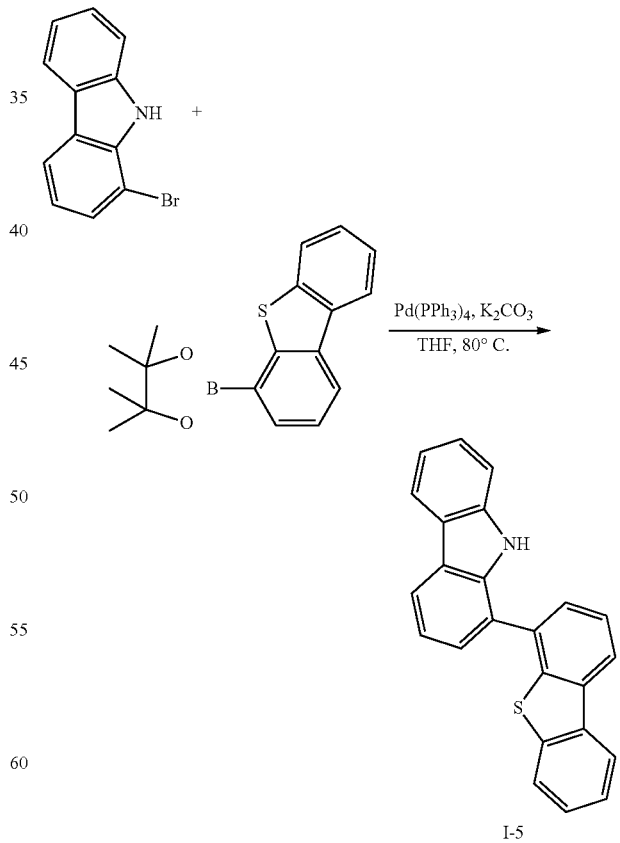

Intermediate I-5 (27.7 g, 65%) was obtained according to the same method as Synthesis Example 1 except that 1-bromocarbazole (30 g, 122 mmol) purchased from Tokyo Chemical Industry Co., Ltd. and 2-(dibenzothiophen-4-yl)-4,4,5,5-tetramethyl-1,3,2-dioxaborolane (41.6 g, 134 mmol) were used.

HRMS (70 eV, EI+): m/z calcd for C24H15NS: 349.0925, found: 349.

Elemental Analysis: C, 82%; H, 4%

Synthesis Example 9: Synthesis of Compound A-28

[Reaction Scheme 9]

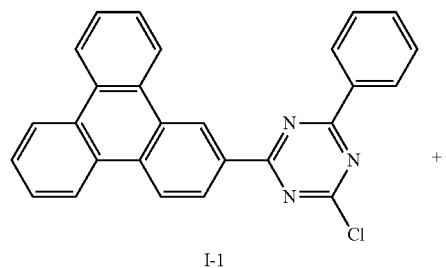

I-1

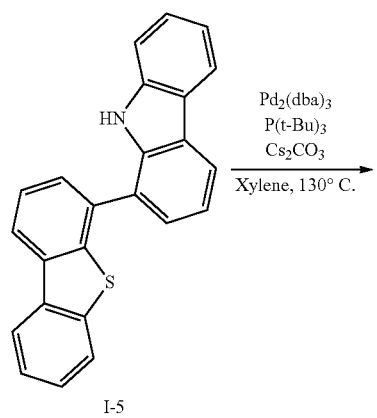

I-5

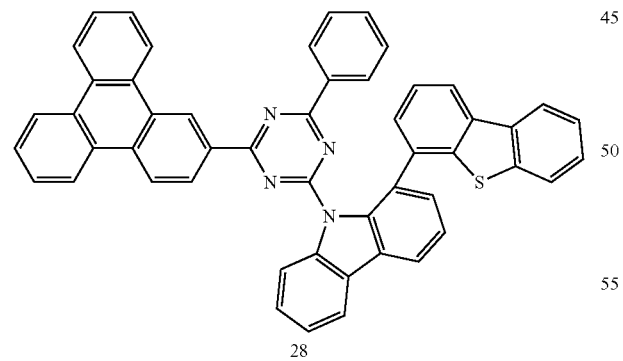

28

Compound A-28 (11.2 g, 64%) was obtained according to the same method as Synthesis Example 3 except that Intermediate I-1 (10 g, 23.9 mmol) and Intermediate I-5 (8.35 g, 23.9 mmol) were used.

HRMS (70 eV, EI+): m/z calcd for C51H30N4S: 730.2191, found: 730.

Elemental Analysis: C, 84%; H, 4%

Synthesis Example 10: Synthesis of Intermediate 1-6

[Reaction Scheme 10]

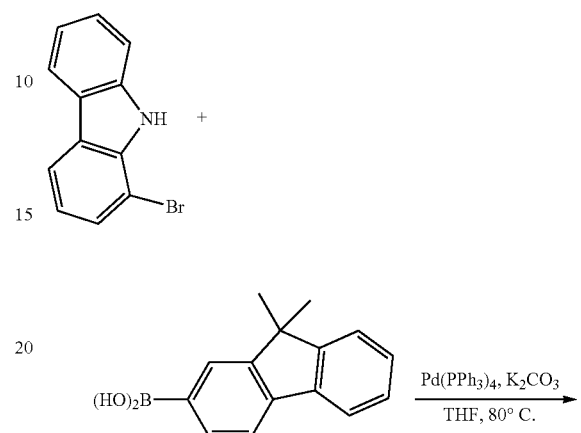

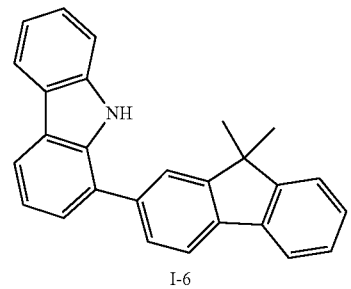

I-6

Intermediate 1-6 (30.7 g, 70%) was obtained according to the same method as Synthesis Example 1 except that 1-bromocarbazole (30 g, 122 mmol) purchased from Tokyo Chemical Industry Co., Ltd. and 9,9-dimethyl-fluoren-2-ylboronic acid (31.9 g, 134 mmol) were used.

HRMS (70 eV, EI+): m/z calcd for C27H21N: 359.1674, found: 359.

Elemental Analysis: C, 90%; H, 6%

Synthesis Example 11: Synthesis of Compound A-29

[Reaction Scheme 11]

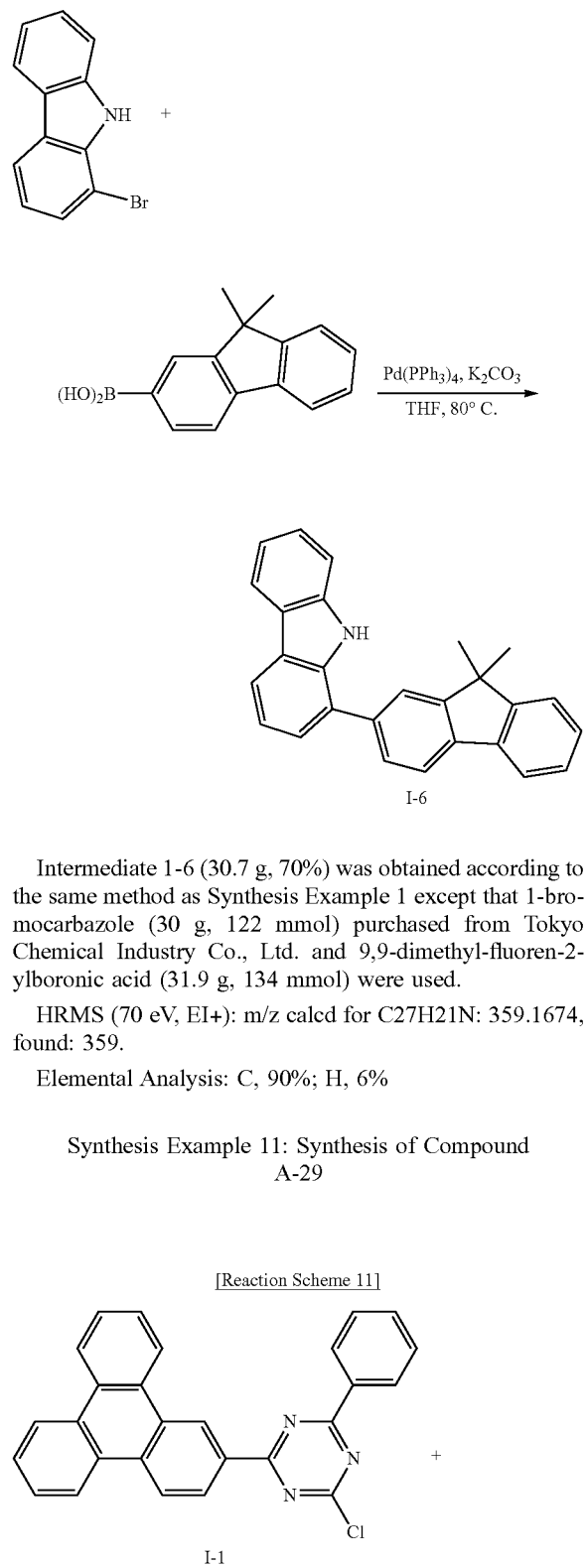

I-1

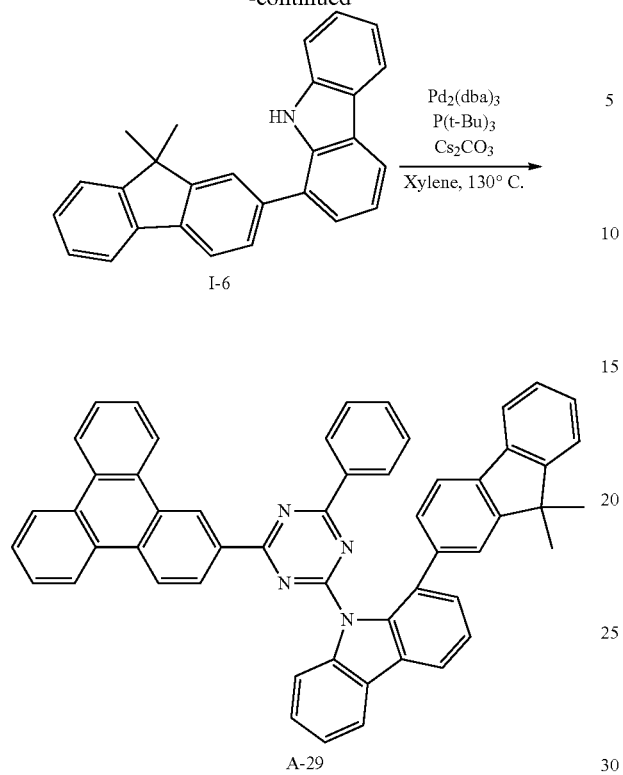

Compound A-29 (9.56 g, 54%) was obtained according to the same method as Synthesis Example 3 except that Intermediate I-1 (10 g, 23.9 mmol) and Intermediate I-6 (8.59 g, 23.9 mmol) were used.

HRMS (70 eV, EI+): m/z calcd for C54H36N4: 740.2940, found: 740.

Elemental Analysis: C, 88%; H, 5%

Synthesis Example 12: Synthesis of Host 1

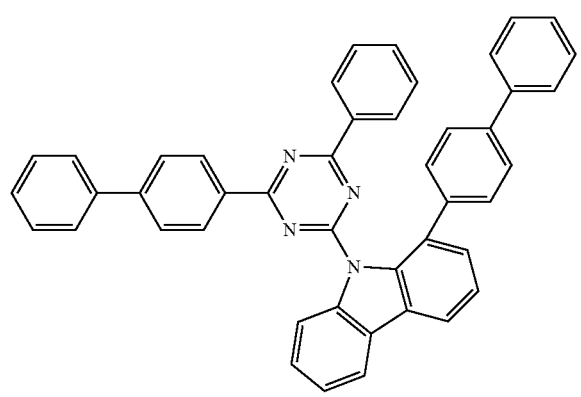

Host 1 was synthesized by referring to the synthesis method of Korean patent KR10-1183722.

HRMS (70 eV, EI+): m/z calcd for C39H24N4: 548.2001, found: 548.

Elemental Analysis: C, 85%; H, 4%

Synthesis Example 13: Synthesis of Host 2

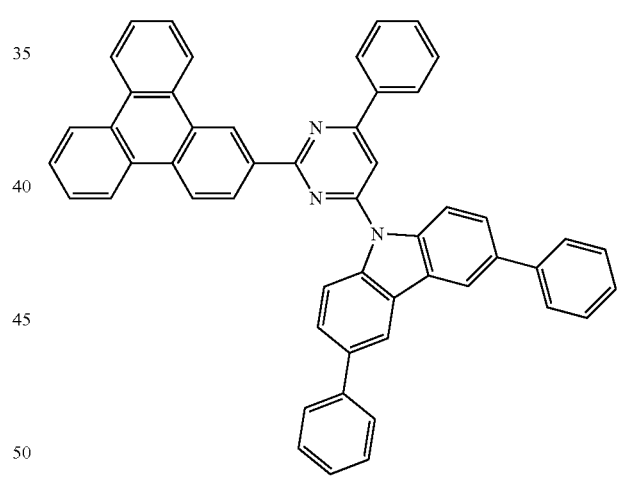

Host 2 was synthesized by referring to the synthesis method of U.S. Pat. No. 9,673,401.

HRMS (70 eV, EI+): m/z calcd for C45H30N4: 626.2470, found: 626.

Elemental Analysis: C, 86%; H, 5%

Synthesis Example 14: Synthesis of Host 3

Host 3

Host 3 was synthesized by referring to the synthesis method of WIPO publication WO2017-069258.

HRMS (70 eV, EI+): m/z calcd for C52H33N3: 699.2674, found: 699.

Elemental Analysis: C, 89%; H, 5%

Production of Organic Light Emitting Diode

Example 1

A glass substrate coated with ITO (indium tin oxide) with a thickness of 1,500 Å was washed with distilled water. After washing with the distilled water, the glass substrate was ultrasonically washed with isopropyl alcohol, acetone, methanol, or the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å-thick on the injection layer, and Compound C was deposited to be 1,020 Å-thick to form a hole transport layer. On the hole transport layer, Compound A-1 and Compound E were used as a host and 10 wt % of tris(2-phenylpyridine)iridium(III) [Ir(ppy)$_3$] was doped using vacuum deposition to form a 400 Å-thick light emitting layer. Herein Compound 1 and Compound E were used in a weight ratio of 3:7. Subsequently, Compound D and Liq were vacuum-deposited simultaneously at a 1:1 weight ratio on the light emitting layer to form a 300 Å-thick electron transport layer and a cathode was formed by sequentially vacuum-depositing Liq to be 15 Å thick and Al to be 1,200 Å thick on the electron transport layer, producing an organic light emitting diode.

The organic light emitting diode had a five-layered organic thin layer structure as follows:

ITO/Compound A (700 Å)/Compound B (50 Å)/Compound C (1,020 Å)/EML [Compound 1:Compound E: Ir(ppy)$_3$=(3:7) 90 wt %:10 wt %] (400 Å)/Compound D:Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinolone Compound E: 9,9'-di(biphenyl-4-yl)-9H,9'H-3,3'-bicarbazole

Example 2

An organic light emitting diode was produced according to the same method as Example 1 except that Compound A-2 was used instead of Compound A-1.

Example 3

An organic light emitting diode was produced according to the same method as Example 1 except that Compound A-21 was used instead of Compound A-1.

Example 4

An organic light emitting diode was produced according to the same method as Example 1 except that Compound A-28 was used instead of Compound A-1.

Example 5

An organic light emitting diode was produced according to the same method as Example 1 except that Compound A-29 was used instead of Compound A-1.

Comparative Example 1

An organic light emitting diode was produced according to the same method as Example 1 except that Host 1 was used instead of Compound A-1.

Comparative Example 2

An organic light emitting diode was produced according to the same method as Example 1 except that Host 2 was used instead of Compound A-1.

Comparative Example 3

An organic light emitting diode was produced according to the same method as Example 1 except that Host 3 was used instead of Compound A-1.

Evaluation

Driving voltages, luminous efficiency, and life-span characteristics of the organic light emitting diodes according to Examples 1 to 5 and Comparative Examples 1 to 3 were evaluated.

Specific measurement methods are as follows, and the results are shown in Table 1.

(1) Measurement of Current Density Change Depending on Voltage Change

For the produced organic light emitting diodes, while increasing the voltage from 0V to 10V, current values flowing through the unit device were measured using a current-voltmeter (Keithley 2400), and the measured current values were divided by each area to obtain results.

(2) Measurement of Luminance Change Depending on Voltage Change

For the produced organic light emitting diodes, the luminance was measured at that time using a luminance meter (Minolta Cs-1000A) while increasing the voltage from 0V to 10V, and the results were obtained.

(3) Measurement of Current Efficiency

The current efficiency (cd/A) of the same current density (10 mA/cm$^2$) was calculated using the luminance and current density measured from (1) and (2) and voltage.

(4) Measurement of Life-Span

The results were obtained by measuring a time when current efficiency (cd/A) was decreased down to 97%, while luminance (cd/m$^2$) was maintained to be 6,000 cd/m$^2$.

(5) Measurement of Driving Voltage

A driving voltage of each diode was measured using a current-voltage meter (Keithley 2400) at 15 mA/cm$^2$.

TABLE 1

| No. | Compound | Driving voltage (V) | Color (EL color) | Efficiency (cd/A) | Life-span T97 (h) |
|---|---|---|---|---|---|
| Example 1 | Compound A-1/ Compound E | 3.98 | Green | 66.5 | 1,200 |
| Example 2 | Compound A-2/ Compound E | 4.00 | Green | 65.0 | 1,450 |
| Example 3 | Compound A-21/ Compound E | 3.89 | Green | 60.5 | 1,050 |
| Example 4 | Compound A-28/ Compound E | 3.95 | Green | 60.3 | 1,150 |
| Example 5 | Compound A-29/ Compound E | 3.85 | Green | 64.1 | 950 |
| Comparative Example 1 | Host 1/ Compound E | 4.05 | Green | 55.8 | 520 |
| Comparative Example 2 | Host 2/ Compound E | 4.21 | Green | 53.5 | 310 |
| Comparative Example 3 | Host 3/ Compound E | 4.11 | Green | 58.0 | 250 |

Referring to Table 1, the organic light emitting diodes according to Examples 1 to 5 has improved driving voltage and luminous efficiency characteristics and significantly improved life-span characteristics, compared with the organic light emitting diodes according to Comparative Examples 1 to 3.

One or more embodiments may provide a compound for an organic optoelectronic device capable of implementing an organic optoelectronic device having high efficiency and long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound being represented by Chemical Formula 1:

[Chemical Formula 1]

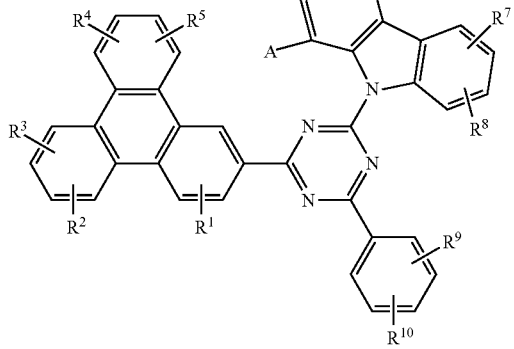

wherein, in Chemical Formula 1,

A is a substituted or unsubstituted C10 to C20 aryl group or a substituted or unsubstituted C10 to C20 heterocyclic group, $R^1$ to $R^8$ are independently hydrogen, deuterium, a substituted or unsubstituted C1 to C10 alkyl group, or a substituted or unsubstituted C6 to C20 aryl group, and $R^9$ and $R^{10}$ are independently hydrogen, deuterium, or an unsubstituted phenyl group.

2. The compound as claimed in claim 1, wherein the compound represented by Chemical Formula 1 is represented by one of Chemical Formulae 1-1 to 1-4:

[Chemical Formula 1-1]

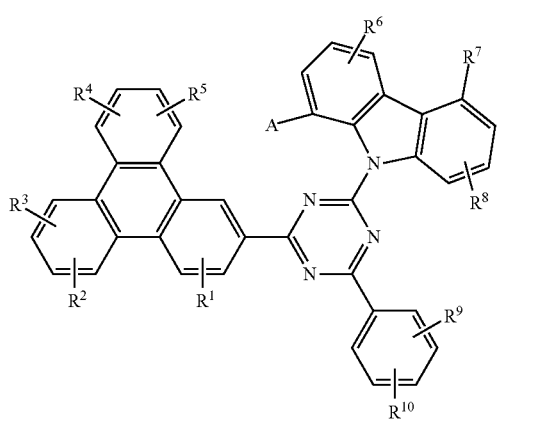

[Chemical Formula 1-2]

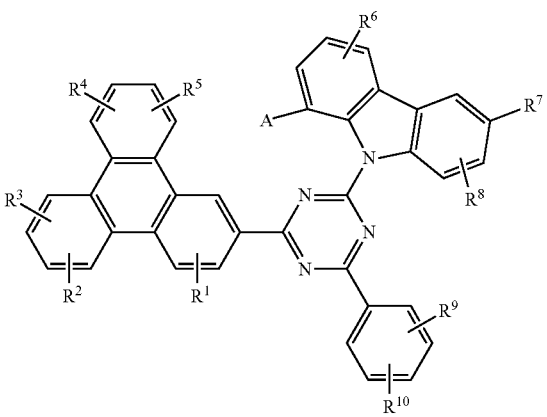

[Chemical Formula 1-3]

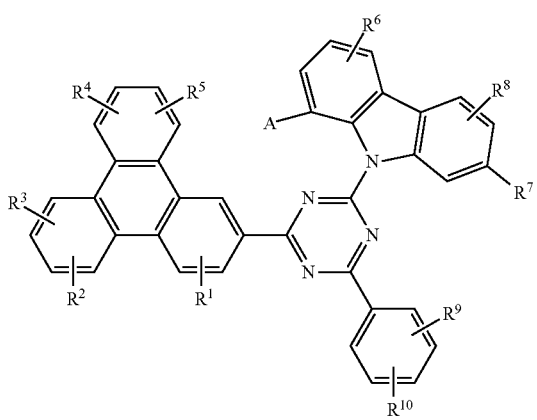

[Chemical Formula 1-4]

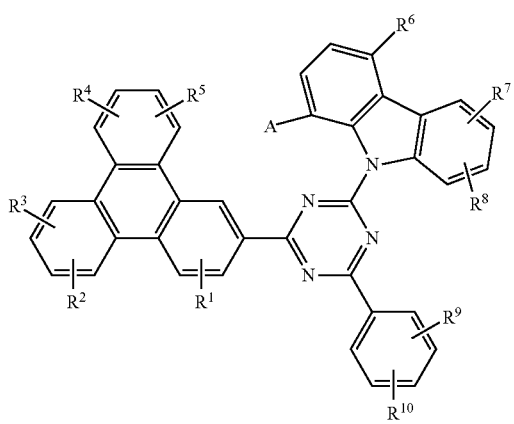

in Chemical Formulae 1-1 to 1-4, A and $R^1$ to $R^{10}$ are defined the same as those of Chemical Formula 1.

3. The compound as claimed in claim 1, wherein A is a substituted or unsubstituted biphenyl group, a substituted or unsubstituted terphenyl group, a substituted or unsubstituted fluorenyl group, a substituted or unsubstituted dibenzofuranyl group, or a substituted or unsubstituted dibenzothiophenyl group.

4. The compound as claimed in claim 1, wherein A is a substituent of Group I:

[Group I]

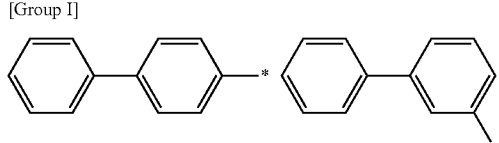
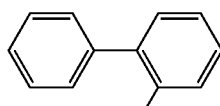
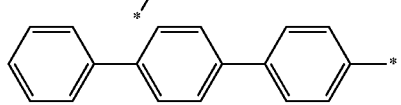
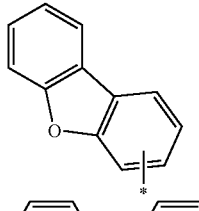
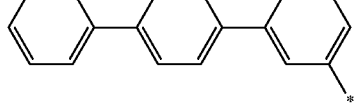
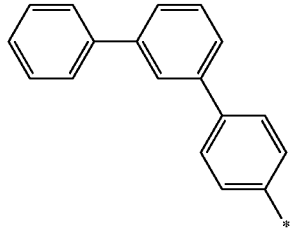
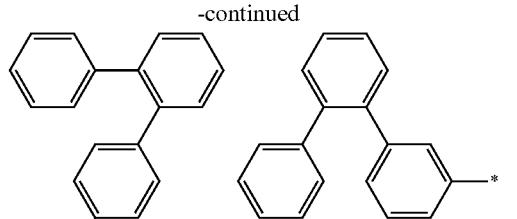
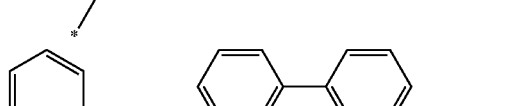
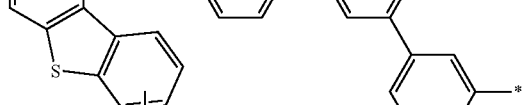
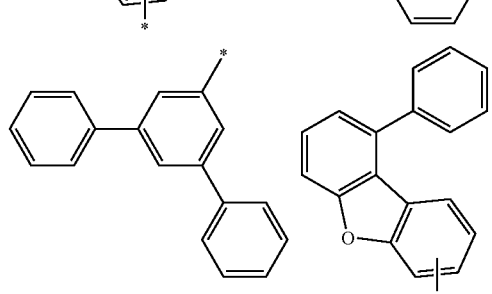
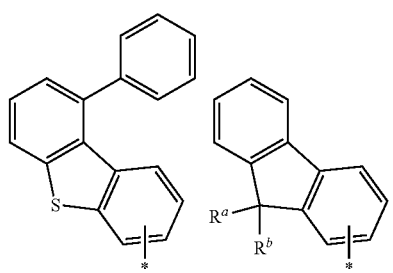

in Group I, $R^a$ and $R^b$ are independently a substituted or unsubstituted C1 to C6 alkyl group or a substituted or unsubstituted C6 to C12 aryl group, and \* is a linking point.

5. The compound as claimed in claim 1, wherein the compound represented by Chemical Formula 1 is a compound of Group 1:

[Group 1]

[A-1]

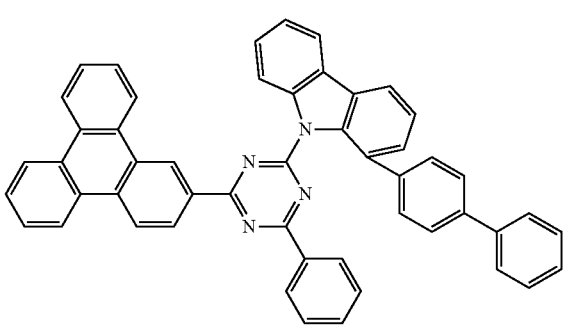

[A-2]
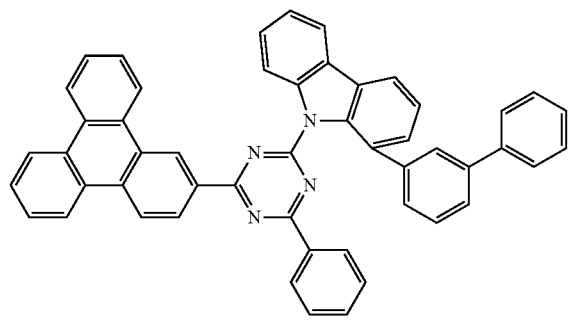
[A-3]
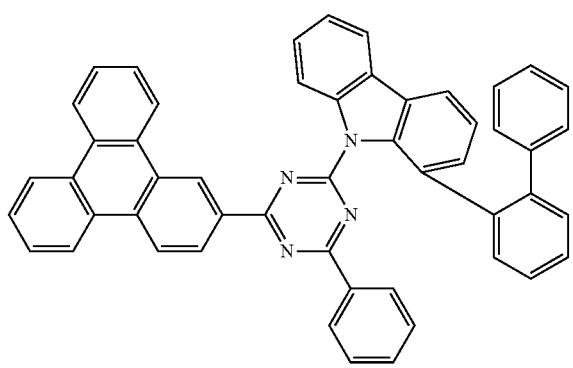
[A-4]
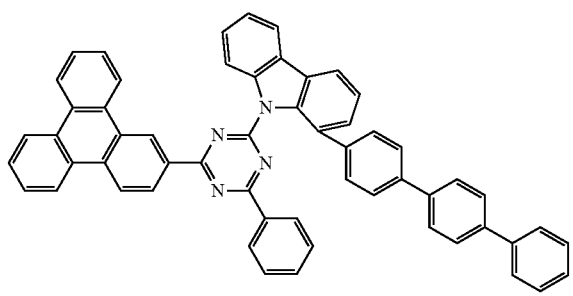
[A-5]
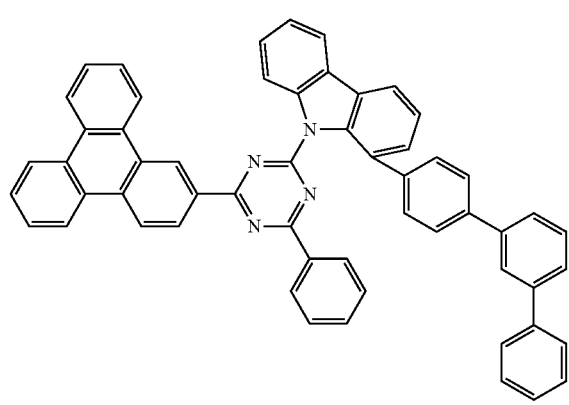
[A-6]
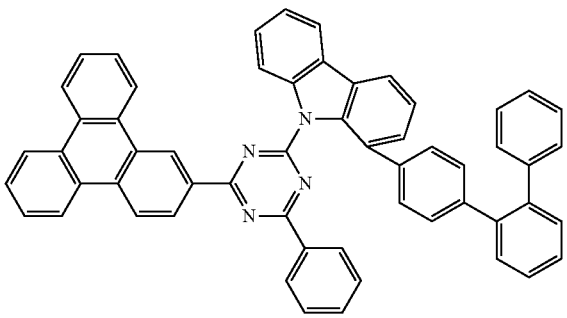
[A-7]
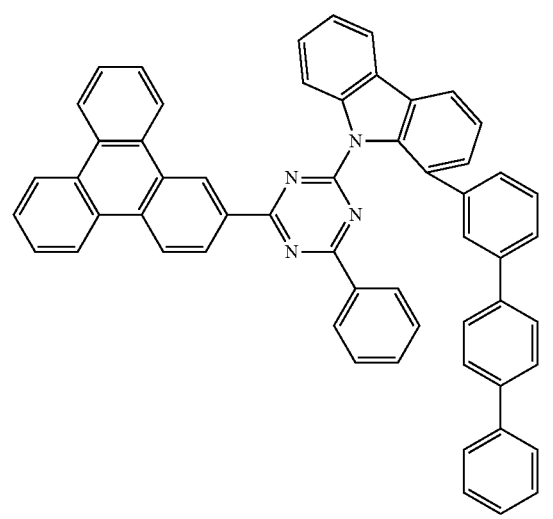
[A-8]
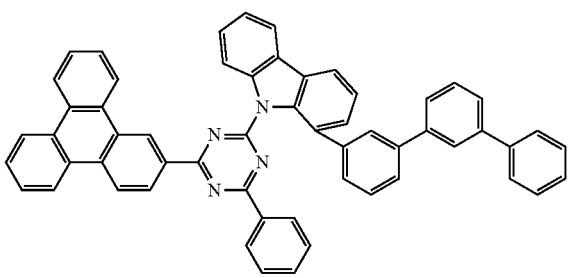
[A-9]
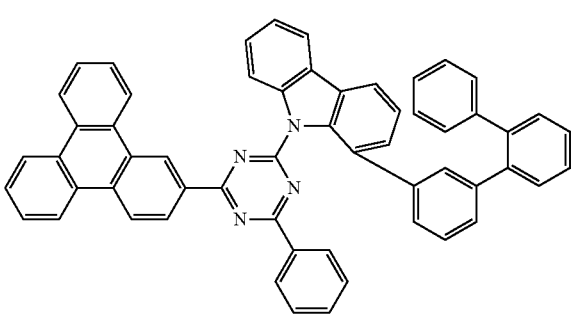

[A-10]
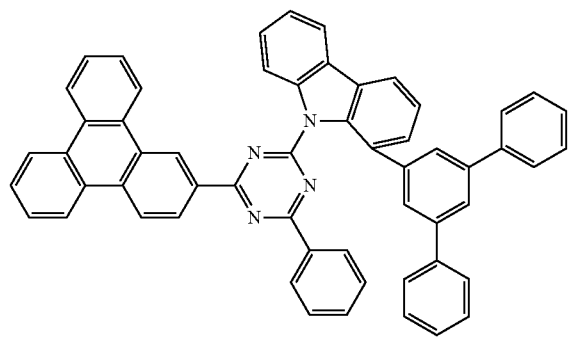
[A-11]
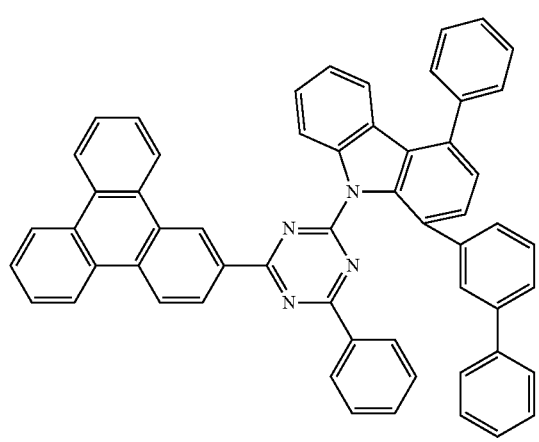
[A-12]
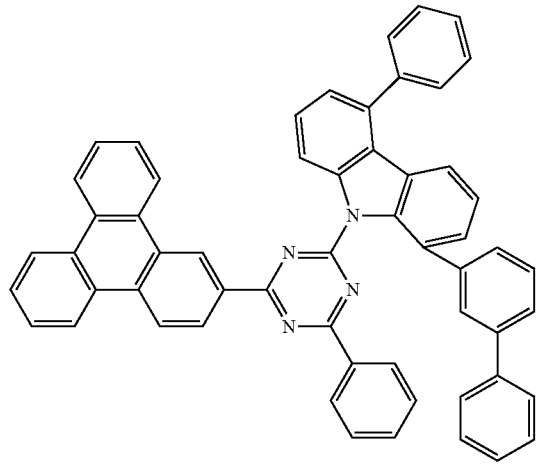
[A-13]
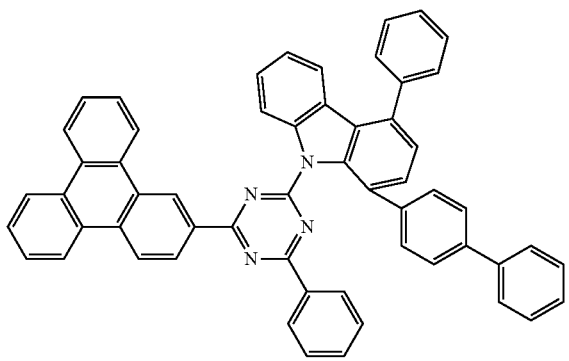
[A-14]
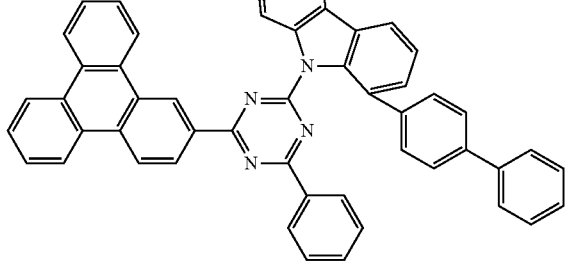
[A-15]
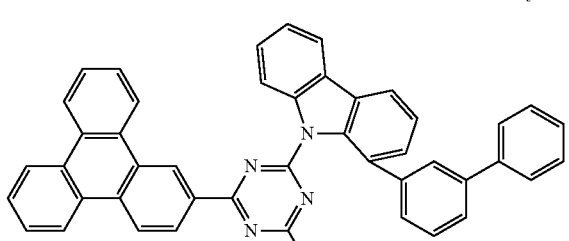
[A-16]
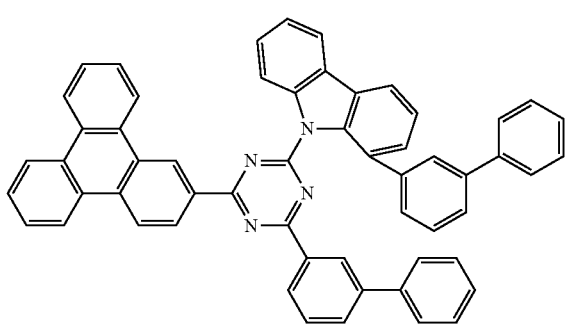

[A-17]
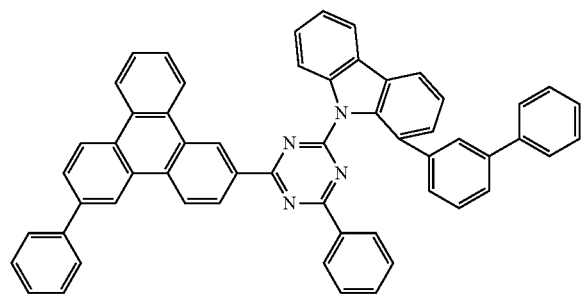
[A-21]
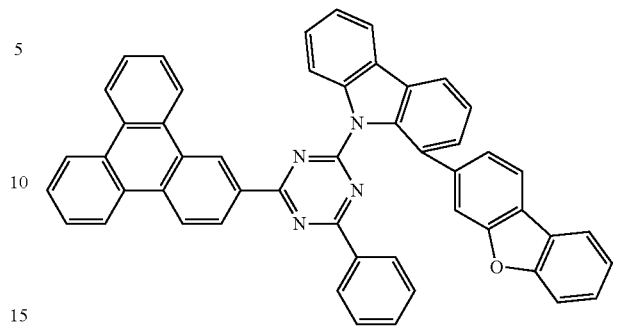
[A-18]
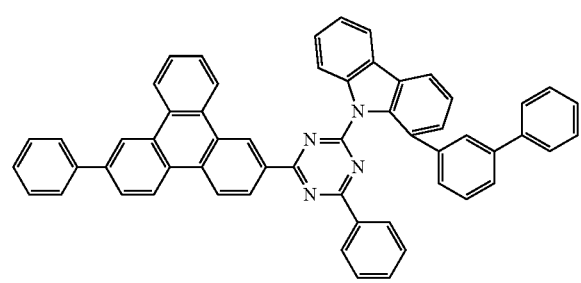
[A-22]
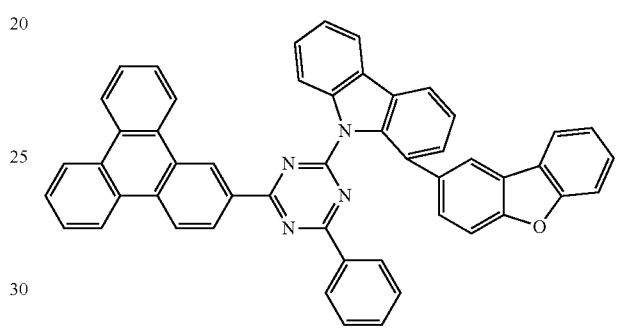
[A-19]
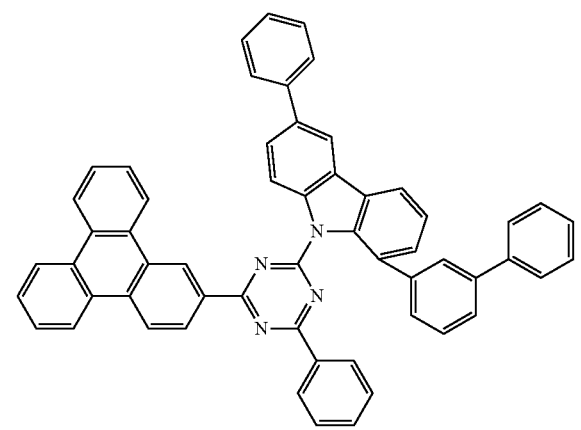
[A-23]
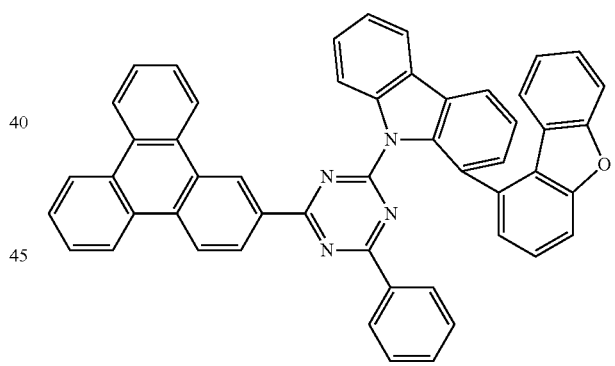
[A-20]
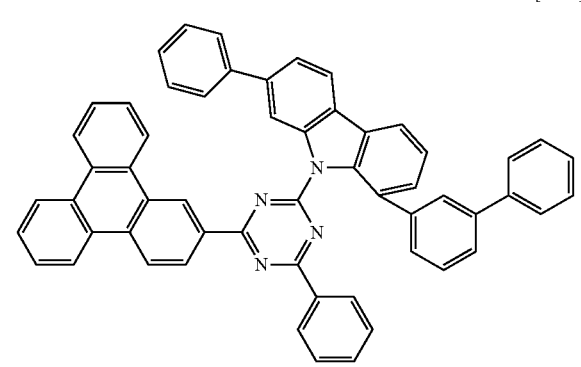
[A-24]
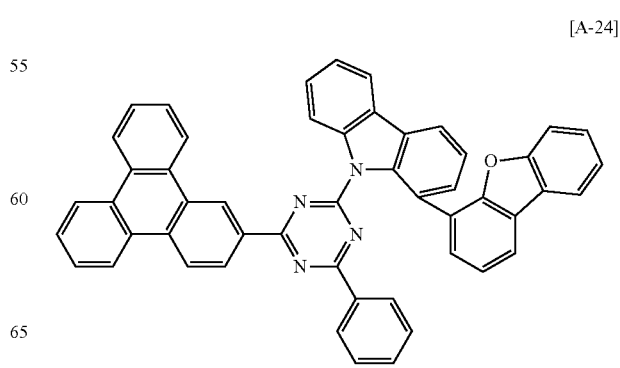

[A-25]
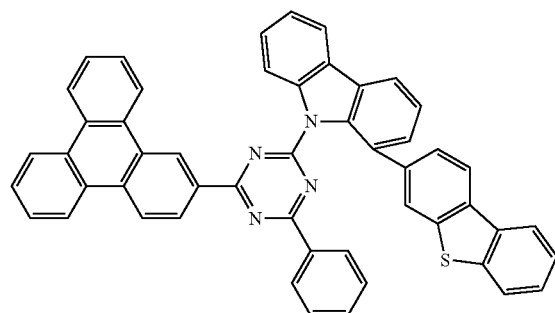
[A-29]
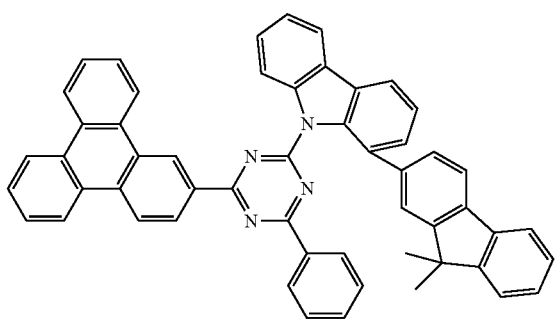
[A-26]
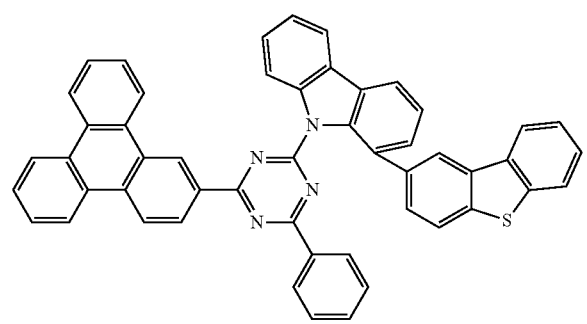
[A-30]
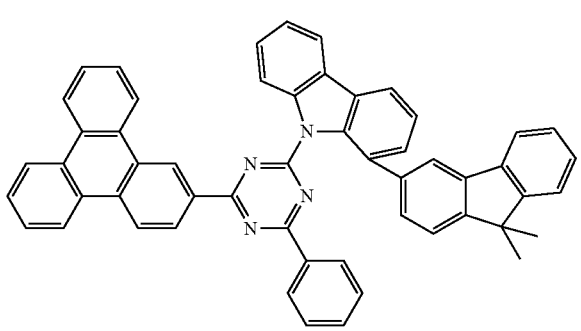
[A-27]
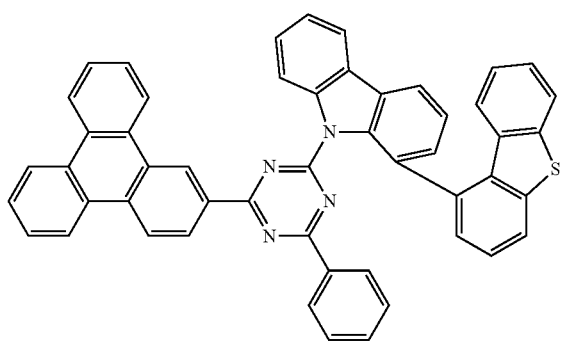
[A-31]
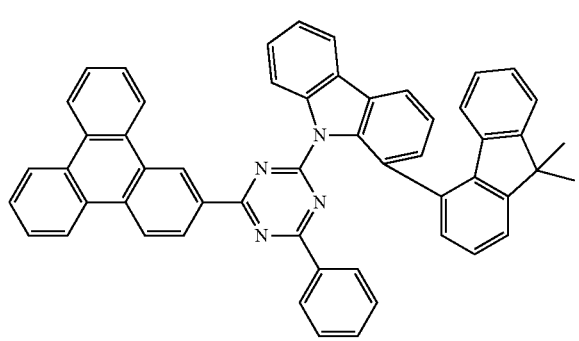
[A-28]
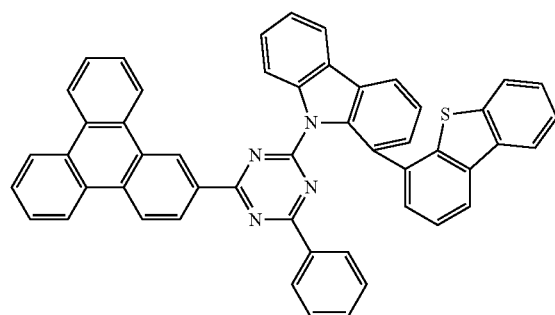
[A-32]
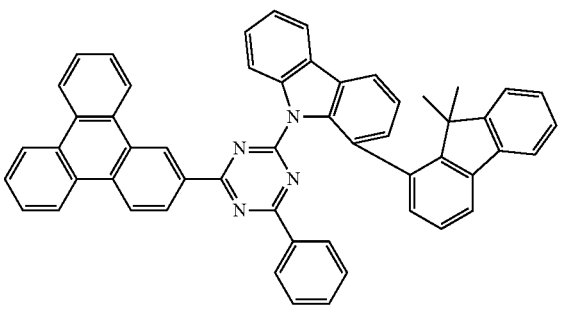

[A-33]
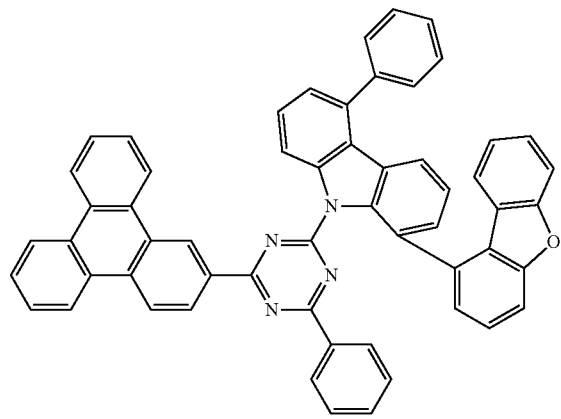
[A-34]
[A-37]
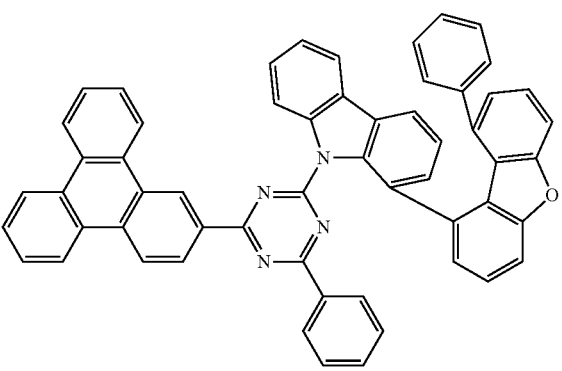
[A-38]
[A-35]
[A-39]
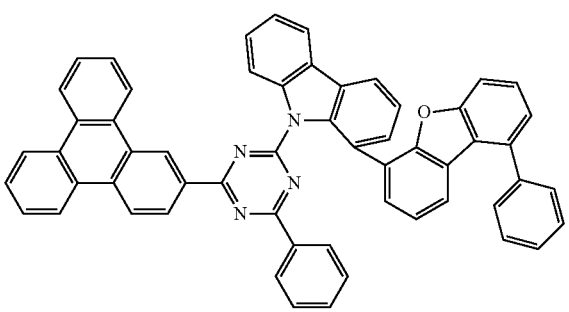
[A-36]
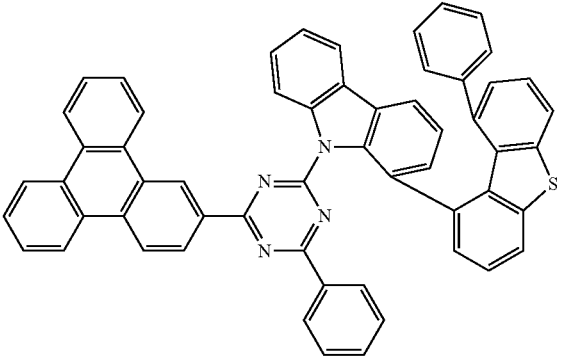
[A-40]
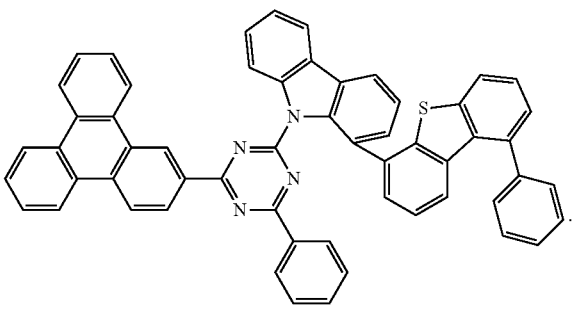
6. An organic optoelectronic device, comprising:
an anode and a cathode facing each other, and
at least one organic layer between the anode and the cathode,
wherein the at least one organic layer includes the compound as claimed in claim 1.

7. The organic optoelectronic device as claimed in claim 6, wherein:

the at least one organic layer includes a light emitting layer, and the light emitting layer includes the compound.

8. A display device comprising the organic optoelectronic device as claimed in claim 6.

9. The compound as claimed in claim 1, wherein A is a substituent of Group I':

[Group I']

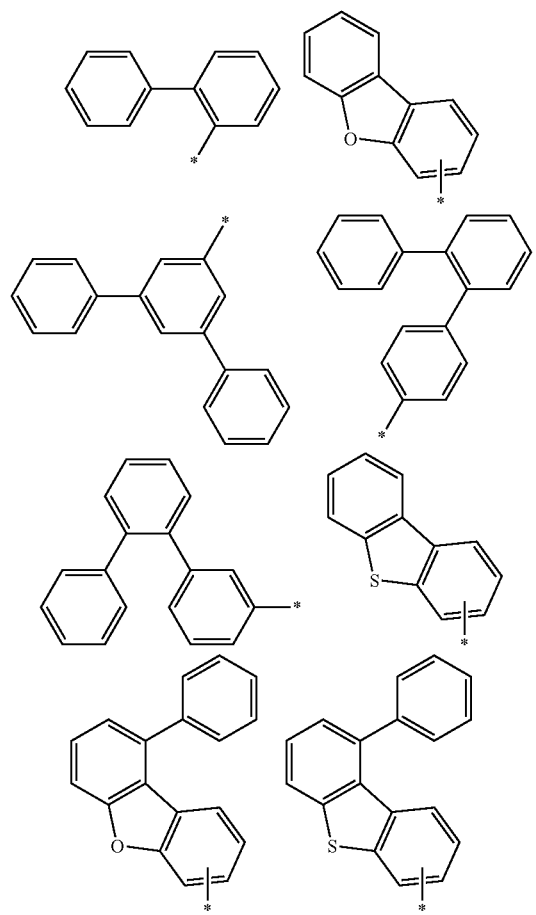

in Group I',

R$^a$ and R$^b$ are independently a substituted or unsubstituted C1 to C6 alkyl group or a substituted or unsubstituted C6 to C12 aryl group, and

* is a linking point.

10. The compound as claimed in claim 1, wherein A is a substituent of Group I':

[Group I'']

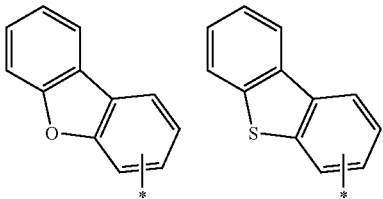

in Group I'',

R$^a$ and R$^b$ are independently a substituted or unsubstituted C1 to C6 alkyl group or a substituted or unsubstituted C6 to C12 aryl group, and

* is a linking point.

11. The compound as claimed in claim 1, wherein the compound represented by Chemical Formula 1 is a compound of Group 1':

[Group 1']

[A-21]

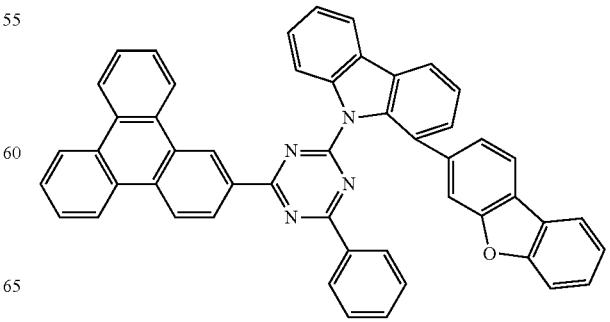

[A-22]
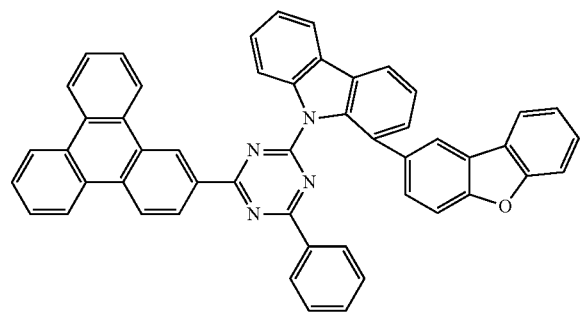
[A-26]
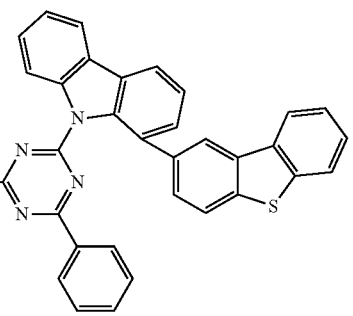
[A-23]
[A-27]
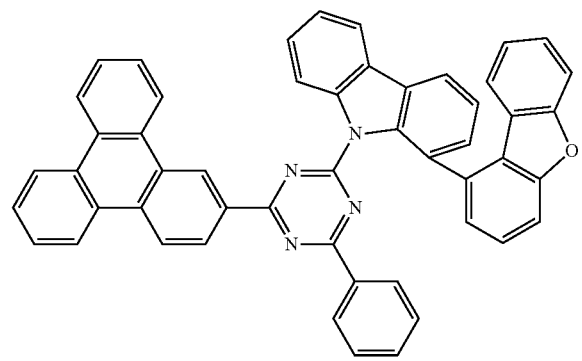
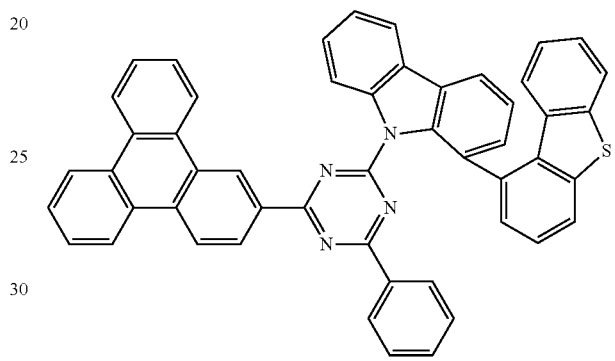
[A-24]
[A-28]
[A-25]
[A-29]
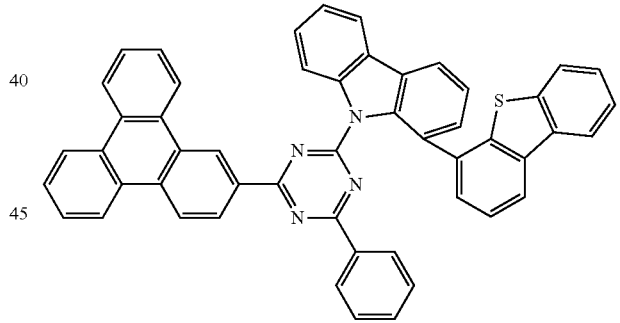

[A-30]
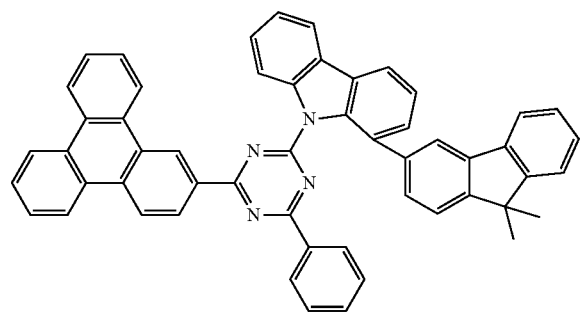
[A-31]
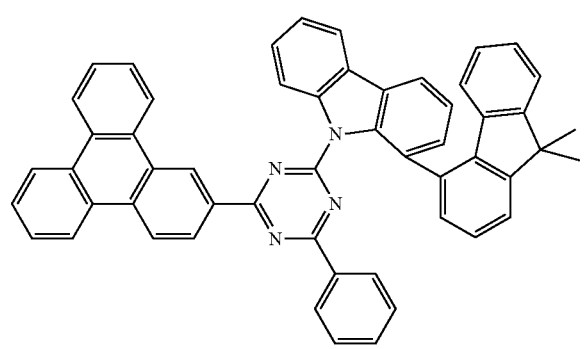
[A-32]
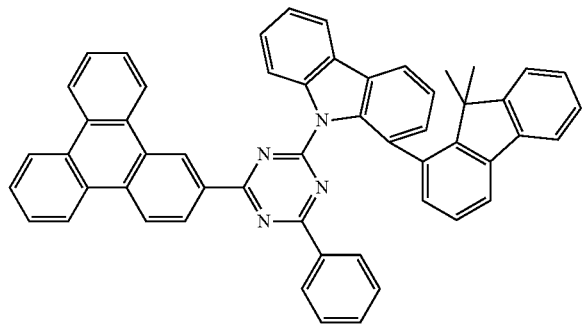
[A-33]
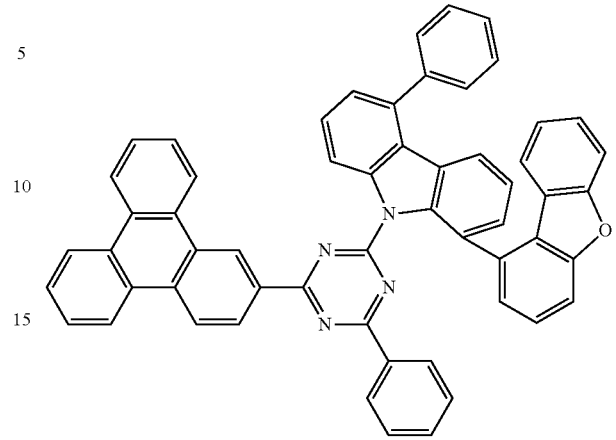
[A-34]
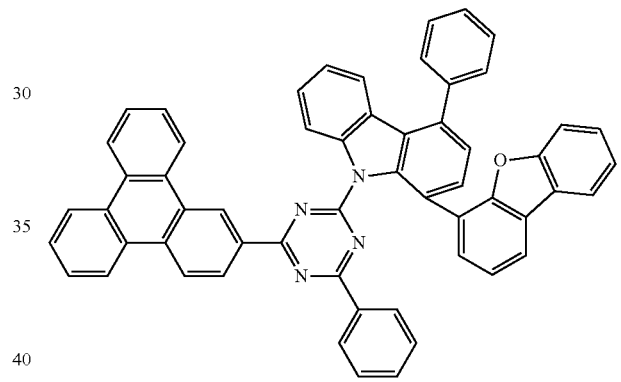
[A-35]
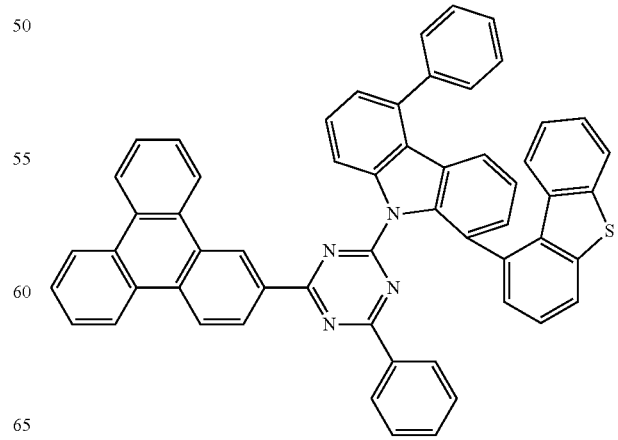

[A-36]
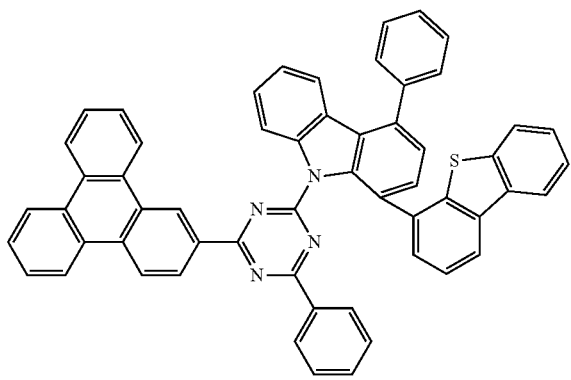
[A-37]
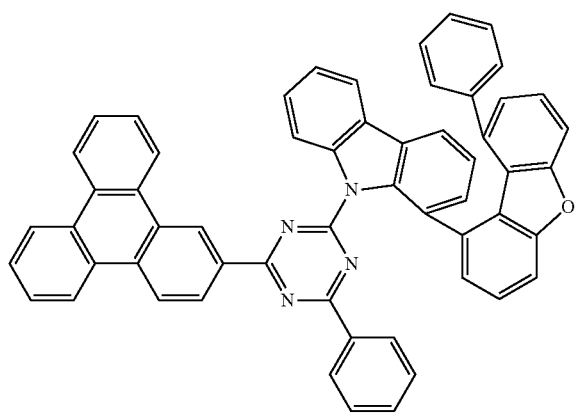
[A-38]
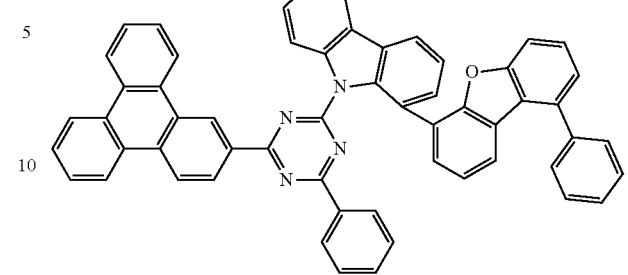
[A-39]
[A-40]
* * * * *